US009155819B2

(12) United States Patent
Fonte et al.

(10) Patent No.: US 9,155,819 B2
(45) Date of Patent: Oct. 13, 2015

(54) DYNAMIC POROUS COATING FOR ORTHOPEDIC IMPLANT

(71) Applicant: MX Orthopedics, Corp., Billerica, MA (US)

(72) Inventors: Matthew Fonte, Concord, MA (US); Matthew Palmer, Cambridge, MA (US)

(73) Assignee: MX Orthopedics, Corp., Cambridge, MA (US)

( * ) Notice: Subject to any disclaimer, the term of this patent is extended or adjusted under 35 U.S.C. 154(b) by 0 days.

(21) Appl. No.: 13/843,656

(22) Filed: Mar. 15, 2013

(65) Prior Publication Data

US 2013/0218288 A1  Aug. 22, 2013

Related U.S. Application Data

(63) Continuation-in-part of application No. 13/764,188, filed on Feb. 11, 2013.

(60) Provisional application No. 61/596,900, filed on Feb. 9, 2012, provisional application No. 61/612,496, filed on Mar. 19, 2012, provisional application No. 61/661,086, filed on Jun. 18, 2012, provisional application No. 61/738,574, filed on Dec. 18, 2012.

(51) Int. Cl.
*A61F 2/28* (2006.01)
*A61L 27/56* (2006.01)
(Continued)

(52) U.S. Cl.
CPC .............. *A61L 27/56* (2013.01); *A61F 2/30767* (2013.01); *A61F 2/30907* (2013.01); *A61F 2/3662* (2013.01); *A61F 2/3094* (2013.01); *A61F 2/34* (2013.01); *A61F 2/38* (2013.01); *A61F 2002/3028* (2013.01); *A61F 2002/3084* (2013.01); *A61F 2002/3092* (2013.01); *A61F 2002/30092* (2013.01); *A61F 2002/30579* (2013.01); *A61F 2002/30911* (2013.01); *A61F 2002/30912* (2013.01); *A61F 2002/30914* (2013.01); *A61F 2002/30915* (2013.01); *A61F 2002/30919* (2013.01); *A61F 2002/30929* (2013.01)

(58) Field of Classification Search
CPC ................... A61F 2002/30092; A61F 2/3662; A61F 2/30767; A61F 2/30907; A61F 2002/30911; A61F 2002/30912; A61F 2002/30915
USPC .................................. 623/23.3, 23.54, 23.55
See application file for complete search history.

(56) References Cited

U.S. PATENT DOCUMENTS 3,906,550 A  9/1975  Rostoker et al.
4,536,894 A  8/1985  Galante et al.
(Continued)

OTHER PUBLICATIONS

Galante, Jorge, et al. "Sintered Fiber Metal Composites as a Basis for Attachment of Implants to Bone." The Journal of Bone and Joint Surgery, vol. 53-A, No. 1, Jan. 1971.
(Continued)

*Primary Examiner* — Bruce E Snow
*Assistant Examiner* — Brian Dukert
(74) *Attorney, Agent, or Firm* — Pandiscio & Pandiscio

(57) ABSTRACT

A dynamic porous coating for an orthopedic implant, wherein the dynamic porous coating is adapted to apply an expansive force against adjacent bone so as to fill gaps between the dynamic porous coating and adjacent bone and to create an interference fit between the orthopedic implant and the adjacent bone.

9 Claims, 63 Drawing Sheets

(51) Int. Cl.
 *A61F 2/30* (2006.01)
 *A61F 2/36* (2006.01)
 A61F 2/34 (2006.01)
 A61F 2/38 (2006.01)

(56) References Cited

U.S. PATENT DOCUMENTS

| | | | |
|---|---|---|---|
| 4,636,219 | A | 1/1987 | Pratt et al. |
| 4,693,721 | A | 9/1987 | Ducheyne |
| 4,863,475 | A | 9/1989 | Andersen et al. |
| 4,975,230 | A | 12/1990 | Pinkhasov |
| 5,011,638 | A | 4/1991 | Pinkhasov |
| 5,198,308 | A | 3/1993 | Shetty et al. |
| 5,282,861 | A | 2/1994 | Kaplan |
| 5,926,685 | A | 7/1999 | Krebs et al. |
| 5,986,169 | A | 11/1999 | Gjunter |
| 6,087,553 | A | 7/2000 | Cohen et al. |
| 6,103,149 | A | 8/2000 | Stankiewicz |
| 6,913,622 | B2 | 7/2005 | Gjunter |
| 6,929,866 | B1 | 8/2005 | Williams et al. |
| 7,458,991 | B2 | 12/2008 | Wang et al. |
| 7,578,851 | B2 | 8/2009 | Dong et al. |
| 7,883,661 | B2 | 2/2011 | Hamman et al. |
| 8,062,378 | B2 * | 11/2011 | Fonte ............ 623/23.26 |
| 8,585,770 | B2 * | 11/2013 | Meridew et al. ........ 623/23.46 |
| 2006/0015183 | A1 | 1/2006 | Gilbert et al. |
| 2011/0245930 | A1 | 10/2011 | Alley et al. |

OTHER PUBLICATIONS

Bauer, Thomas W. et al., Hydroxyapatite-Coated Femoral Stems, The Journal of Bone and Joint Surgery, Dec. 1991, pp. 1439-1452, vol. 73-A(10).

Coathup, M.J. et al., A comparison of bone remodelling around hydroxyapatite-coated, porous-coated and grit-blasted hip replacements retrived at post-mortem, The Journal of Bone & Joint Surgery (Br), Jan. 2001, pp. 118-123, vol. 83-B(1).

Galante, Jorge et al., Sintered Fiber Metal Composites as a Basis for Attachment of Implants to Bone, Jan. 1971, pp. 101-114, vol. 53-A(1).

Harris, William H. et al., Total Hip and Total Knee Replacement, The New England Journal of Medicine, 1990, pp. 801-807, vol. 323(12).

Landon, Glenn C., Noncemented Total Knee Arthroplasty, Clinical Orthopedics and Related Research, Apr. 1986, pp. 49-57, vol. 205.

Lembert, E. et al., Fixation of Skeletal Replacement by Fiber Metal Composites, Clinical Orthopedics and Related Research, Sep. 1972, pp. 303-310, vol. 87.

Mayman, David J. et al., Late Fiber Metal Shedding of the First and Second-Generation Harris Galante Acetabular Component. A Report of 5 Cases, The Journal of Arthroplasty, Jun. 2007, pp. 624-629, vol. 22(4).

Nelson, Carl L., A Comparison of Gentamicin-Impregnated Polymethylmethacrylate Bead Implantation to Conventional Parenteral Antibiotic Therapy in Infected Total Hip and Knee Arthroplasty, Clinical Orthopedics and Related Research, Oct. 1993, pp. 96-101, vol. 295.

Pidhorz, Laurent E. et al., A Quantitative Study of Bone and Soft Tissues in Cementless Porous-coated Acetabular Components Retrieved at Autopsy, The Journal of Arthroplasty, Apr. 1993, pp. 213-225, vol. 8(2).

Spector, Myron, Historical Review of Porous-coated Implants, The Journal of Arthroplasty, Jun. 1987, pp. 163-177, vol. 2(2).

Tonino, Alphons J. et al., Hydroxyapatite-coated femoral stems: Histology and Histomorphometry Around Five Components Retrieved at Post Mortem, The Journal of Bone & Joint Surgery (Br), Jan. 1999, pp. 148-154, vol. 81-B(1).

Venesmaa, Petri K. et al., Monitoring of Periprosthetic BMD After Uncemented Total Hip Arthroplasty with Dual-Energy X-Ray Absorptiometry—a 3-Year Follow-Up Study, Journal of Bone and Mineral Research, 2001, pp. 1056-1061, vol. 16(6).

Orthopedic Network News, 2010 Hip and Knee Implant Review, Jul. 2010, pp. 1 and 3, vol. 21(3).

Lueck, Roger A. et al., Development of an Open Pore Metallic Implant to Permit Attachment to Bone, Orthopedic Surgery, 1969, pp. 456-457.

Gustilo, Ramon B. et al., Revision Total Hip Arthroplasty with Titanium Ingrowth Prosthesis and Bone Grafting for Failed Cemented Femoral Component Loosening, Clinical Orthopaedics and Related Research, Oct. 1988, pp. 111-119, vol. 235.

Sumner, D.R. et al., Remodeling and Ingrowth of Bone at Two Years in a Canine Cementless Total Hip-Arthroplasty Model, The Journal of Bone and Joint Surgery, Feb. 1992, pp. 239-250, vol. 74-A(2).

Urban, Robert M. et al., The Bone-Implant Interface of Femoral Stems with Non-Circumferential Porous Coating, The Journal of Bone and Joint Surgery, 1996, pp. 1068-1081.

* cited by examiner

EXISTENCE OF GAPS BETWEEN IMPLANT SURFACE AND BONE

HIP IMPLANT IN THE FEMORAL CANAL, WITH A POROUS COATING
BONDING/INTERFACING BETWEEN THE IMPLANT AND BONE

SURFACE FEATURES OF IMPLANT COATING

TRABECULAR BONE WITH INTERCONNECTING PORES

PROCESS FOR MAKING OPEN CELL TITANIUM COATING

OPEN CELL CARBON FOAM

OPEN CELL TANTALUM COATING

PROCESS FOR THICKENING POROUS COATING

POLYURETHANE FOAM WITH
DODECAHEDRON STRUCTURE

SHAPE MEMORY
MATERIAL COATED
FOAM

CLOSE UP VIEW OF
COATED FOAM

STRUT WITH EXPOSED HYDROXYAPATITE INTERIOR AND
SHAPE MEMORY SKIN

POROUS NITINOL SCAFFOLD PRODUCED USING SHS METHOD

WEFT KNIT

WARP KNIT

EXAMPLES OF SHAPE MEMORY MATERIAL SPACER FABRICS

SPACER FABRIC POROUS, ELASTIC, DYNAMIC COATING

THREE DISCRETE LAYERS OF SPACER FABRIC

SPACER FABRIC CREATED WITH VERTICAL, INTERCONNECTING
FIBERS IN THE MIDDLE LAYER

SPACER FABRIC, TRABECULAR GEOMETRY TOP LAYER ADJACENT TO BONE
TISSUE WITH SAME 3D STRUCTURE

EXEMPLARY ORTHOPEDIC IMPLANTS WITH DYNAMIC POROUS COATING
FORMED OUT OF SHAPE MEMORY MATERIAL SPACER FABRIC

DYNAMIC POROUS COATING FILLING THE GAP
BETWEEN ORTHOPEDIC IMPLANT AND THE BONE

DYNAMIC POROUS COATING FORMED OUT OF NITINOL, SUPERELASTIC WIRE
~ MEAN PORE SIZE OF 243 μm AND ~ 92.5% POROUS

FOUR BASIC WEAVING TECHNIQUES

DIFFERENT POROUS WEAVING PATTERNS

WEAVING A THREE DIMENSIONAL POROUS STRUCTURE

MANUFACTURING OF HELICAL WIRES FROM TWISTED WIRE

SINGLE LAYER OF WBK STRUCTURE

SINGLE LAYER OF WBK STRUCTURE IN FIXING FRAME

PRODUCTION OF WBK STRUCTURE

SPHERICAL PORES OF WBK, CONSTRUCTION OF WBK USING TUBES,
VARIOUS AMOUNTS OF FILLER USED IN BRAZING PROCESS

COMPRESSIVE BEHAVIOR OF WBK STRUCTURE

CORRUGATION OF A MESH SURFACE INTO A PYRAMIDAL STRUCTURE

CORRUGATION OF INDIVIDUAL LAYERS FOLLOWED BY
STACKING ONE ON TOP OF EACH OTHER

CORRUGATION OF LAYERED STRUCTURE

CORRUGATED STRUCTURE WITH ATTACHED LESS POROUS SHEET

NITINOL (SHAPE MEMORY ALLOY), SUPERELASTIC
HONEYCOMB STRUCTURE

NITINOL (SHAPE MEMORY ALLOY), SUPERELASTIC
TRUSS STRUCTURE

3D DODECAHEDRON STRUCTURE

3D DODECAHEDRON HONEYCOMB MADE OF SMM

HOBE MANUFACTURING PROCESS FOR CREATING HONEYCOMB

PRESS CORRUGATION METHOD FOR CREATING HONEYCOMB

STRIP SLOTTING METHOD FOR CREATING HONEYCOMB

HONEYCOMB STRUCTURES WITH HOLES TO INCREASE POROSITY

STAGGERING OF HONEYCOMB ELEMENTS TO INCREASE POROSITY

POROUS HONEYCOMB COATING SURROUNDING IMPLANT STEM

DYNAMIC POROUS STRUCTURE USING BEADS OF THE SAME DIAMETER

DYNAMIC POROUS STRUCTURE USING BEADS OF DIFFERENT DIAMETER

CREATION OF A DYNAMIC POROUS SURFACE USING JACK-SHAPED BEADS

SHEETS OF NITINOL WITH DIFFERENT PATTERNS CUT OUT

POROUS LAMINATED STRUCTURE

POROUS STRUCTURES THAT CAN BE CREATED USING
ADDITIVE MANUFACTURING TECHNIQUES

POROUS COATING WITH ENHANCED NANO-TEXTURING

MICRO AND NANO STRUCTURE OF BONE

MATERIAL PROPERTIES OF CORTICAL AND CANCELLOUS BONE

STRESS-STRAIN DIAGRAM (SCHEMATIC), FOR LIVING TISSUES, NITI SUPERELASTIC ALLOY AND STAINLESS STEEL (THE LEFT ARROW INDICATES THE ELASTIC LIMIT IN STAINLESS STEEL)

AUSTENITE PHASE, MARTENSITE PHASE AND DEFORMED MARTENSITE PHASE

NITINOL PHASE DIAGRAM

TTT DIAGRAM FOR NITINOL AND DSC SCAN FOR NITINOL

DYNAMIC SURFACE COATING WITH DIFFERENT INNER AND OUTER
SURFACE CHARACTERISTICS

PORE STRUCTURE

PHYSICAL DIMENSIONS OF POROUS COATING

PHYSICAL DIMENSIONS OF POROUS COATING

PHYSICAL DIMENSIONS OF POROUS COATING

THICKNESS OF POROUS COATING

DYNAMIC POROUS COATING FOR ORTHOPEDIC IMPLANT

REFERENCE TO PENDING PRIOR PATENT APPLICATIONS

This patent application:

(i) is a continuation-in-part of prior U.S. patent application Ser. No. 13/764,188, filed Feb. 11, 2013 by Matthew Fonte et al. for POROUS COATING FOR ORTHOPEDIC IMPLANT UTILIZING POROUS, SHAPE MEMORY MATERIALS, which patent application claims benefit of prior U.S. Provisional Patent Application Ser. No. 61/596,900, filed Feb. 9, 2012 by Matthew Fonte et al. for POROUS, SHAPE MEMORY MATERIAL, ORTHOPEDIC IMPLANT COATING;

(ii) claims benefit of prior U.S. Provisional Patent Application Ser. No. 61/612,496, filed Mar. 19, 2012 by Matthew Fonte et al. for POROUS, SHAPE MEMORY MATERIAL, ORTHOPEDIC IMPLANT COATING;

(iii) claims benefit of prior U.S. Provisional Patent Application Ser. No. 61/661,086, filed Jun. 18, 2012 by Matthew Fonte et al. for "DYNAMIC" ORTHOPEDIC COATINGS MADE OF SPACER FABRIC; and (iv) claims benefit of prior U.S. Provisional Patent Application Ser. No. 61/738,574, filed Dec. 18, 2012 by Matthew Fonte et al. for POROUS, SHAPE MEMORY MATERIAL, ORTHOPEDIC IMPLANT COATING.

The five (5) above-identified patent applications are hereby incorporated herein by reference.

FIELD OF THE INVENTION

This invention relates to medical apparatus and procedures in general, and more particularly to porous coatings for orthopedic implants.

BACKGROUND OF THE INVENTION

Femoral stems with reduced stiffness have been introduced in total hip arthroplasty to facilitate proximal load transfer and thereby reduce stress shielding and periprosthetic bone loss. However, poor implant fixation and unacceptably high revision rates are a major problem with these prostheses. One reason for this is that the implant is precisely machined and the femoral canal is frequently not, leaving gaps as large as 0.025" between the implant and the wall of the femoral canal. In many instances the implants may only have 35% of their surface area in direct contact with the adjacent bone. See FIG. 1. This lack of a tight fit between the implant and the surrounding bone is a significant problem, inasmuch as a tight fit is required between the implant and the adjacent bone in order to provide maximum fixation in the shortest time, by maximizing implant stability and the opportunity for bone ingrowth.

For successful implants, sufficiently regenerated bone fills the gap between the implant and the host bone, so that the implant is firmly attached to the surrounding bone.

To overcome problems with implant loosening, implants need to stimulate rapid bone regeneration in order to replenish the missing bone and/or to fix the implant firmly within the host bone. To succeed as an orthopedic implant, the implant must provide a habitat for bone-forming cells (e.g., osteoblasts) so that the bone-forming cells can colonize on the implant surface and synthesize new bone tissue. Frequently the implants are not compatible with the bone cells responsible for bone formation, and instead promote the formation of undesirable fibrous soft tissue. Such fibrous soft tissue does not adequately support the implant, which leads to implant loosening under physiological loading conditions and eventual implant failure. Thus, in order to design more successful orthopedic implants, one needs to take into account the cellular processes that promote bone ingrowth. Positive responses from osteoblasts, including increased initial adhesion, proliferation and differentiation (from noncalcium-depositing cells to calcium-depositing cells) are essential. Coordinating activities between osteoblasts and the bone-resorbing cells (e.g., osteoclasts) is also needed in order to provide healthy bone around the implant. Poor communication between cells can lead to bone necrosis adjacent to the implant, thereby causing loosening of the implant. Another undesirable occurrence is the formation of fibrous soft tissue by fibroblasts. Excessive fibrous soft tissue formation hinders osteoblast/osteoclast activities and hence limits bone regeneration. Due to these cellular events, the orthopedic field has concentrated on understanding cellular recognition of surfaces and creating biomaterial surface properties which maximize such interactions for the creation of more bone and enhanced osseointegration.

One way to improve the performance of bone implants is to modify the surface texture of the implants. Many studies have shown that microstructural features such as grain and particle size promote osteoblast functions better than smooth surfaces. This motivates the use of nanophase materials for orthopedic implants.

Macrostructural features such as porous coatings are another means for improving osseointegration of the implant. Today, hip implant stems are typically a composite structure consisting of a substrate (typically formed out of a cobalt chrome alloy or a titanium alloy) which carries the patient's weight, and a porous surface coating mounted on the implant substrate. This porous surface coating (which is generally referred to in the industry as a "porous coating") comprises peaks and valleys, whereby to aid in immediate implant fixation and ultimately promote long term stability through osseointegration of the host bone with the porous coating. See FIG. 2.

Prior to inserting the implant, the surgeon broaches the femoral canal to create a cavity that, ideally, closely matches the geometry of the implant (which is then inserted into the cavity in the bone). However, this fit is not always perfect, and gaps frequently exist between the implant and the bone. These gaps cause the implant to "point load" the surrounding bone, and also create barriers which inhibit rapid and effective osseointegration of the implant.

Today, the majority of porous coatings are made of titanium or tantalum. These porous coatings are "static", in the sense that they are substantially rigid. These porous coatings are textured, and are applied to the implant substrate by hot plasma spray, chemical and/or physical vapor deposition, by chemically etching thin films and plates, and/or by sintering and/or diffusion bonding metal beads or metal fibers into a solid rigid mass. See FIG. 3.

In addition to producing a substantially rigid structure, the coating processes used to produce porous coatings tend to produce a largely two-dimensional structure for the bone to grow around. There is no means for the bone to tunnel further into the porous coating so as to establish significant three-dimensional osseointegration. Thus, the largely two-dimensional porous coating may stifle or compromise effective long-term osseointegration of the implant due to the lack of significant three-dimensional osseointegration. Additionally, the largely two-dimensional porous coating structures created using these prior art technologies do not accurately mimic the structure of trabecular (i.e., cancellous) bone, which is three-dimensional and includes interconnecting networks of pores with capillarity properties. See FIG. 4.

Recently, there have been advances in the creation of porous coatings that more accurately resemble trabecular bone. These porous coatings have interconnecting networks of pores which are similar to those of trabecular bone, and may serve to promote bone ingrowth deeper into the porous coating and hence provide better long-term implant fixation. One method known in the art for creating such a porous coating is through the replication of an open cell network. In this method, a structure similar to trabecular bone (e.g., a polyurethane foam) is coated with another material (e.g., titanium or tantalum) by vapor deposition, low temperature arc vapor deposition (LTAVD), chemical vapor deposition, ion beam assisted deposition and/or sputtering. The underlying structure (e.g., the polyurethane foam) may then undergo pyrolysis so as to remove the underlying structure (e.g., the polyurethane foam), leaving a metallic structure which can be attached to the hip implant substrate (e.g., by sintering, brazing, diffusion bonding, gluing or cementing, etc.). See FIG. 5. However, the porous coating produced by this method is static, i.e., it is substantially rigid.

Other methods for forming a porous coating include chemical vapor deposition of commercially pure tantalum onto a porous carbon scaffold and then sintering the resulting structure onto the substrate of the implant. See FIGS. 6 and 7. Again, however, the porous coating produced by this method is static, i.e., it is substantially rigid.

Depending on the desired thickness of the struts of the porous coating, the physical or chemical vapor deposition process may be sufficient to reproduce the scaffold structure; however, it is also possible to more rapidly thicken the struts following deposition through the bulk application of a powdered metal or granulates made of titanium, tantalum or other biomaterials, with or without a binder (e.g., methylcellulose). Following the application of the powdered metal, the scaffold is sintered to integrate the powder or granulates. See FIG. 8. In any case, however, the porous coating produced by this method is static, i.e., it is substantially rigid.

SUMMARY OF THE INVENTION

The primary purpose of the present invention is to improve the performance of implants by creating an implant with a dynamic porous coating that changes shape, either through expansion or lateral movement, so as to fill a gap with adjacent bone and to apply pressure against adjacent bone. The dynamic porous coating is flexible, and expands to apply controlled pressure against the adjacent bone, promotes bone remodeling, improves fixation through faster osseointegration and reduces the gaps between the implant/bone interface.

The dynamic porous coating of the present invention preferably comprises shape memory materials which are less stiff than titanium 6al-4v and cobalt-chrome alloys. These shape memory materials can include Nitinol, near beta or fully beta titanium alloys, shape memory polymers (e.g., thermoplastic block copolymers) and biodegradable shape-memory polymer systems, all of which can be processed to be either superelastic or to have shape recovery characteristics. These dynamic porous coatings have a 2D or 3D porous structure which can be multi-layered, and may cover the implant either partially or entirely. The pores of the dynamic porous coatings can be infiltrated with a mixture of hydroxyapatite, tricalcium phosphate and/or other bone-making agents known in the art so as to further promote osseointegration. The dynamic porous coatings of the present invention can be made primarily of shape memory materials and augmented with non-shape memory materials to help control strength, stiffness, biocompatibility and pore size for optimal osseointegration properties. The present invention finds utility as a dynamic porous coating in a wide range of orthopedic implants where fixation and osseointegration are desirable, e.g., hip implants, knee implants, shoulder implants, elbow implants, spinal implants, extremity implants, dental implants, cranial and maxillofacial implants, etc. (sometimes hereinafter referred to simply as "implants").

Significantly, the dynamic, space-filling, porous coating of the present invention has the ability to fill the gaps which frequently occur when seating the implant in a broached bone hole, and thus more evenly load the surrounding bone and increase the capacity for fast and effective osseointegration. As a result, the dynamic, space-filling, porous coatings of the present invention have particular utility in revision surgery (e.g., in hip revision surgery) where, after a prior prosthesis has been removed from bone, the bone cavity may be irregular and hence problematic gaps may be more likely to occur around the replacement implant.

In one preferred form of the present invention, there is provided a dynamic porous coating for an orthopedic implant, wherein the dynamic porous coating is adapted to apply an expansive force against adjacent bone so as to fill gaps between the dynamic porous coating and adjacent bone and to create an interference fit between the orthopedic implant and the adjacent bone.

In another preferred form of the present invention, there is provided an orthopedic implant comprising a substrate and a dynamic porous coating secured to the substrate, wherein the dynamic porous coating is adapted to apply an expansive force against adjacent bone so as to fill gaps between the dynamic porous coating and adjacent bone and to create an interference fit between the orthopedic implant and the adjacent bone.

In another preferred form of the present invention, there is provided a method for providing therapy to a patient, the method comprising:

providing an orthopedic implant comprising a substrate and a dynamic porous coating secured to the substrate, wherein the dynamic porous coating is adapted to apply an expansive force against adjacent bone so as to fill gaps between the dynamic porous coating and adjacent bone and to create an interference fit between the orthopedic implant and the adjacent bone;

inserting the orthopedic implant into a bone cavity in the patient so that the dynamic porous coating applies an outward force against adjacent bone so as to fill gaps between the dynamic porous coating and adjacent bone and to create an interference fit between the orthopedic implant and the adjacent bone.

In another preferred form of the present invention, there is provided a dynamic porous coating for an orthopedic implant, the dynamic porous coating comprising:

a spacer fabric comprising:
an inner layer formed by fibers;
an outer layer formed by fibers;
the outer layer being spaced from the inner layer; and
the outer layer being connected to the inner layer by a plurality of connecting fibers extending between the inner layer and the outer layer, such that the outer layer is capable of applying an outward force against adjacent bone.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
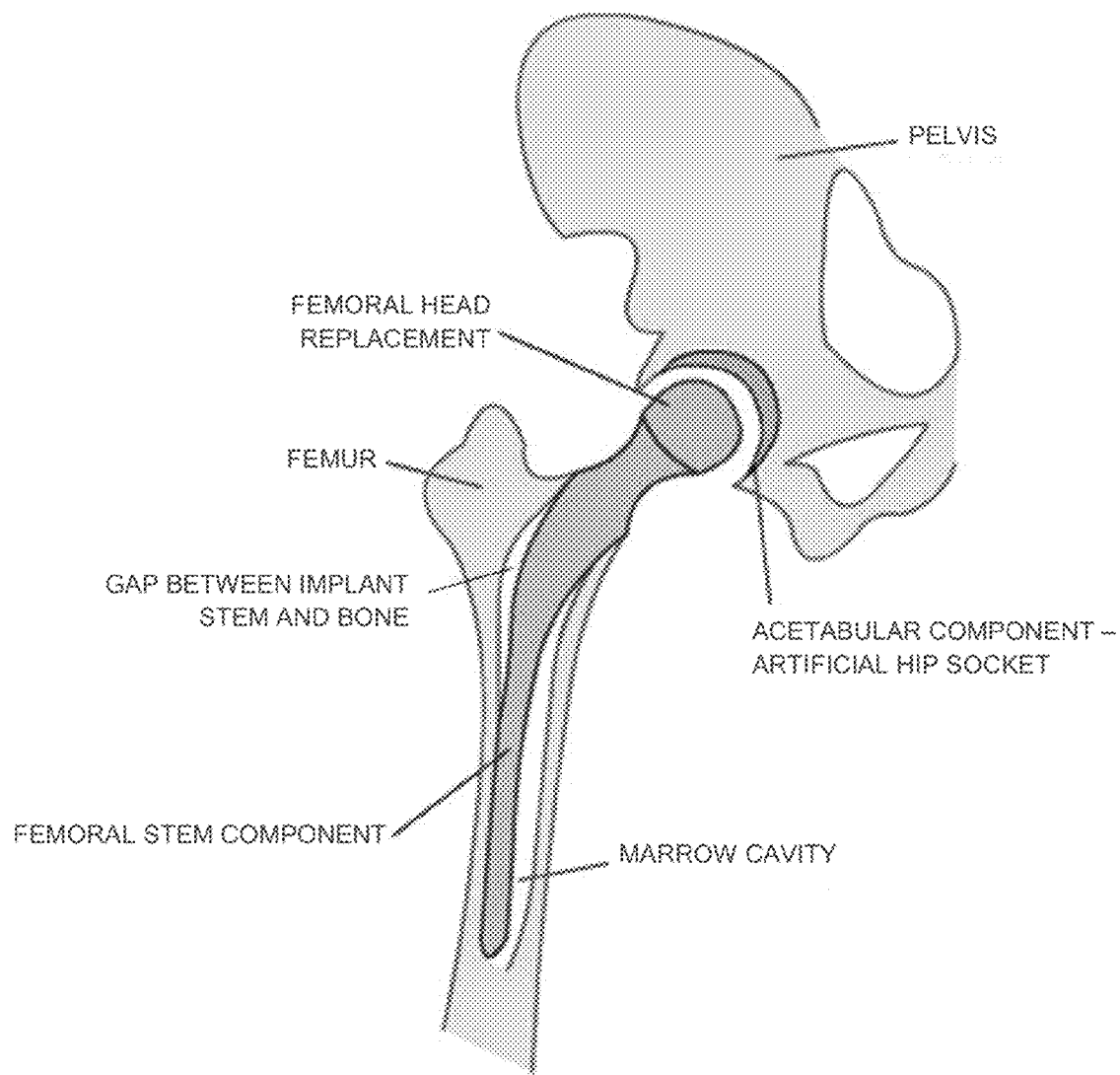
FIG. 1 is a schematic view showing gaps between an implant surface and bone.
Figure 2:
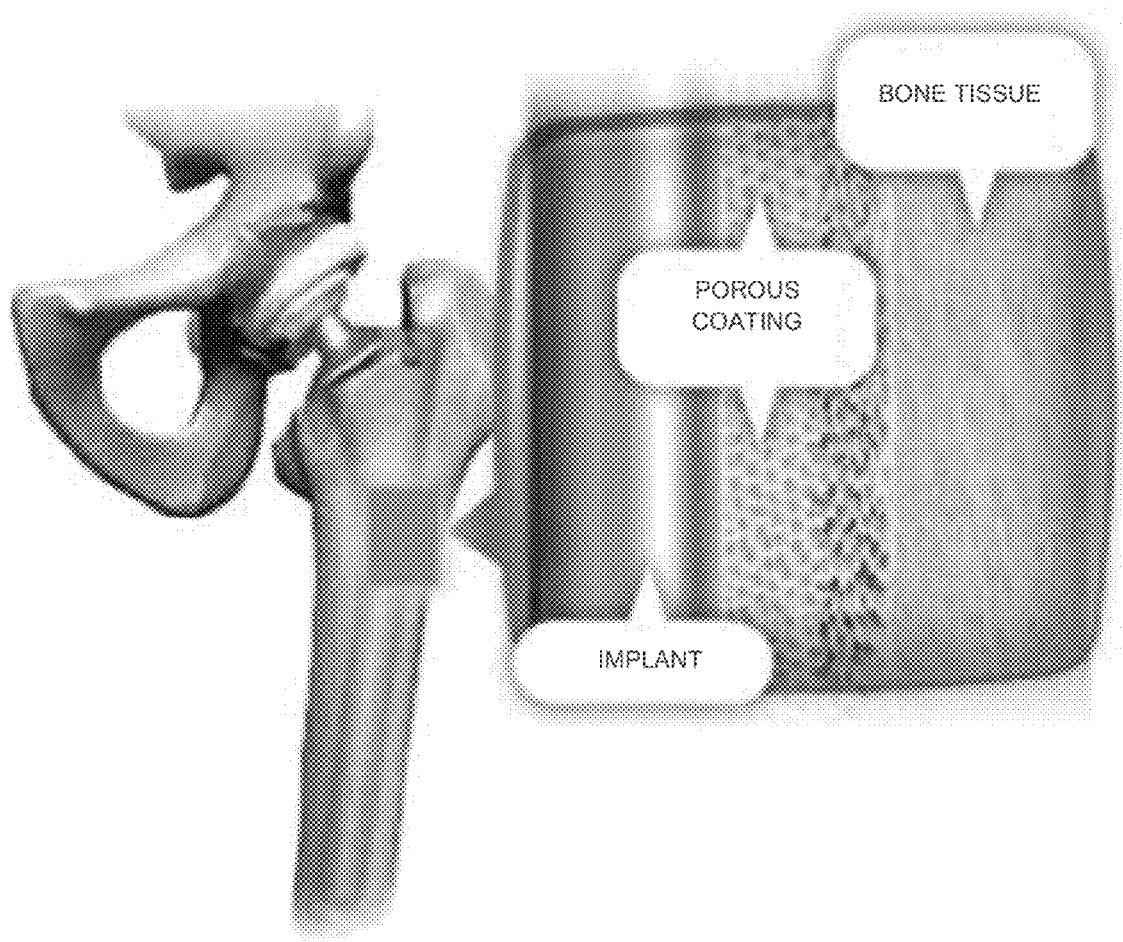
FIGS. 2 and 3 are schematic views showing static porous coatings of the prior art.
Figure 3:
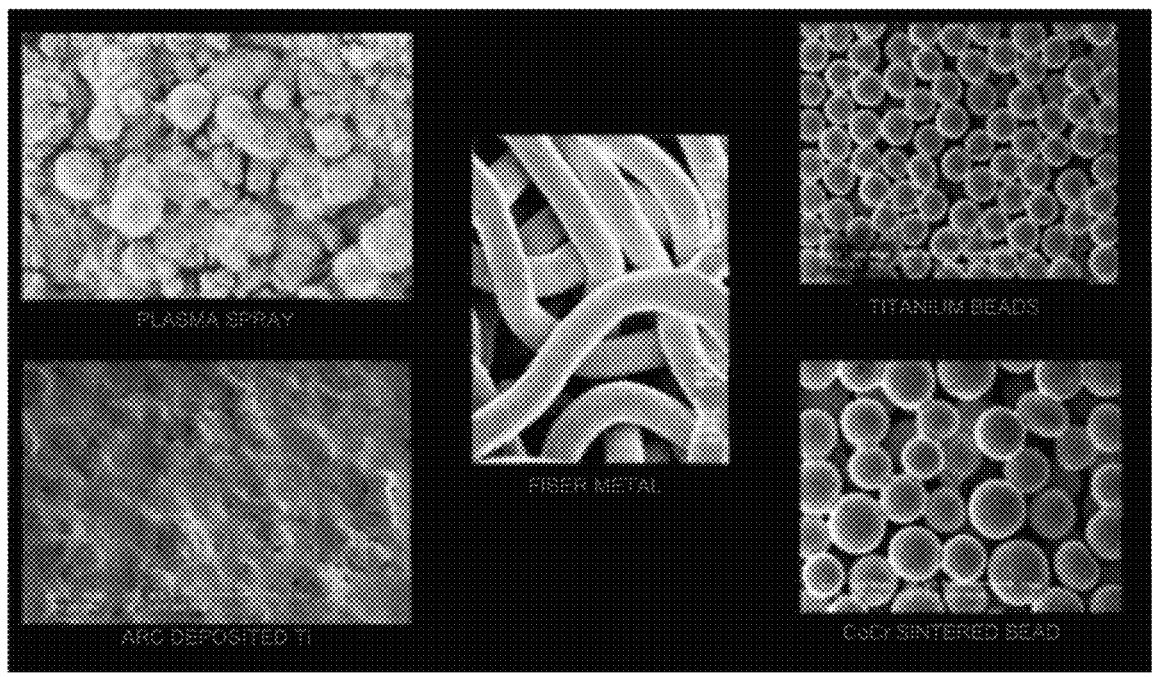
Figure 4:
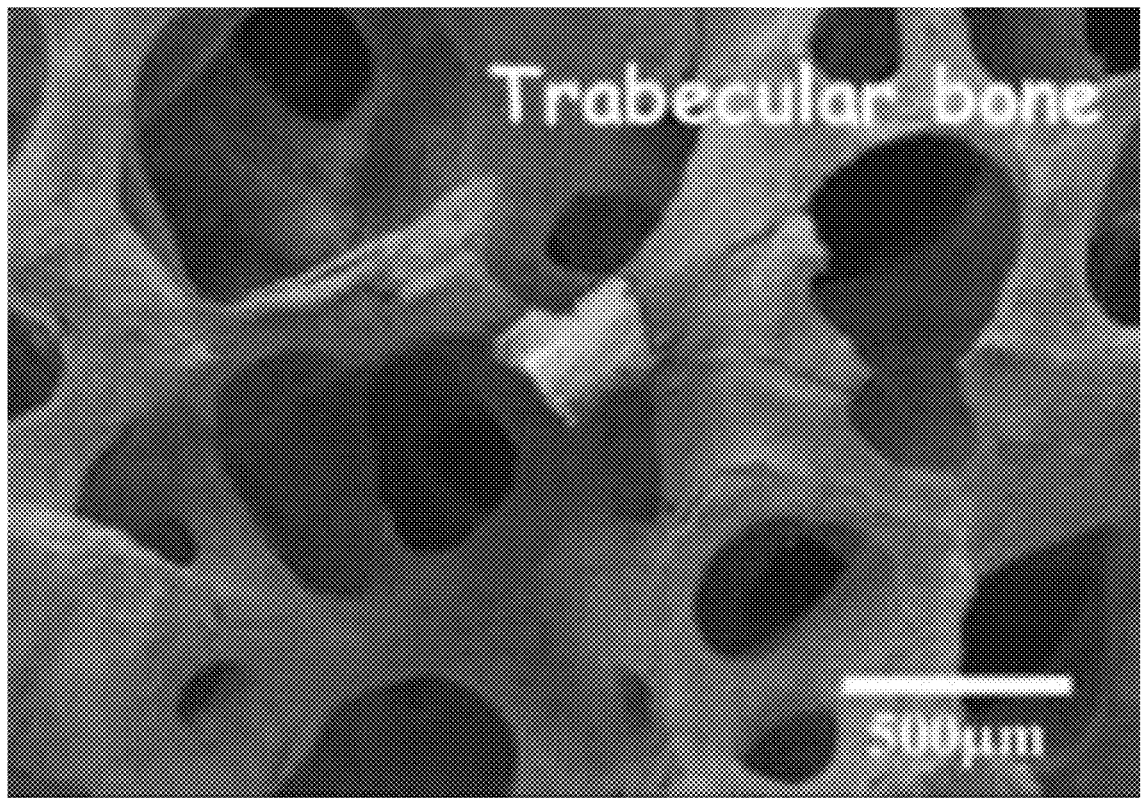
FIG. 4 is a schematic view showing the structure of trabecular bone.
Figure 5:
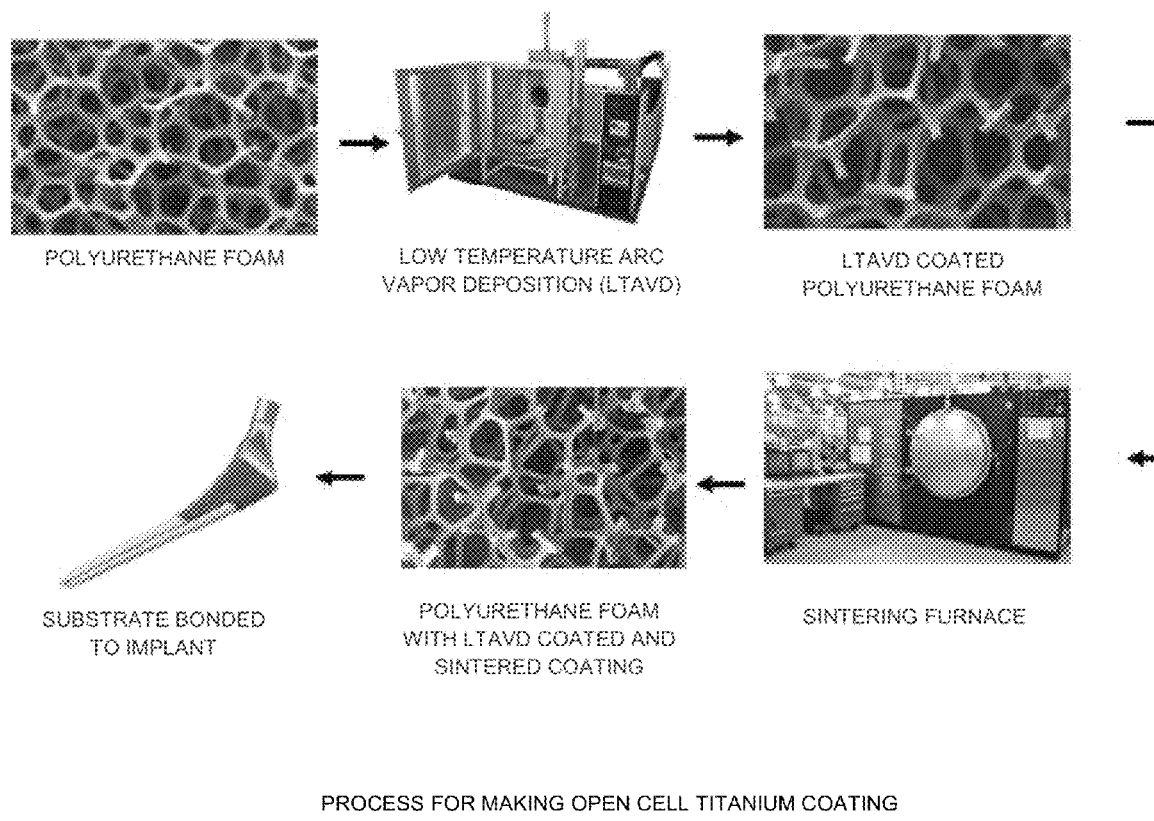
FIGS. 5-7 are schematic views showing prior art processes for forming a static porous coating.
Figure 6:
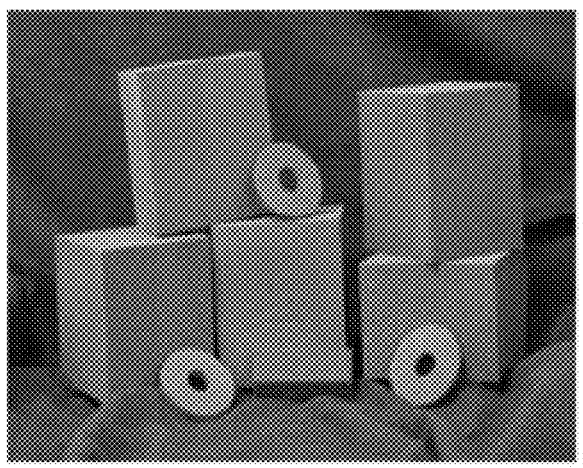
Figure 7:
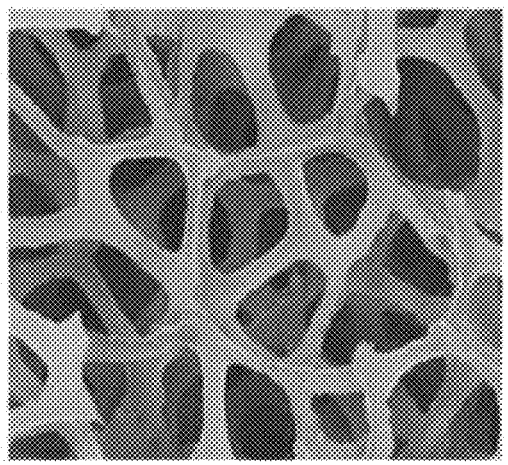
Figure 8:
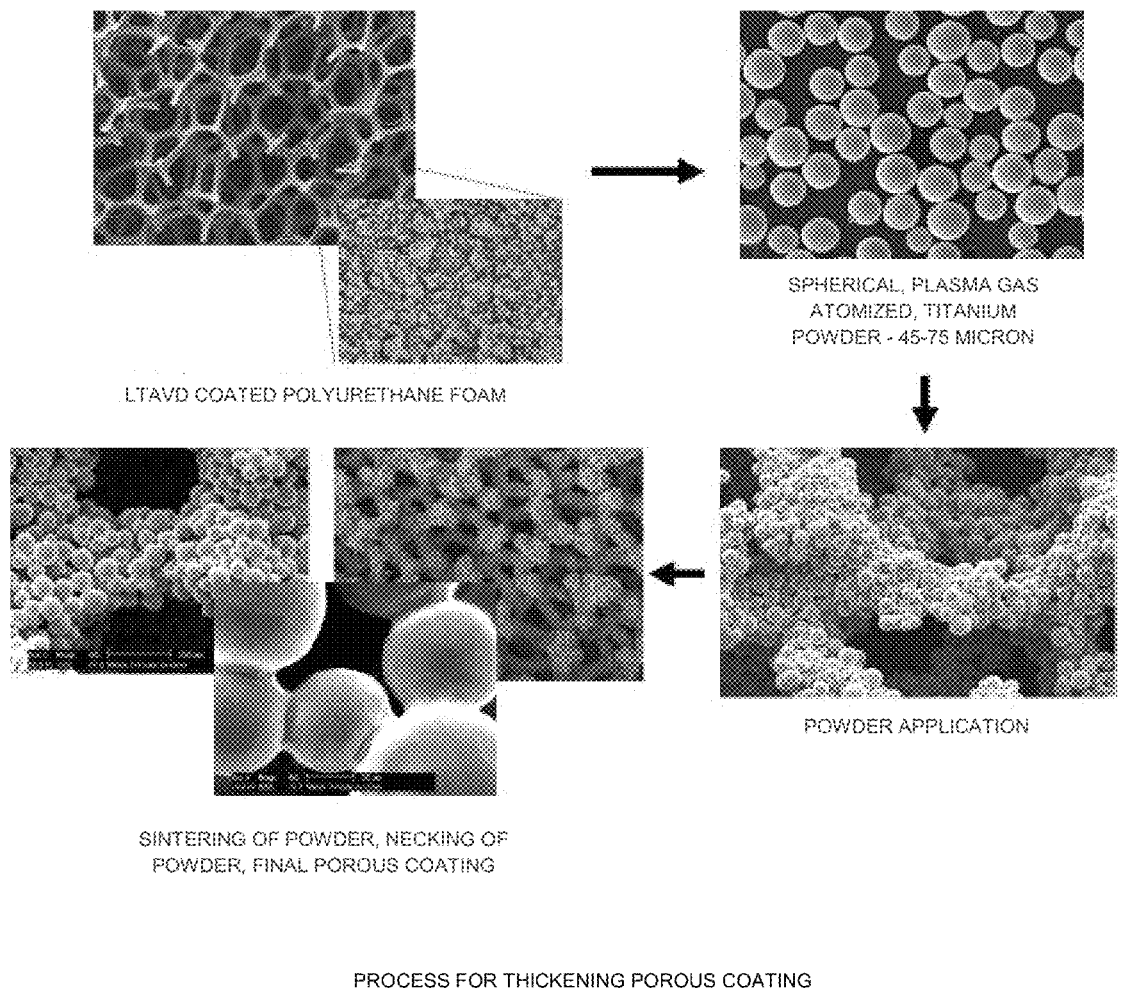
FIG. 8 is a schematic view showing processes for thickening a static porous coating.

As noted above, prior art porous coatings are static (i.e., rigid) structures, fixed in shape and geometry, which limits their ability to infiltrate the bone tissue. As such, bone tissue must infiltrate into the porous coating in order to achieve some level of osseointegration. With prior art porous coatings, initial osseointegration is limited to those regions where the porous coating is in direct contact with the bone surface. Initial osseointegration is not possible where a gap exists between the implant and the bone, which is frequently the case in practice.

In contrast, the present invention provides a porous coating which is dynamic in nature, preferably made out of shape memory materials (SMM), e.g., Nitinol (NiTi) per ASTM F2063, Ti-13Nb-13Zr per ASTM F1713, Ti-12Mo-6Zr-2Fe (TMZF) per ASTM F1813, etc. The dynamic porous coating of the present invention expands against, and applies strain against, the host bone so as to stimulate bone remodeling and expedite/enhance osseointegration. The dynamic porous coating of the present invention is designed to be "space filling" in nature, increasing the surface area of the implant that is in direct contact with the bone surface. Thus, the dynamic porous coating of the present invention applies bone-building strain against the bone tissue and, in the process, also infiltrates into the bone tissue, thereby providing true three-dimensional osseointegration.

Biomedical applications are intended to be the main applications for the dynamic porous coatings of the present invention. The dynamic porous coatings are preferably formed out of shape memory materials (SMM). SMM porous coatings offer the following advantageous properties: (i) good biocompatibility; (ii) a combination of high strength (which is important to prevent deformation or fracture), relatively low stiffness (which is useful to minimize stress shielding effects) and high toughness (which is essential to avoid brittle failure); (iii) a porous scaffold for bony ingrowth; and (iv) shape-recovery behavior facilitating implant insertion and ensuring good mechanical contact with the host bone, whereby to provide mechanical stability and enhanced osseointegration.

The dynamic porous coating of the present invention, which is preferably made of a shape memory material, can be produced by any appropriate method, however, it is presently preferred that the porous coating be produced using one of five methods:

(i) replication of a porous trabecular analog structure by coating foam (or a carbon foam) structure;
(ii) wire knitting, weaving, or braiding;
(iii) honeycomb- or truss-based structures;
(iv) sintered beads; and
(v) lamination of multiple layers, as will hereinafter be discussed in further detail.

The dynamic porous coating of the present invention can be produced as a sheet or shell that can be wrapped or placed over an implant substrate and then secured to the implant substrate, either by mechanically attaching it to the implant substrate, dynamically contracting it to adhere to the implant substrate and/or by metallurgically attaching it to the implant substrate (e.g., by braising, welding, sintering, diffusion bonding, hot isostatic pressing, etc.).

Figure 9:
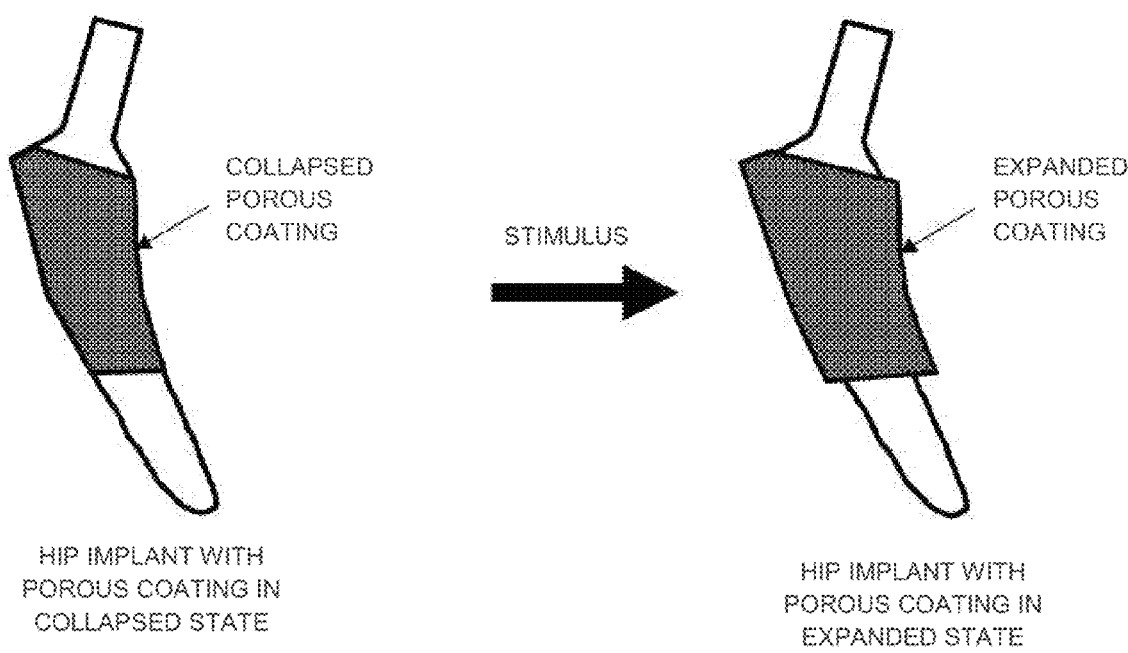
FIG. 9 is a schematic view showing a dynamic porous coating formed in accordance with the present invention.

The SMM porous coating, which is essentially an exoskeleton structure for the implant substrate, can be superelastic (SE), which is capable of restoring its shape once it is unconstrained and made to spring back; and/or it can have shape memory effect (SME) which allows it to be dynamic under the influence of temperature change, e.g., warming from a colder temperature to body temperature, or cooling from a warmer temperature to body temperature. The SMM dynamic porous coating can be "squished" flat and either superelastically, or through SME (temperature change), spring outward once the implant is inserted into the femoral canal (or other bone cavity) so as to apply pressure on the bone tissue and lock the implant in place. See FIG. 9. The dynamic porous coating of the present invention can be applied to implants made of conventional materials such as cobalt-chrome alloys and titanium alloys; or the dynamic porous coating can be applied to implants which are themselves made of a shape memory material such as Nitinol.

Replication of a Porous Trabecular Analog Structure

Figure 10:
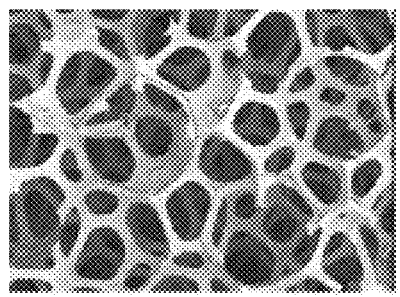
FIGS. 10-14 are schematic views showing various porous coatings formed in accordance with the present invention.
Figure 11:
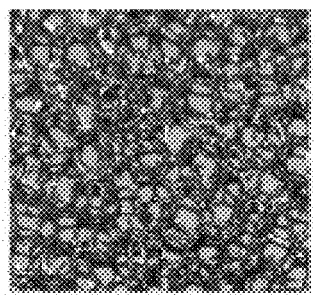
Figure 12:
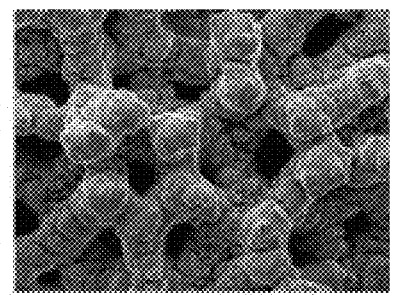

Deposition of shape memory material onto a polyurethane trabecular analog results in a dynamic porous coating having the basic dodecahedron structure of trabecular bone. See FIGS. 10-12.

Figure 13:
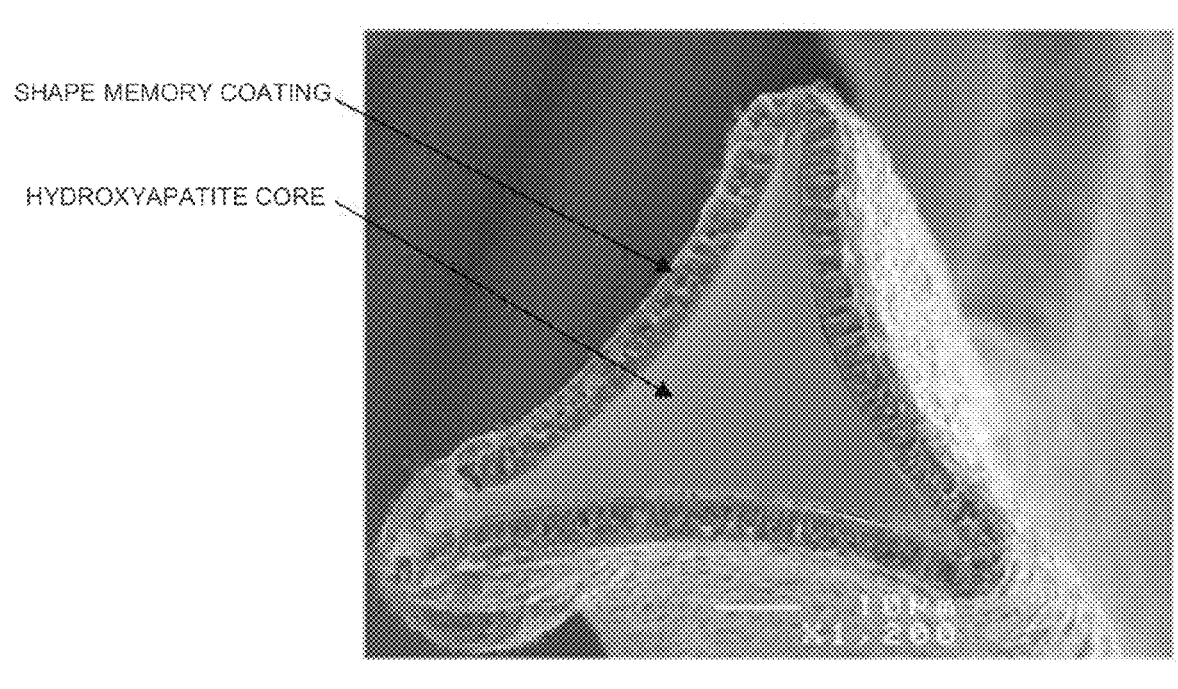

Additionally, the open pore structure of the polyurethane foam can first be reproduced using a slurry of hydroxyapatite (or any other known bone-forming compound), with or without a binder (e.g., methylcellulose or other appropriate binder). This hydroxyapatite slurry is used to coat the surface of the polyurethane foam scaffold (without filling the pores), then it is dried, heated to burn off the polyurethane foam scaffold, and finally sintered. This results in an open cell hydroxyapatite structure which is similar in shape to the initial polyurethane foam. This hydroxyapatite structure can then be used as the trabecular bone analog for creating the shape memory material porous coating, i.e., the hydroxyapatite structure is coated with a shape memory material. By way of example but not limitation, the hydroxyapatite structure can be sputtered with Nitinol, whereby to create a superelastic metal dynamic porous coating with a hydroxyapatite core. Additional processing to the shape memory material/hydroxyapatite scaffold (e.g., providing abrasion to the outer surface) can cause regions of the shape memory material to be selectively removed, thereby exposing the hydroxyapatite core. This exposed hydroxyapatite core is then available to osteoblasts so as to aid in osseointegration of the implant over a prolonged period of time. As the hydroxyapatite is consumed/remodeled, it will leave behind an internal cavity for the bone to grow into. See FIG. 13.

It is also possible to create a comparable structure by using shape memory material powder to either replicate or coat the trabecular analog structure (created from polyurethane foam) instead of using a physical or chemical deposition method. By way of example but not limitation, it is possible to create a porous Nitinol coating using a slurry of either powdered or granulated Nitinol with or without an appropriate binder (e.g., methylcellulose). This shape memory material slurry can be deposited on the surface of the trabecular structure (either polyurethane foam or a hydroxyapatite structure created from the polyurethane foam). The shape memory material slurry is then allowed to dry, whereafter it is sintered to fuse the powdered or granulated particles of Nitinol into an elastic porous structure (i.e., the dynamic porous coating). Alternatively, a slurry of powdered titanium and nickel (in the appropriate proportions) can be deposited on the surface of the trabecular analog scaffold, and then sintered at the appropriate temperature so as to form shape memory Nitinol (and hence to form a dynamic porous coating).

Figure 14:
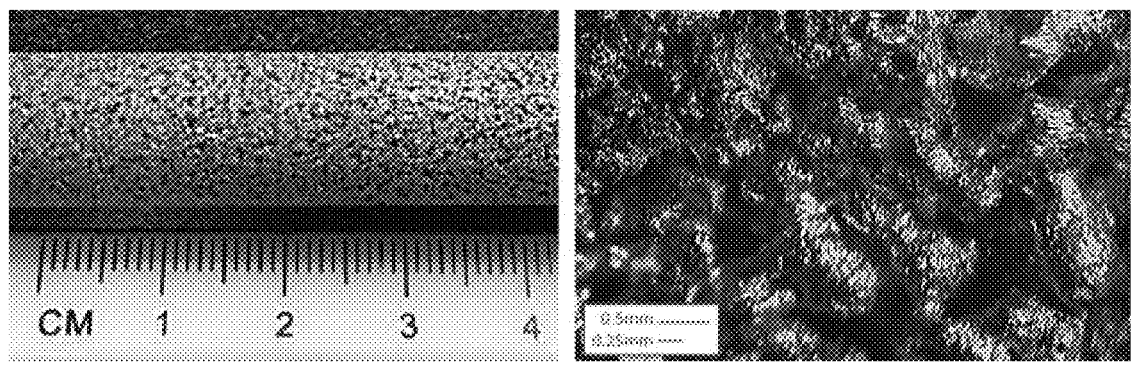

Porous Nitinol structures (i.e., dynamic porous coatings) can also be made by utilizing the so-called self-propagating high-temperature synthesis (SHS) reaction process. In this process, titanium powder is mixed with nickel powder and then compacted so as to form a compact. Energy (typically in the form of a plasma torch or hot filament) is then applied to the compact. Sufficient energy is supplied to the compact to cause the titanium and nickel to form Nitinol. It will be appreciated that when the reaction is complete, a porous Nitinol scaffold (i.e., a dynamic porous coating) has been created. See FIG. 14.

Wire Knitting, Weaving, And Braiding

It is also possible to create dynamic porous structures (i.e., dynamic porous coatings) from shape memory wire. More particularly, many shape memory materials are readily available as wires in a variety of diameters. By way of example but not limitation, some commercially available NiTi and Ti 13Zr-13Nb wires range from 0.0004" to 0.025" thick. Flexibility and overall diameter of the shape memory wire can be increased by braiding or twisting together multiple wires of smaller diameters so as to create larger structures. Additionally, bioabsorbable filaments can be used in conjunction with shape memory filaments to create a dynamic porous coating that can remodel over time, thereby providing a structure with increased initial strength, and having the ability to resorb as new bone grows within the pores of the dynamic porous coating. In addition to filaments and wires, tubes can be used for forming the dynamic porous coating. The tubes may have a plurality of radial holes to facilitate bony ingrowth. If desired, these tubes can be filled hydroxyapatite or other bone-forming substances so as to aid in osseointegration.

Figure 15:
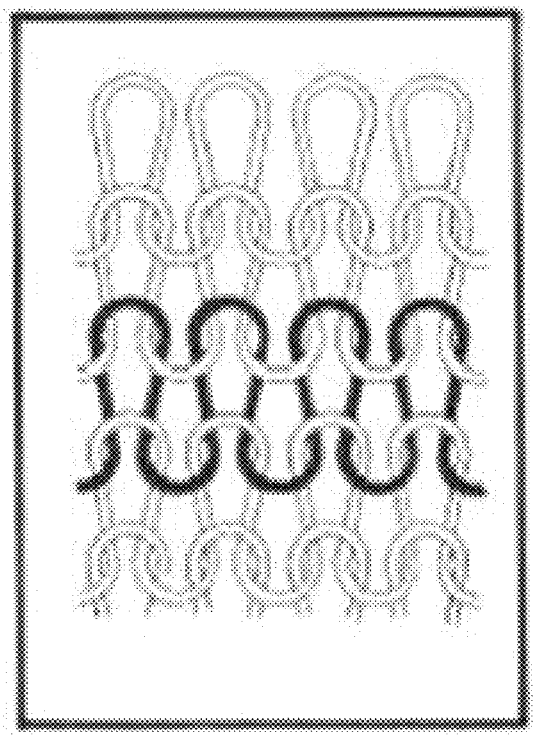
FIGS. 15 and 16 are schematic views showing various forms of knitting.
Figure 16:
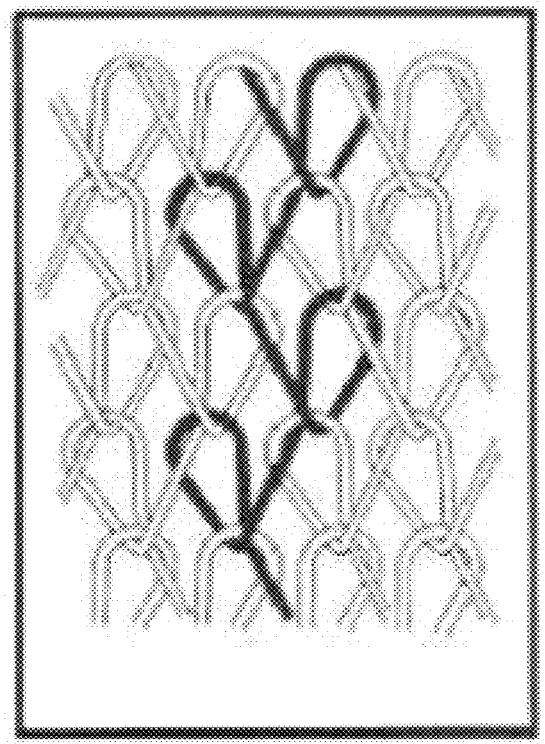
Figure 17:
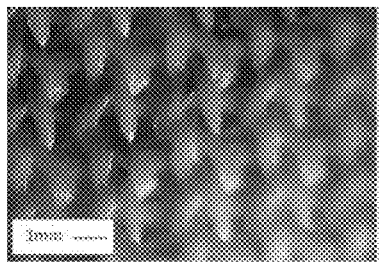
FIGS. 17-19 are schematic views showing dynamic porous coatings formed by knitting.
Figure 18:
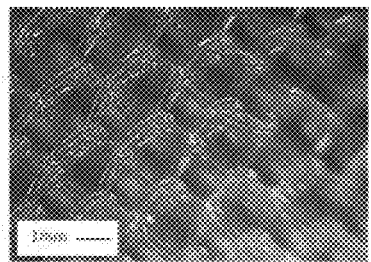
Figure 19:
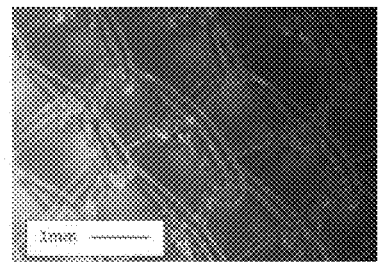

Knit structures, with their high number of individual fibers, allow for the creation of very intricate porous patterns, and hence provide the opportunity for increased performance capabilities for the dynamic porous coating. Warp and weft are two different types of knitting which may be used to form a dynamic porous coating. Warp knits have fibers that extend along the length of the material, while weft knits have fibers that extend across the width of the material. See FIGS. 15 and 16. Knits can be created in either sheets or tubes. Multiple sheets can be laminated on top of one another, and tubes can be formed concentric to one another, in order to achieve a more three-dimensional structure for the dynamic porous coating. In addition, by laminating sheets or tubes with different porosities, a more complex overall pore structure can be created for the dynamic porous coating. See FIGS. 17-19.

In one preferred form of the invention, shape memory material fibers are knit into a highly porous, highly elastic "spacer fabric" which then serves as the dynamic porous coating. More particularly, and looking now at FIGS. 20 and 20A-20D, the shape memory material spacer fabric comprises two opposing faces which are separated from one another, but which are also interconnected to one another with filaments which extend between the two faces and fill the region therebetween, providing an elastic cushion between the two faces. The two opposing faces of the spacer fabric can have the same or different mesh sizes, with surface pores of various geometries including, but not limited to, honeycombs and rhomboids. The length of the wire filaments extending between the two faces (i.e., the connecting filaments which fill the space between the two faces) can be varied as desired so as to adjust the thickness and spring factor of the overall spacer fabric material. The shape memory material spacer fabric can be formed as a sheet or strip that can be wrapped around the implant, or as a sleeve that can be slid over the implant, whereby to form the desired dynamic porous coating for the implant. The shape memory material spacer fabric can then be sintered to the implant stem prior to aging and shape-setting.

Among other things, the shape memory material spacer fabric of the present invention provides a dynamic porous coating for an implant that expands and applies controlled, chronic pressure against the bone, promotes long term bone remodeling, improves secondary fixation through faster osseointegration and reduces the gaps between the implant/bone interface which can inhibit proper osseointegration. In one preferred form of the invention, the new dynamic porous coating is formed out of a spacer fabric comprising Nitinol fibers (i.e., Nitinol wires) which are woven in an appropriate manner so as to form the overall spacer fabric construct. In this form of the invention, the SMM spacer fabric preferably comprises two separate fabric faces which are knitted independently of one another and then connected by filaments which extend between the two separate fabric faces and fill the space therebetween, whereby to provide the spring factor of the overall spacer fabric. See FIG. 20A. These nonwoven fabrics can be produced on both circular and flat knitting machines. They may be produced as a flat sheet, or as a cylindrical tube.

Spacer fabrics have three distinct layers. See FIGS. 20A, 20B and 20C. When used as a porous coating for an implant, the three layers of the spacer fabric have three different functions, i.e., the top layer provides for bone ingrowth, the middle (vertical) fiber layer provides for elasticity, and the bottom layer provides for brazing to the implant. The top layer of the spacer fabric can have a structure of repeating dodecahedrons, i.e., a honeycomb geometry similar to that of cancellous bone, whereby to facilitate osseointegration. The bottom layer of the spacer fabric can be engineered so as to facilitate braising to the implant. The middle (vertical) connecting layer of the spacer fabric, which comprises the fibers which extend between the top layer of the spacer fabric and the bottom layer of the spacer fabric and provide spring, is continuous and is knit vertical (e.g., at an angle of 30°-150°) from the top and bottom layers. See FIG. 20C. Thus, the spacer fabric is three-dimensional in construction, and it is the vertical fibers that create the elastic response for the spacer fabric when the spacer fabric is compressed, and/or made to bend, and then allowed to recover. The three ply structure of the spacer fabric has good breathability, wettability, crush resistance, and a 3D porous appearance, which makes it ideal for use as a dynamic porous coating. Each layer of the spacer fabric can be made of different materials and have different porosity levels and geometry. These spacer fabrics can be stacked one on top of another to form a multi-level spacer fabric construct.

The spacer fabric can be designed to have an overall porosity ranging from 45% to 98%, with pore sizes ranging from 100-600 microns (0.004-0.02 inch), with an average of 300 microns (0.01 inch), whereby to facilitate its use as a dynamic porous coating. See FIG. 20D. The modulus of elasticity of the spacer fabric can be engineered so as to have a modulus of elasticity of between 0.1 GPa and 5 GPa, with a desired modulus of elasticity approaching 1.6 GPa (230 ksi), which can be highly beneficial when the spacer fabric is used to form a dynamic porous coating. Significantly, due to the inherent nature of a spacer fabric, the modulus of elasticity of the spacer fabric can vary according to the degree of compression imposed on the spacer fabric, i.e., when the spacer fabric has relatively little compression imposed on it, it will have a relatively low modulus of elasticity, whereas when the spacer fabric has a large compression imposed on it, it will have a relatively high modulus of elasticity. The surface roughness can be generated from either the basic knit structure of the SMM wires crossing over each other, or can be enhanced with a plasma sprayed surface to an average 2500 Ra, which is much coarser than that of conventional porous materials. The plasma spray can be used to stiffen the construct and control pore size.

A "scratch-fit" between the dynamic porous coating and the cortical bone during implant insertion is desirable. This scratch-fit action causes the rough surface of the implant to scrape the walls of the femoral canal, filling the small pores of the dynamic porous coating with bone and providing excellent initial stability. The spacer fabric can be plasma sprayed for increased surface roughness.

In one preferred form of the invention, the dynamic porous coating is fabricated out of shape memory materials so as to provide a porous coating of maximum elasticity. However, it should also be appreciated that the aforementioned three-layer spacer fabrics are deliberately designed to be elastic, i.e., the material can be compressed and, upon removing the compressive force, return to its original geometry. Thus, dynamic spacer fabrics suitable for the present invention can be manufactured using a wide variety of metallic and non-metallic fibers, including non-shape memory material fibers, provided that the fibers are biocompatible and can provide the requisite spring factor for the spacer fabric.

Thus, the dynamic porous coating of the present invention may comprise a spacer fabric formed out of non-shape memory materials such as stainless steel, cobalt chrome alloys, titanium, tantalum, niobium, zirconium alloys, etc.

In one preferred form of the invention, the dynamic porous coating comprises a spacer fabric formed out of shape memory materials such as binary and ternary Nitinol (nickel-titanium). Such shape memory materials have been shown to be biocompatible metals, and are routinely used for medical implants. These materials can be drawn into wire, and used as the starting material for the spacer fabric. Among other things, the following shape memory materials may be used to form the spacer fabric used to form the dynamic porous coating.

| Alloy Designation | ASTM Standard | Elastic Modulus (GPa) | Ultimate Tensile Strength (MPa) |
|---|---|---|---|
| Ti-6Al-4V ELl | F 136 | 98 | 860 |
| Ti-6Al-4V | F 1472 | 110 | 930 |
| Ti-6Al-7Nb | F 1295 | 99 | 900 |
| Ti-15Mo | F 2066 | 77 | 690 |
| Ti-13Nb-13Zr | F 1713 | 64 | 550 |
| Ti-12Mo-6Zr-2Fe | F 1813 | 74 | 931 |

Alternatively, the dynamic porous coating may comprise a spacer fabric manufactured out of biocompatible polymers, including shape memory polymers. These polymers may include one or more of the following:
Polyethylene Terephthalate (PET)
Polypropylene (PP)
Polyetheretherketones (PEEK)
High-performance polyethylenes (UHMWPE)
Bioabsorbable polymers
    Polyglycolic acid (PGA)
    Poly-L-lactide (PLLA)
    Polycaprolactone (PCL)
    Various copolymers
Shape memory polymers
    Polyurethanes
    Block copolymer of polyethylene terephthalate (PET) and polyethyleneoxide (PEO)
    Block copolymers containing polystyrene and poly(1,4-butadiene)
    Triblock copolymer made from poly(2-methyl-2-oxazoline) and polytetrahydrofuran
    Polyetheretherketones (PEEK)

The diameter of the starting fiber greatly determines the mechanical properties of the final spacer fabric structure. Thicker fibers result in a stiffer final construct. Preferably, the diameter of the fiber is between about 0.01 inch and 0.0002 inch. Most preferably, the fiber is between about 0.007 inch and 0.003 inch.

As noted above, the spacer fabric has three distinct layers. These three distinct layers can be manufactured using three distinct wire sizes. As an example, it is possible to use a large wire size for the base of the material so as to increase the surface area available for bonding to the implant, a medium wire size for the filler material (i.e., the connecting fibers) in order to give the spacer fabric appropriate stiffness and elasticity, and a fine wire size for the top surface (i.e., the surface contacting the bone) so as to better match the cancellous bone structure.

As noted above, while spacer fabrics manufactured from conventional materials are dynamic in nature, and hence may be used to form the porous coating of the present invention, the dynamic effect of the spacer fabric can be enhanced by using a shape memory material (SMM), e.g., Nitinol (NiTi) per ASTM F2063, to form the spacer fabric (and hence to form the dynamic porous coating). The SMM porous coating can be superelastic, (SE) which allows it to restore its shape once it is unconstrained, and/or it can have shape memory effect (SME) which allows it to be dynamic under the influence of temperature change, i.e., body temperature. As an example of an SME application, the dynamic porous coating of the present invention can be in the compressed state at a temperature below body temperature (37° C.), and following implantation to the medullary canal, warm to body temperature and return to its original uncompressed shape. This will fill any voids between the implant and the bone, and where constrained, apply chronic bone-building strain to the bone.

Figure 20:
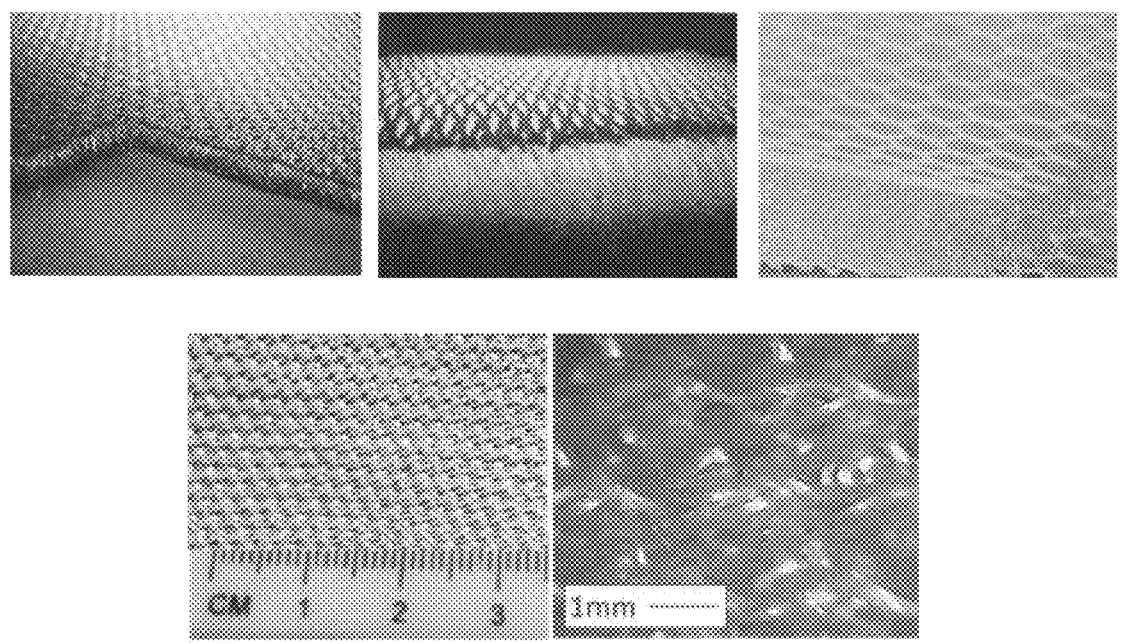
FIGS. 20 and 20A-20G are schematic views showing a dynamic porous coating formed out of spacer fabric.
Figure 20A:
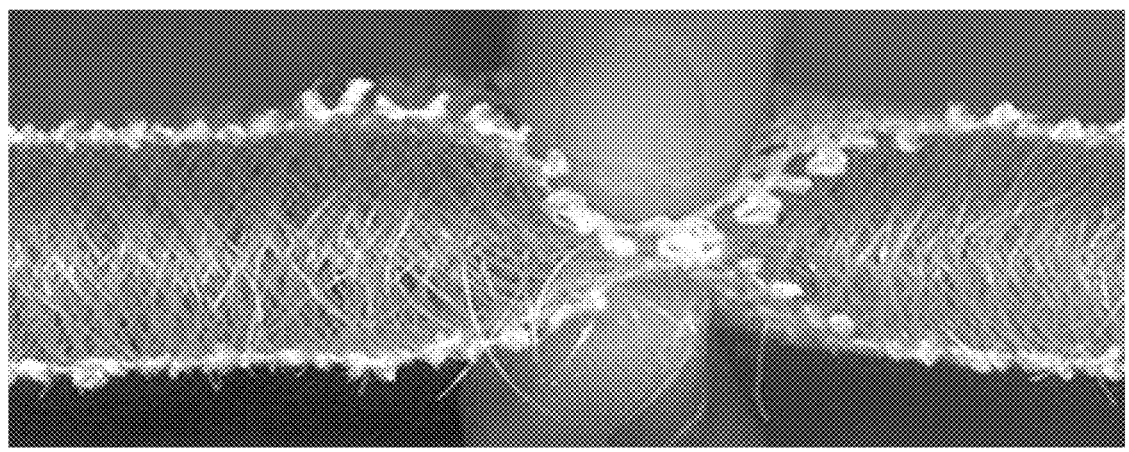
Figure 20B:
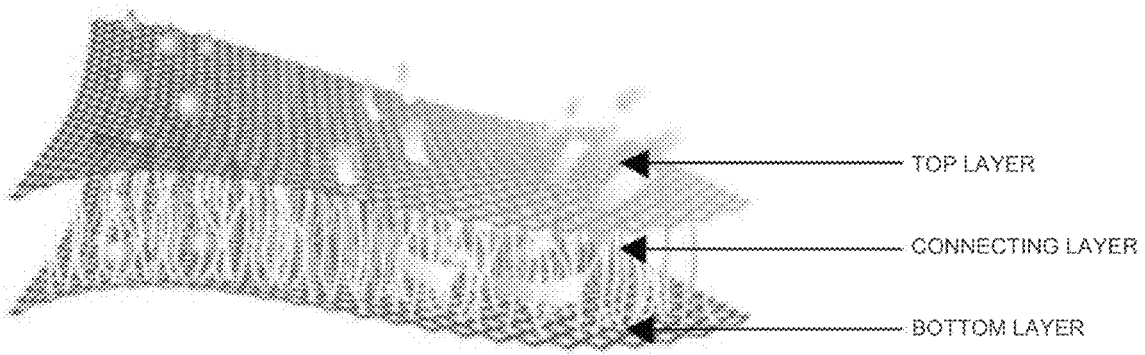
Figure 20C:
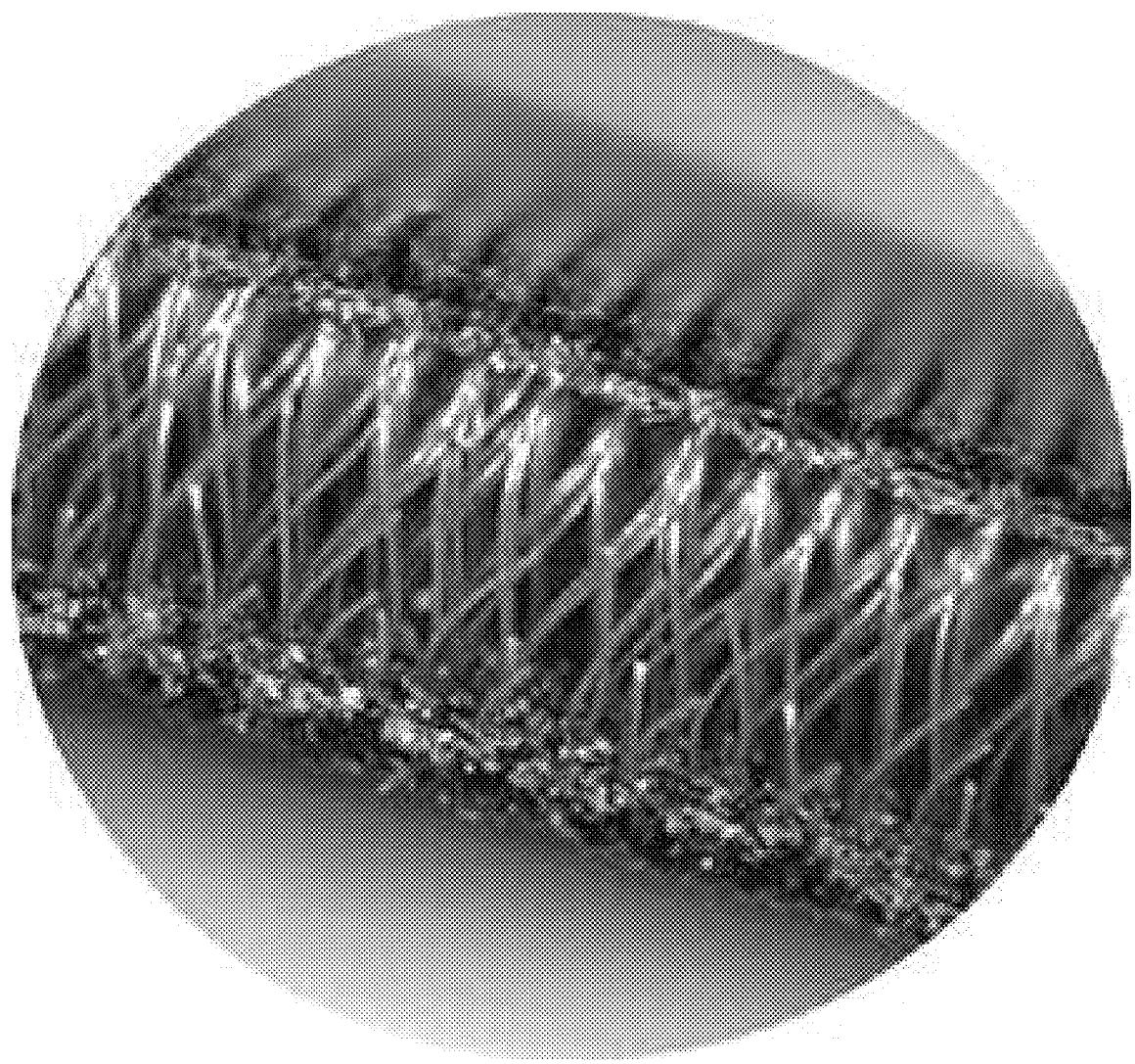
Figure 20D:
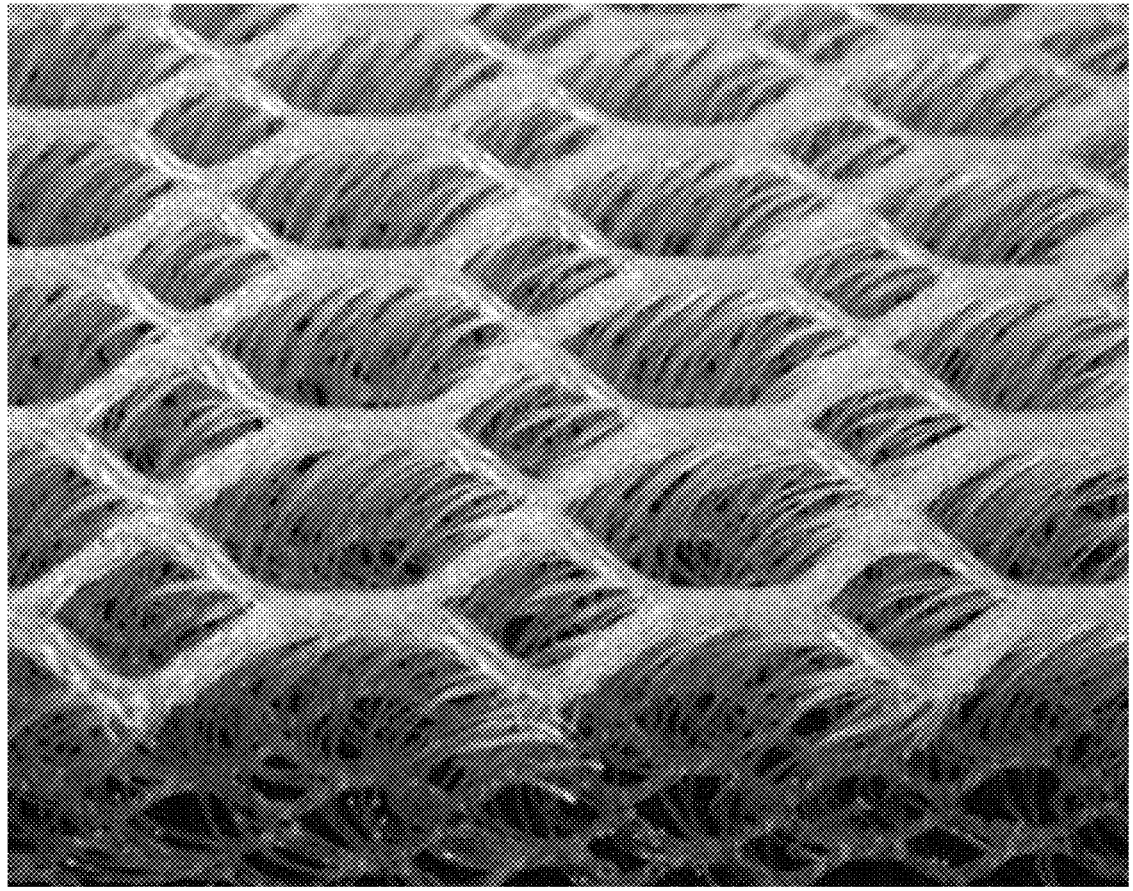
Figure 20E:

FIG. 20E shows exemplary orthopedic implants (e.g., the stem of a femoral hip implant, the cup of an acetabular hip implant, and the femoral component of a knee implant), with a dynamic porous coating formed out of shape memory material spacer fabric.

Figure 20F:
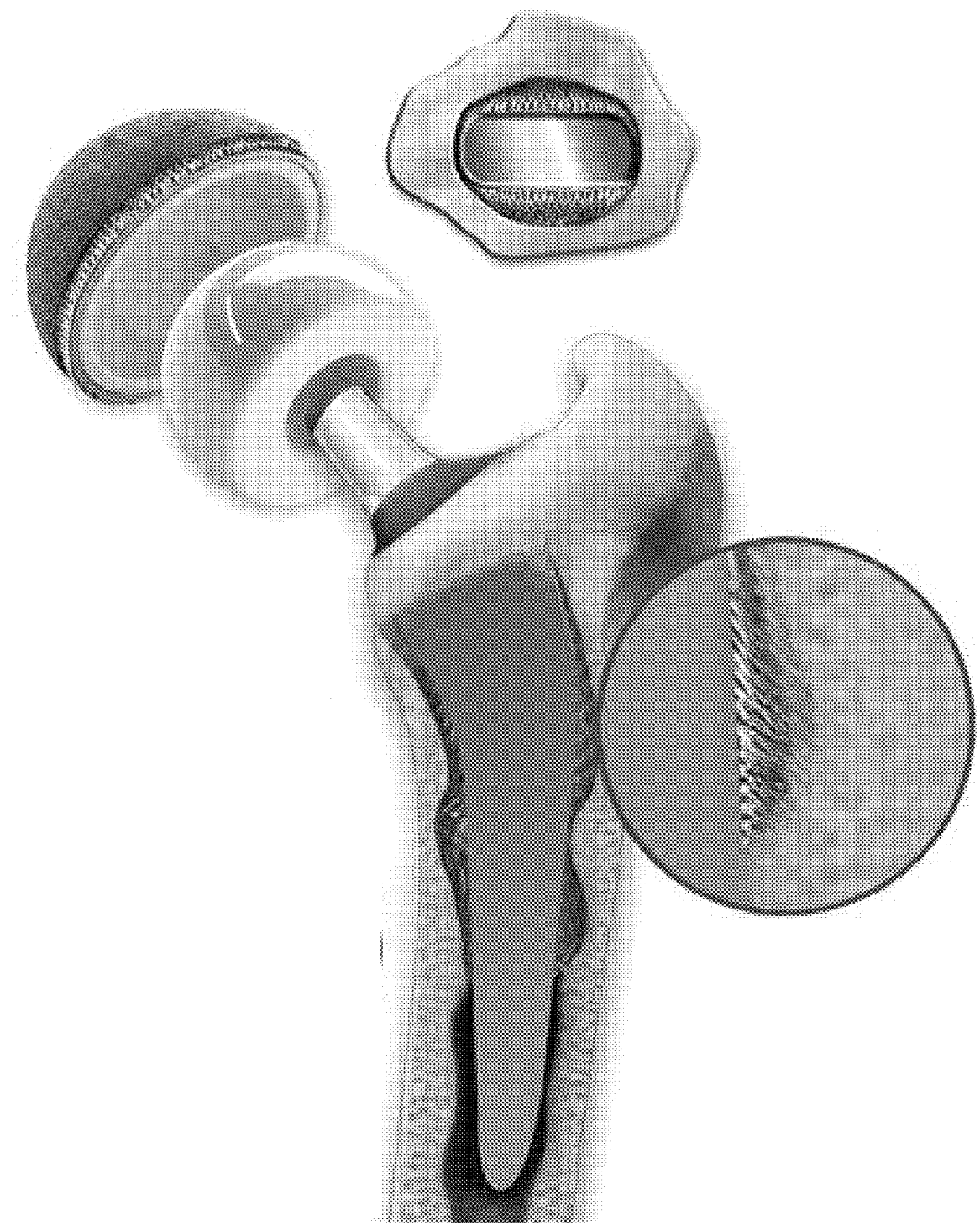

FIG. 20F shows the dynamic porous coating filling the gap between the stem of a femoral hip implant and the surrounding bone.

Figure 20G:
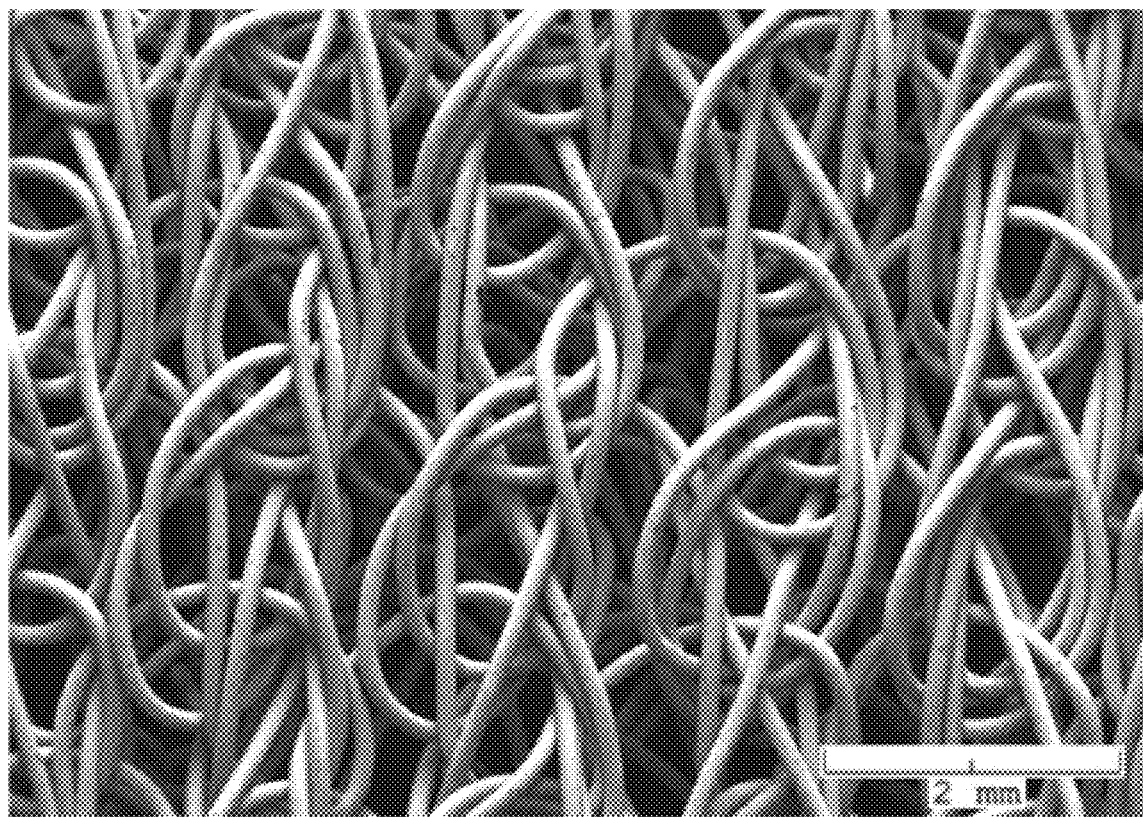

FIG. 20G shows a dynamic porous coating formed out of Nitinol, superelastic wire, with the dynamic porous coating having a mean pore size of 243 µm and with the dynamic porous coating being approximately 92.5% porous.

A dynamic porous coating formed out of shape memory material spacer fabric provides a significant improvement over conventional static porous coatings. By way of example but not limitation, the following chart shows how a dynamic porous coating formed out of shape memory material spacer fabric provides superior bone ingrowth (in both depth and area percent) over conventional static porous coatings:

| 2 WEEK RABBIT STUDY DATA | | |
|---|---|---|
| | Bone Ingrowth (depth) | Bone Ingrowth (area %) |
| dynamic porous coating formed out of shape memory material spacer fabric | 1700 µm | 18 ± 6% |
| Ti Plasma Spray | 433 µm | 8 ± 6% |

Figure 21:
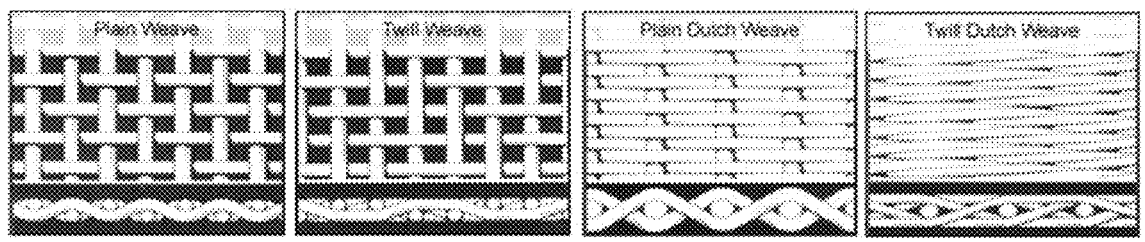
FIGS. 21-23 are schematic views showing various weaving techniques.
Figure 66:
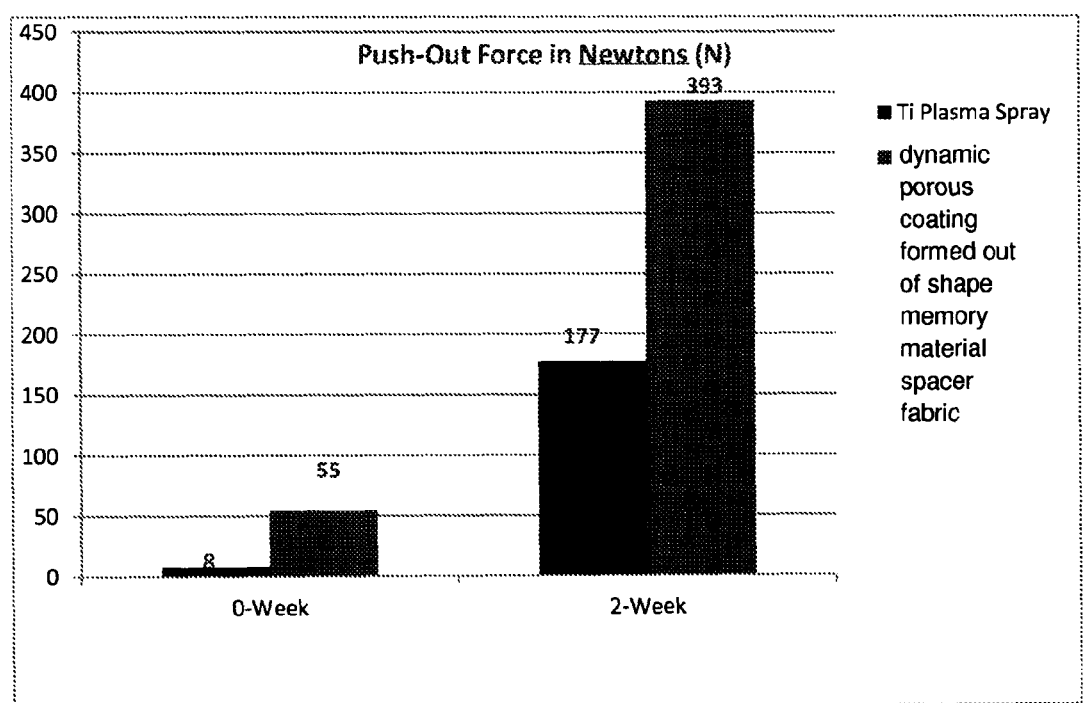
FIG. 66 is a chart showing how a dynamic porous coating formed out of shape memory material spacer fabric provides superior holding strength over conventional static porous coatings.

By way of further example but not limitation, the chart shown in FIG. 66 shows how a dynamic porous coating formed out of shape memory material spacer fabric provides superior holding strength over conventional static porous coatings:

It is also possible to create porous coatings out of shape memory materials (SMM) using weaving techniques. There are several different types of weaving techniques. They include: plain weave, twill weave, plain dutch weave, and twill dutch weave. See FIG. 21.

Figure 22:
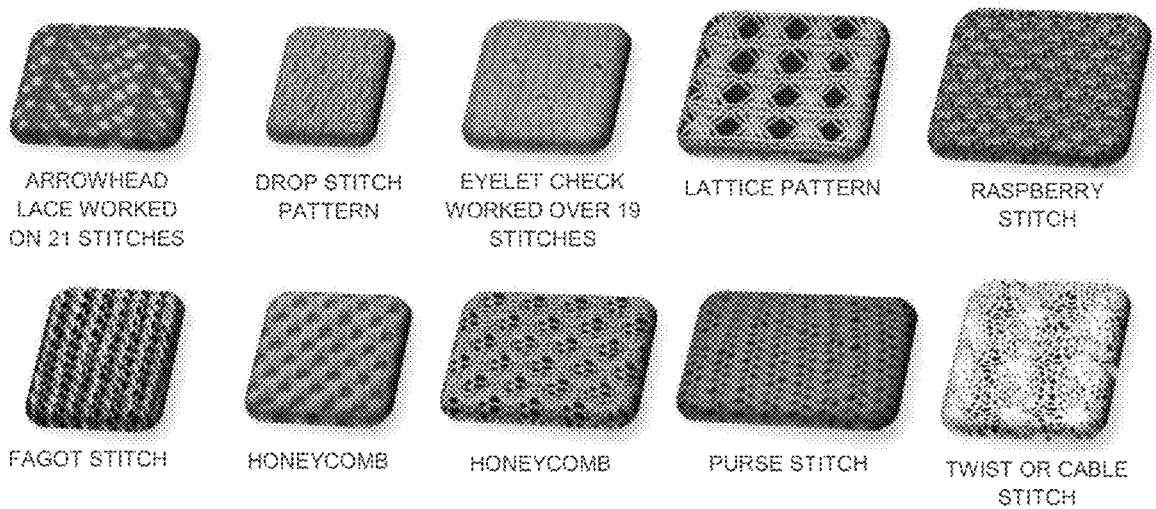

Weaving shape memory materials enables the creation of dynamic porous coatings having a wide variety of different geometries and structures. See FIG. 22. It is possible to weave mono- and multi-layer dynamic porous coatings out of shape memory materials, as well as tubular structures. It is possible to weave structures with varying widths and thicknesses within the same structure. Multiple layers of woven structures can be laminated one on top of another so as to create a more three-dimensional structure. By layering multiple sheets of materials with different pore sizes and geometries, one on top of another, a dynamic three-dimensional fabric structure can be created which has a complex interconnected network of pores. The dynamic porous coating can be constructed as a single, or multilayered, sheet that can be wrapped around the implant stem, or as a single or multilayered concentric tube that can be slid over the implant stem. The shape memory material porous coating can then be sintered to the implant prior to shape-setting.

Figure 23:
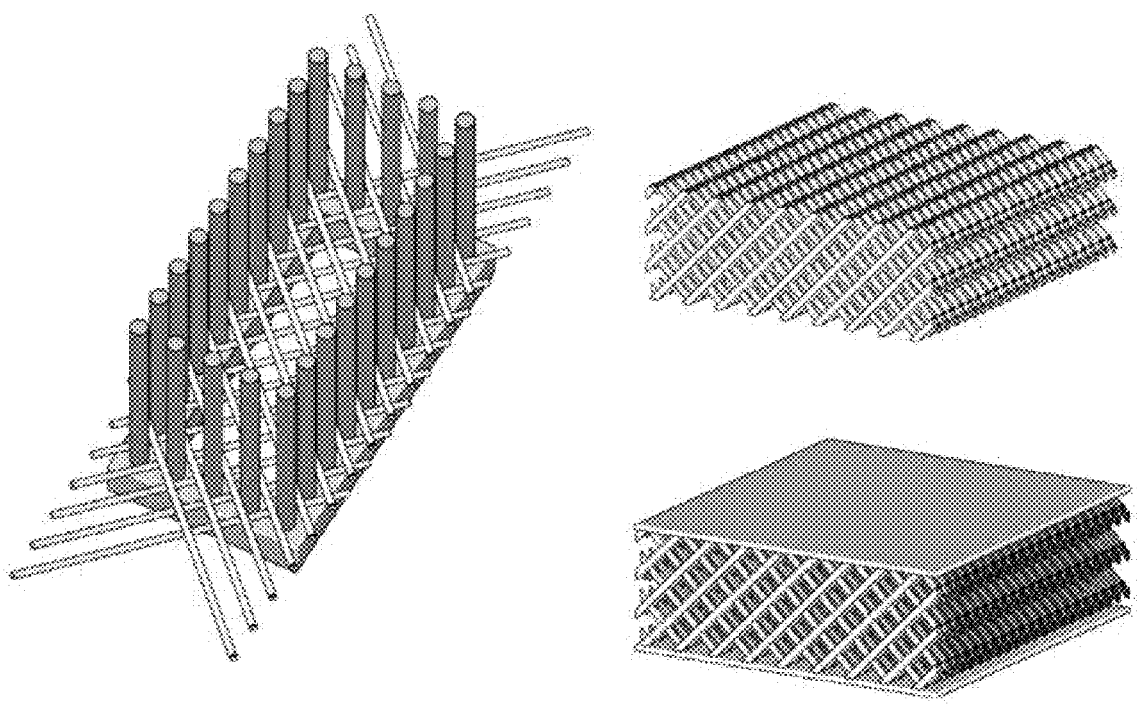

It is also possible to weave a dynamic three dimensional SMM porous structure directly. More particularly, using a jig, it is possible to weave wires and/or tubes in various patterns, building layers one on top of another, whereby to create an overall three dimensional porous structure which can then be used as a dynamic porous coating for an implant. See FIG. 23. The overall three dimensional porous structure can then be sintered to fuse the woven wires together if desired. Furthermore, if desired, a less porous, or non-porous, sheet can be attached to one or both of the faces of the woven three dimensional structure. This may be beneficial for the face that is to be sintered to the implant stem, as it will have more surface area in contact with the implant stem, and hence provide increased bonding of the dynamic porous coating to the implant.

Figure 24:
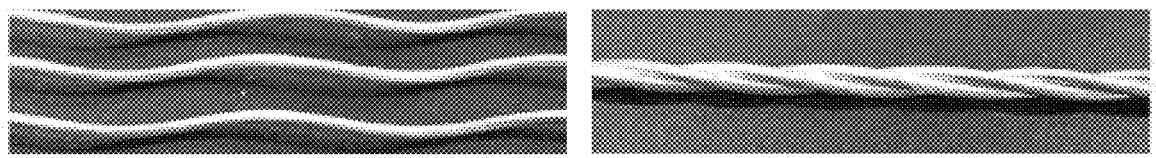
FIG. 24 is a schematic view showing how several wires may be twisted into a single helical wire.

Another method for weaving a three dimensional shape memory material (SMM) porous structure is to use a modified Kagome weave. In this approach, the Wire Woven Bulk Kagome (WBK) is assembled from continuous SMM helical wires which are systematically arranged in six directions. The SMM helical wires may themselves be created from twisted SMM wire. See FIG. 24.

Figure 25:
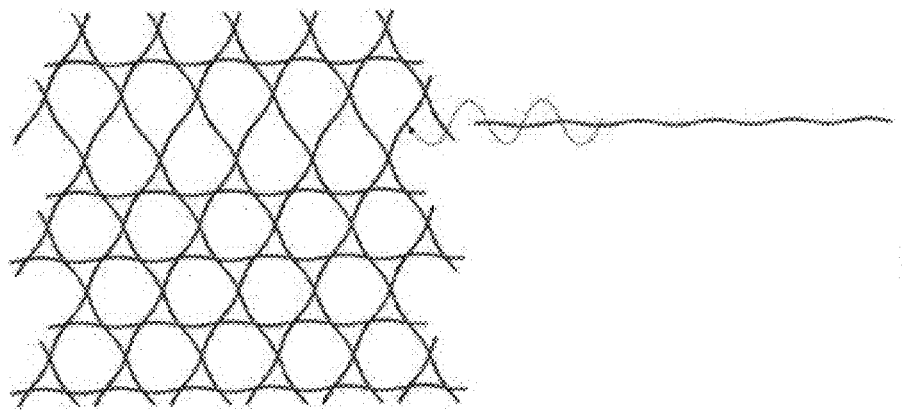
FIGS. 25-29 are schematic views showing fabrication of a Woven Bulk Kagome (WBK) weave.
Figure 26:
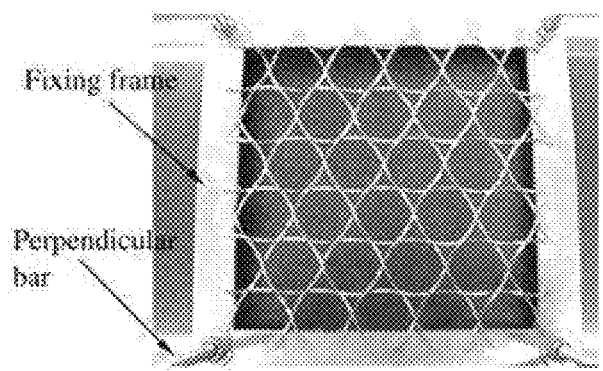

With WBK, the three dimensional structure is created in layers. According to the number of layers to be utilized, each Kagome plane is individually assembled (see FIG. 25) and placed one on top of another in a fixing frame (see FIG. 26), with an appropriate space between each layer. The space provided between each layer helps determine the overall height of the three dimensional structure.

Figure 27:
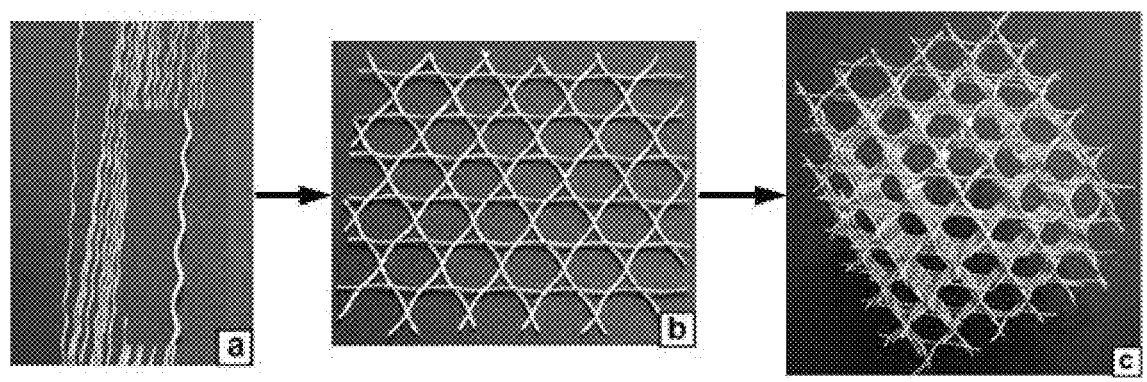

With the Kagome weave, with the layers aligned on top of one another, three additional SMM helical wires are woven through the gaps of the three different out-of-plane directions, creating the overall three dimensional wire-bulk Kagome. See FIG. 27.

Figure 28:
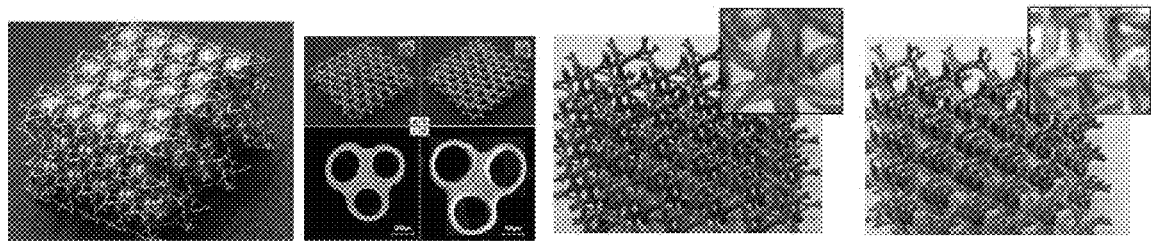

The hexagonal openings in each layer of the WBK create a near-spherical pore structure in the three dimensional weave. By changing the diameter of the starting wire and the pitch of the woven members, the pore size of the weave can be changed. Additionally, it is possible to create this weave using tubes instead of wires, and the nodes of the weave can be brazed with differing amounts of filler so as to alter the rigidity of the overall WBK structure. See FIG. 28.

Figure 29:
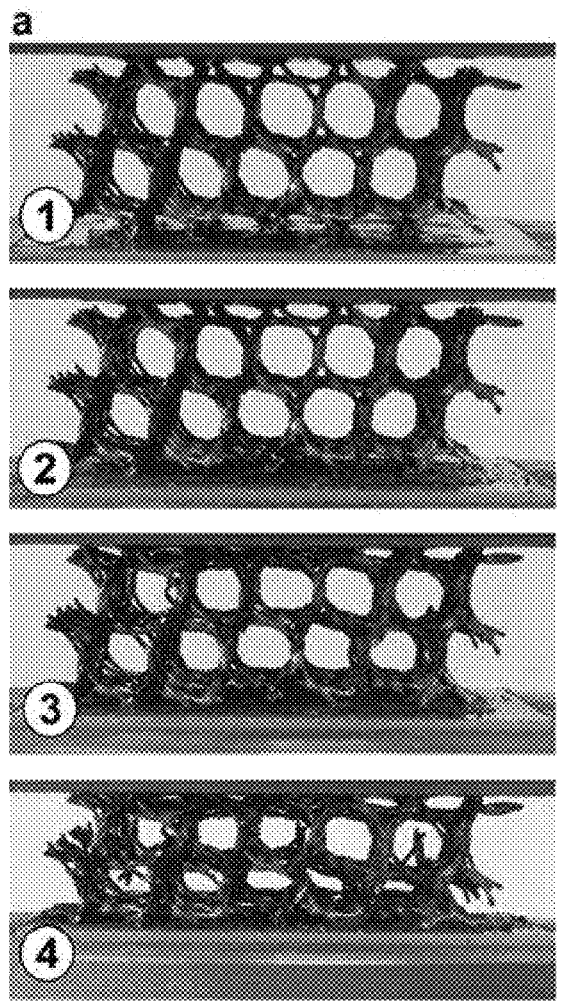
Figure 29:
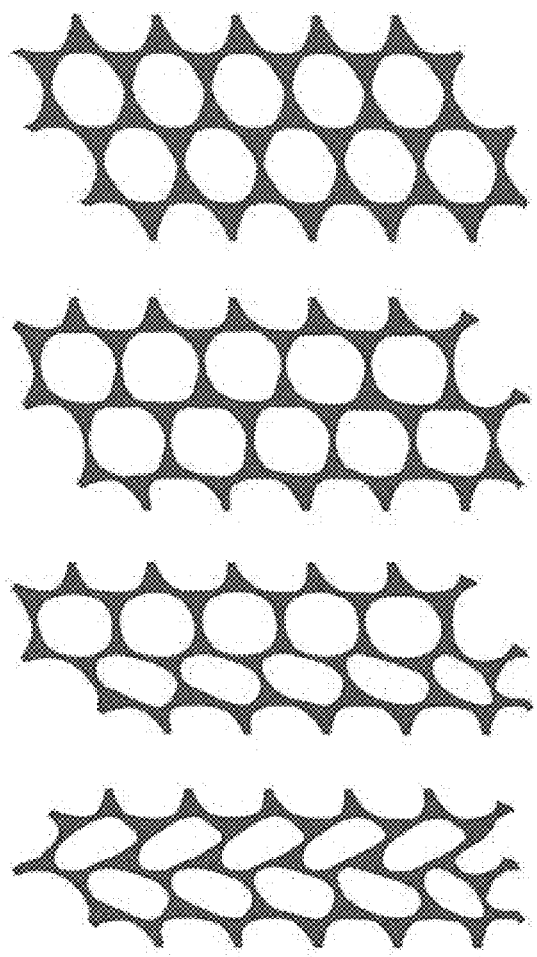

When a compressive force is applied to the WBK structure, it readily collapses, with the pores nesting as it collapses: one layer of pores collapses toward the right, and the adjacent layer collapses towards the left. This allows for large amounts of deformation. See FIG. 29.

For the application of a dynamic porous coating for an implant, it is possible to create the WBK structure using shape memory material wires or tubes. This provides a WBK structure having superelastic properties, which is ideal for application as a dynamic porous coating for an implant. The SMM WBK can be created as a multilayered sheet and either wrapped around the implant, or cored so as to create a sleeve that can be slid over the implant. The SMM WBK is then sintered onto the implant prior to shape-setting, whereby to provide a dynamic porous coating for the implant.

Figure 30:
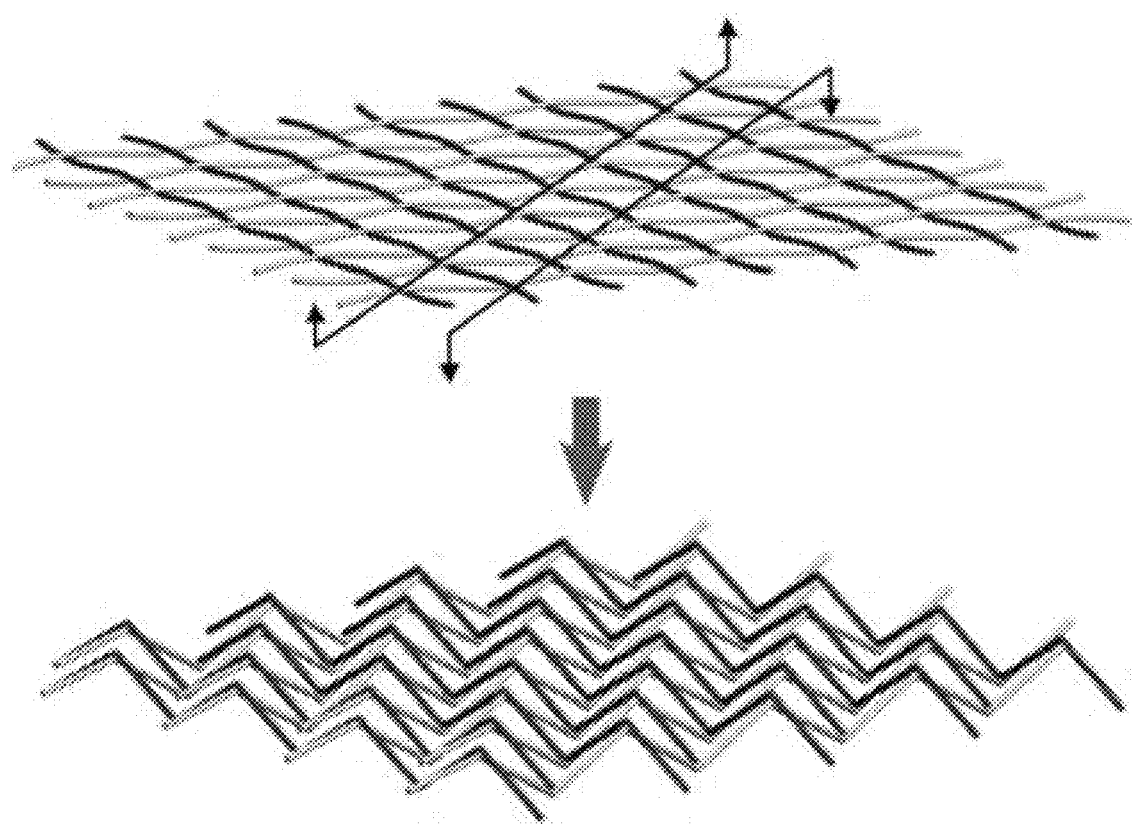
FIGS. 30-33 are schematic views showing how corrugation can be used to form a dynamic porous coating.
Figure 31:
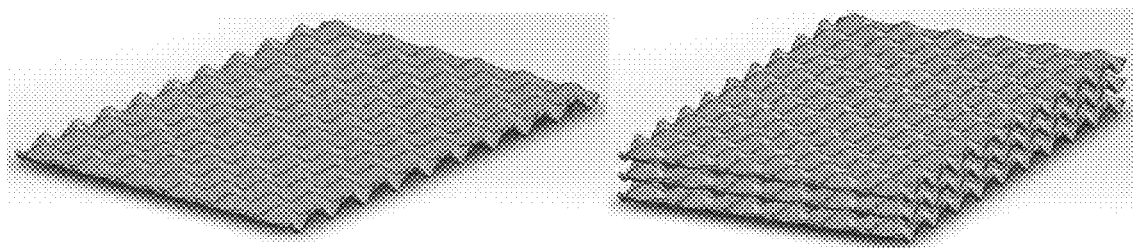
Figure 32:
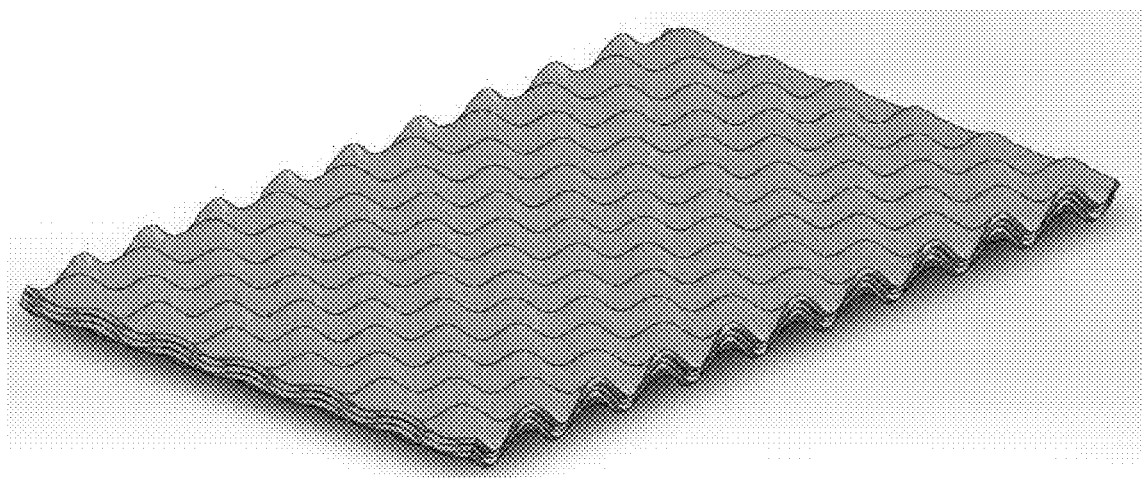

Additionally, it is possible to corrugate any of the foregoing structures to increase their porosity and spring factor. Corrugation can be performed in one or two directions. The corrugation can be accomplished by bending the layers at defined regions, or pressing the layers between two dies. Additionally, the corrugation can be linear, resulting in pyramid-shaped structures, or wavier structures, resulting in an egg-crate structure. See FIG. 30. Individual layers may be corrugated prior to layering them one on top of another (see FIG. 31), or the overall structure itself can be corrugated (see FIG. 32) after having already been formed by layering individual layers.

Figure 33:
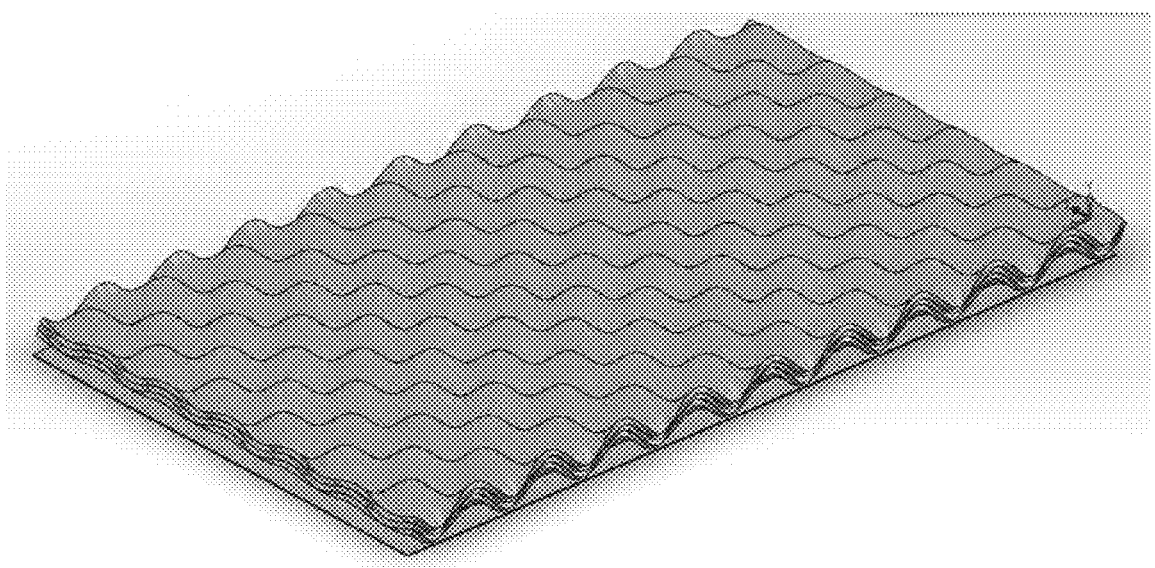

It also may be beneficial to secure the corrugated structure to a less-porous sheet in order to aid in sintering the dynamic porous coating to the implant stem. See FIG. 33.

Honeycomb- and Truss-Based Structures

Figure 34:
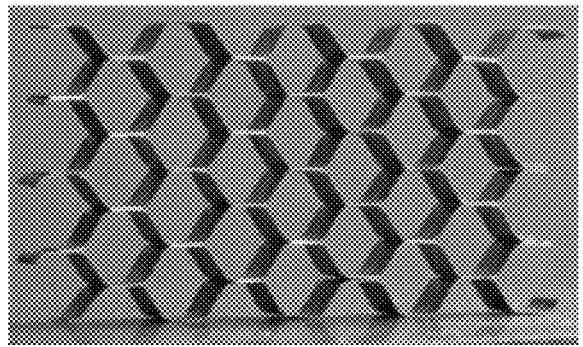
FIGS. 34-43 are schematic views showing how honeycomb- and truss-based structures can be used to form a dynamic porous coating.
Figure 35:
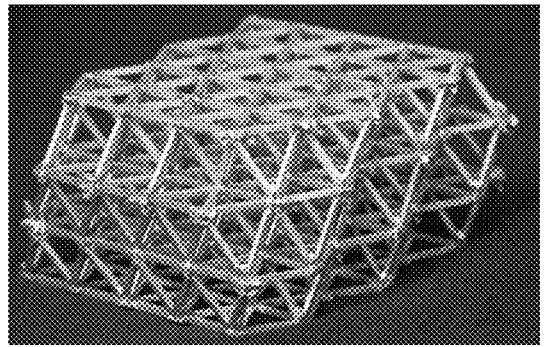
Figure 36:
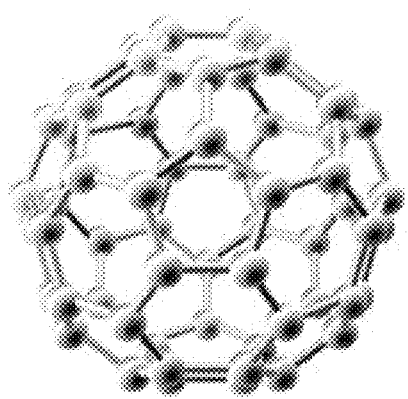
Figure 37:
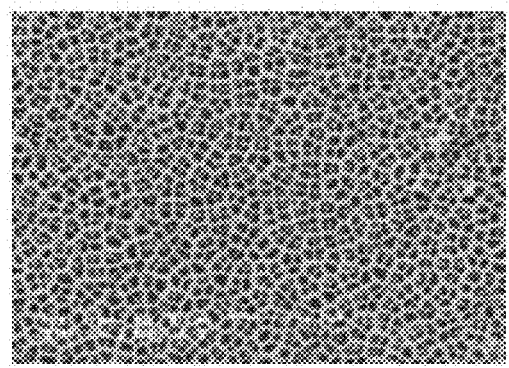

Another method for creating an open pore trabecular structure out of a shape memory material (whereby to form a dynamic porous coating) is to create honeycomb- or truss-based structures. See FIGS. 34 and 35. In one form of the present invention, the honeycomb structure can be 3D, such as a dodecahedron structure, similar to a "nano buckyballs" geometry, and is superelastic and/or has SME (shape memory effect via temperature change). See FIGS. 36 and 37. It may also be made up of a repeating pattern of diamonds, hexagons, or other shapes.

Figure 38:
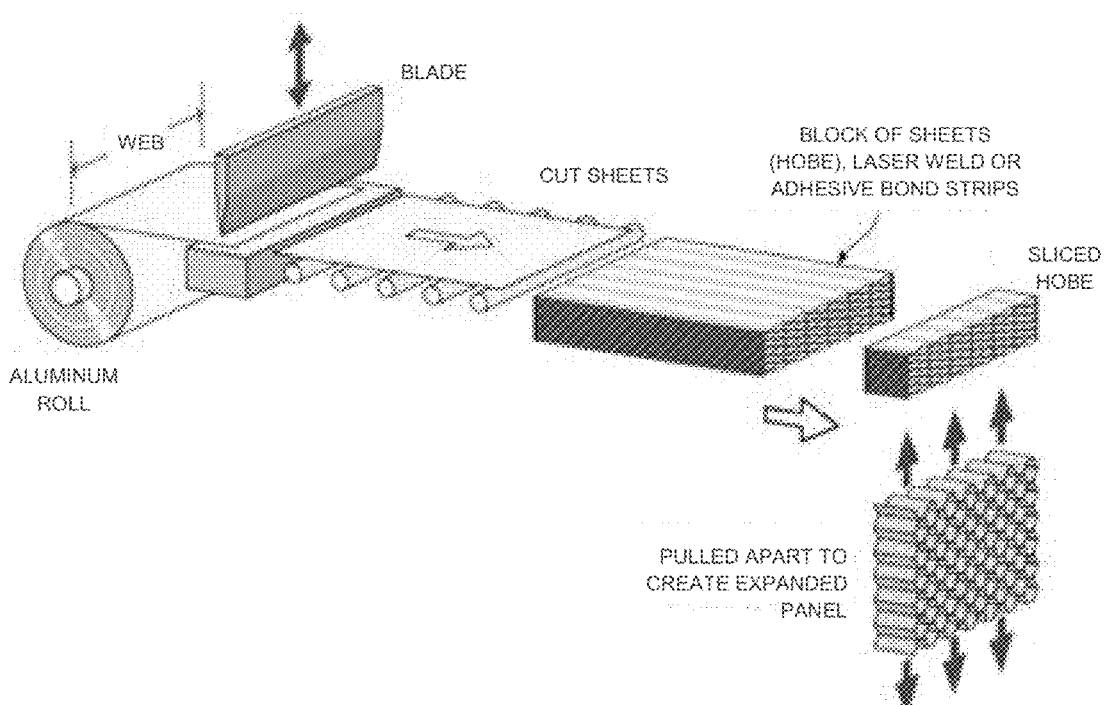
Figure 39:
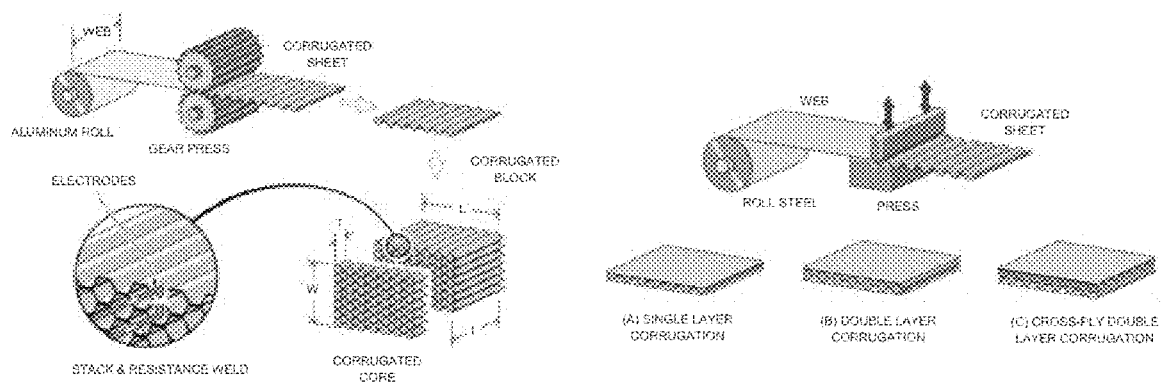
Figure 40:
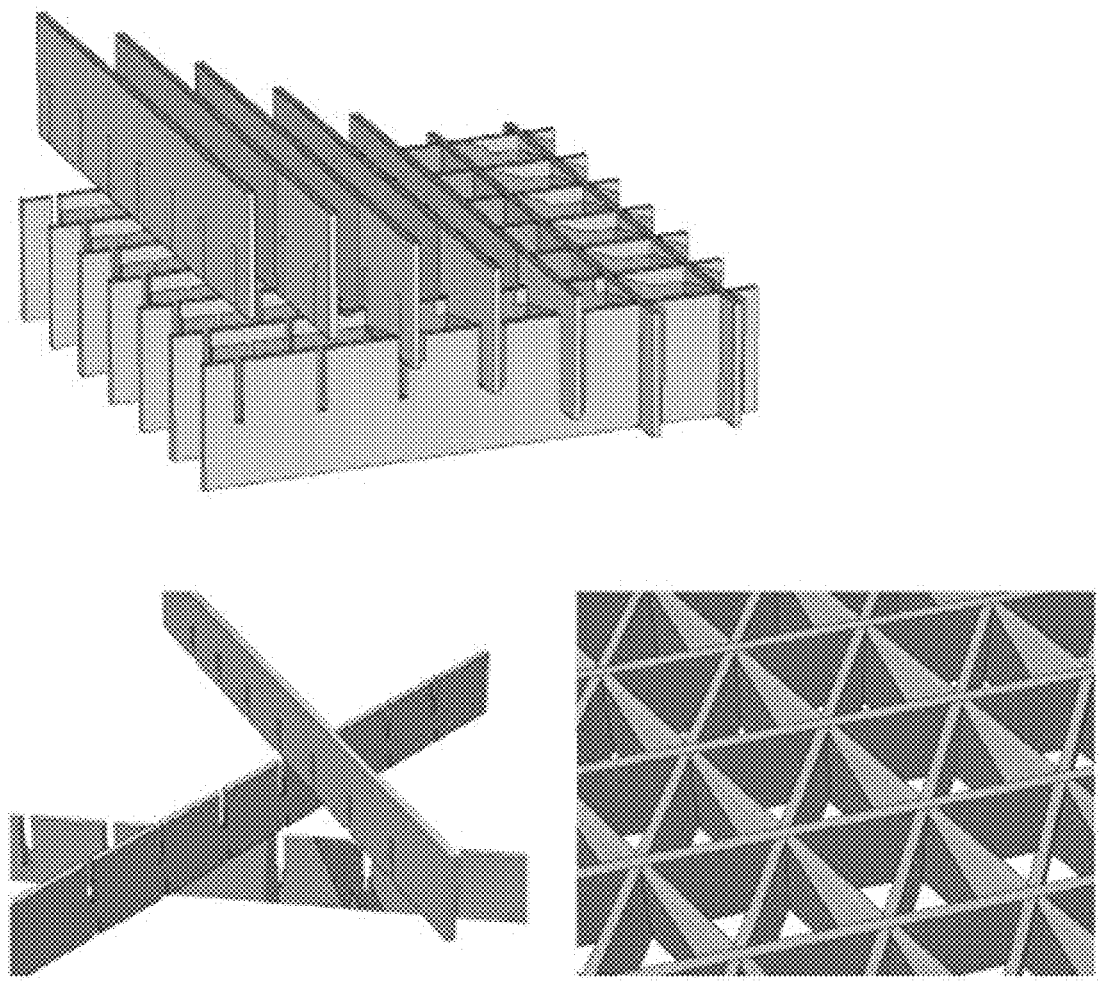

There are many methods known in the art for creating honeycomb- and truss-based structures. By way of example but not limitation, honeycomb structures can be created using a HOBE method (Honeycomb Before Expansion), a corrugation process, or a strip-slotting method. In the HOBE manufacturing process, multiple layers of material can be stacked on top of each other, welded along defined regions, sliced, and pulled apart so as to create the expanded honeycomb. See FIG. 38. In the corrugation manufacturing process, a press can be used to corrugate a sheet of material. Multiple sheets of material can then be stacked on top of each other so as to create a honeycomb structure. Alternatively, the corrugated sheets can be layered perpendicular to one another, creating a cross-ply structure. See FIG. 39. In the strip-slotting method, strips of material are notched so that they can be interlocked so as to form the desired honeycomb structure. The interlocked strips can then be welded or braised together for additional support. See FIG. 40.

Figure 41:
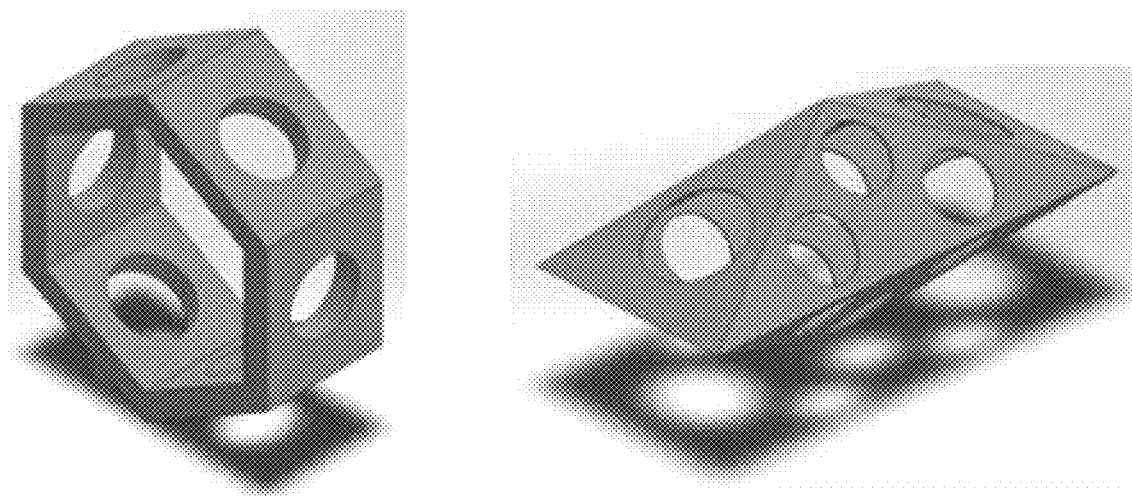

To increase the overall porosity of the honeycomb structure, which can be desirable for its use as a dynamic porous coating, holes can be formed in the faces of the sheets, either prior to, or following, the creation of the three-dimensional honeycomb structure. See FIG. 41.

Figure 42:
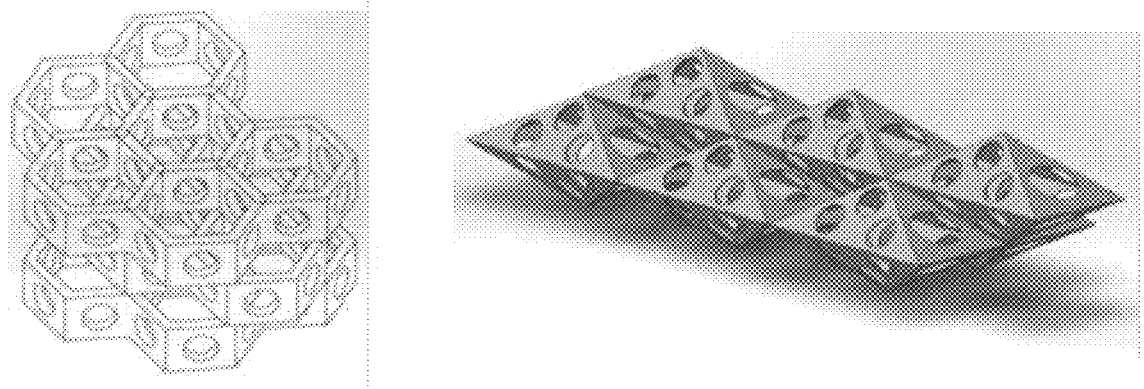

Furthermore, by staggering the orientation of the hexagonal elements (instead of aligning them one on top of another), a more complex pore structure can be created for the dynamic porous coating. See FIG. 42.

Figure 43:
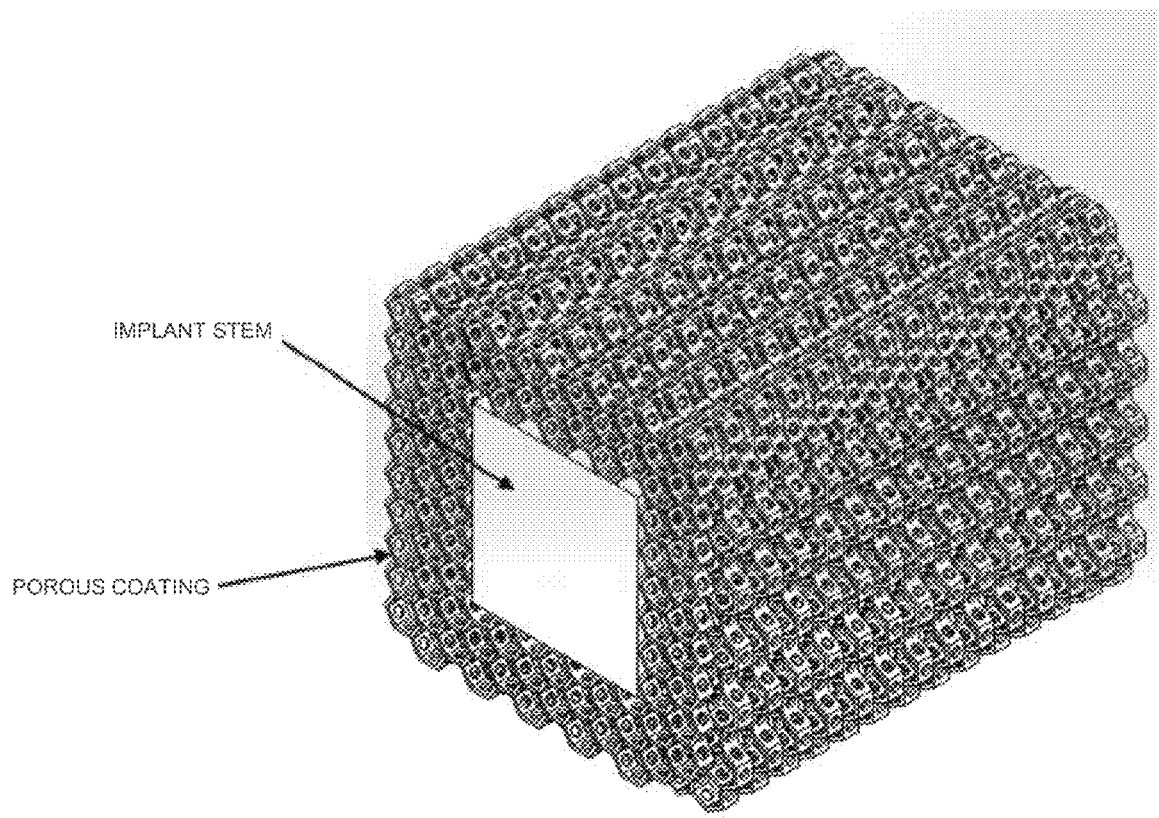

Sheets of honeycomb can be layered one on top of another, and attached to the outside surface of the implant stem by braising, sintering, or laser welding, whereby to form a dynamic porous coating for the implant. See FIG. 43.

Sintered Beads

Figure 44:
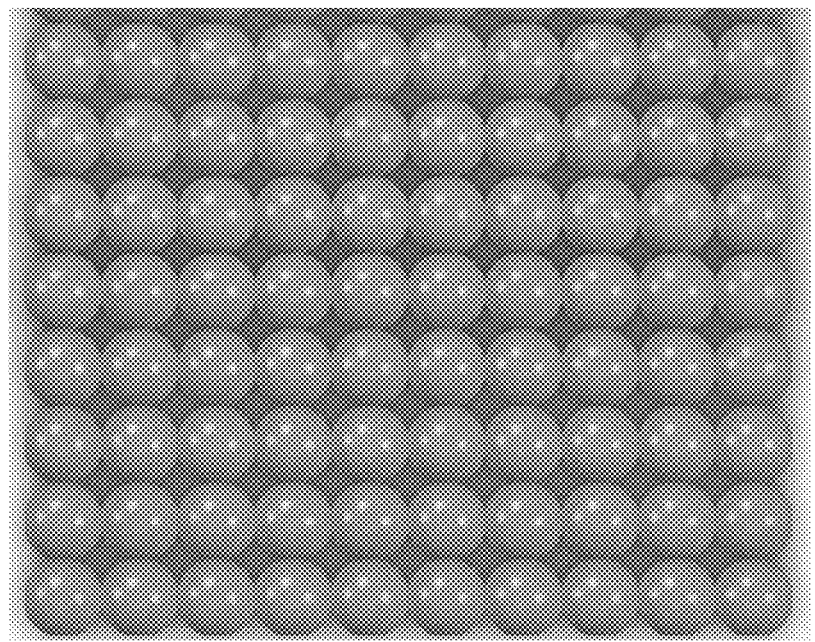
FIGS. 44-46 are schematic views showing how sintered beads can be used to form a dynamic porous coating.
Figure 45:
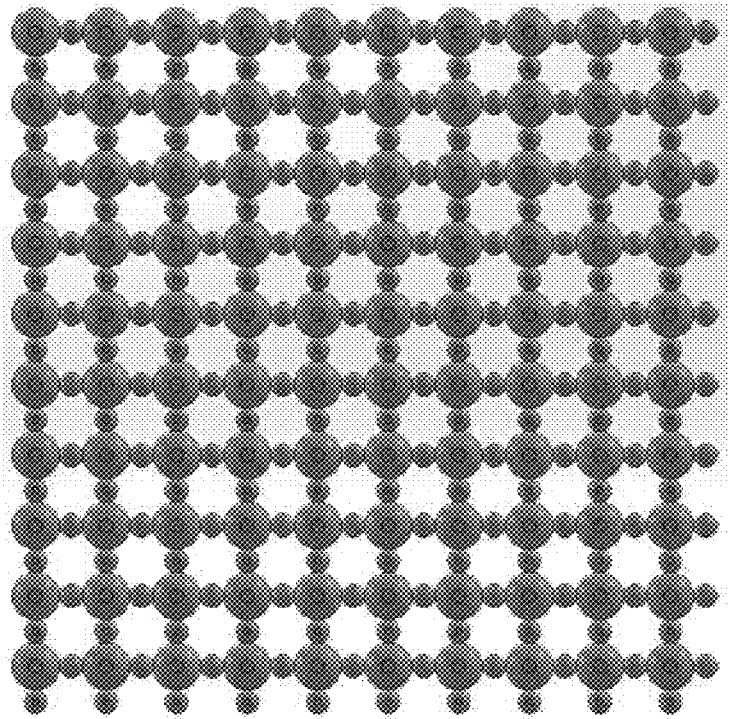

Dynamic porous coatings can also be fabricated by sintering together beads. The beads can be spheres, or other shapes, so as to increase the overall porosity of the dynamic porous coating. The beads can be laid out in individual layers, and then sintered together so as to fuse them into sheets. The sheets can then be stacked one on top of another so as to build a multi-layered three-dimensional dynamic porous coating. Different porosities can be achieved by using beads of different shapes. As an example, using spherical beads of the same diameter results in a fairly dense structure (see FIG. 44); however, using spherical beads of two different diameters generates a much more porous structure (see FIG. 45).

Figure 46:
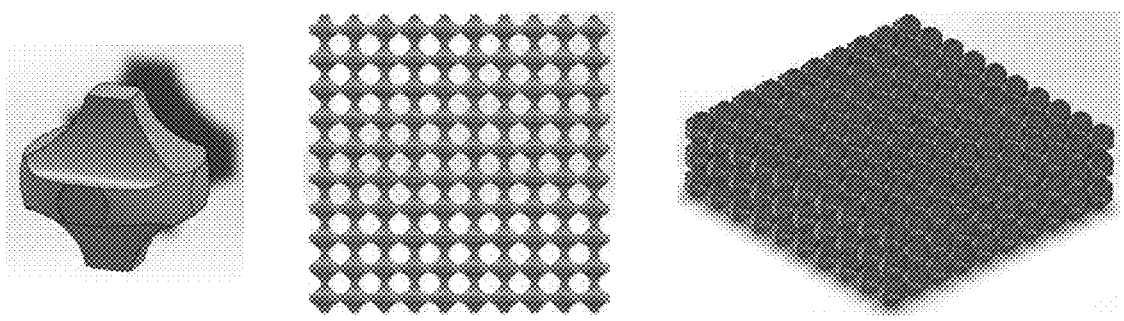

Additionally, the beads need not be spherical. By way of example but not limitation, the beads can be made in the shape of "jacks" (see FIG. 46) or another three-dimensional shape. By assembling the beads in the manner discussed above, it is possible to create even more porous structures with increased interconnectivity between the pores, whereby to facilitate their use as a dynamic porous coating for an implant.

Lamination of Multiple Layers

Figure 47:
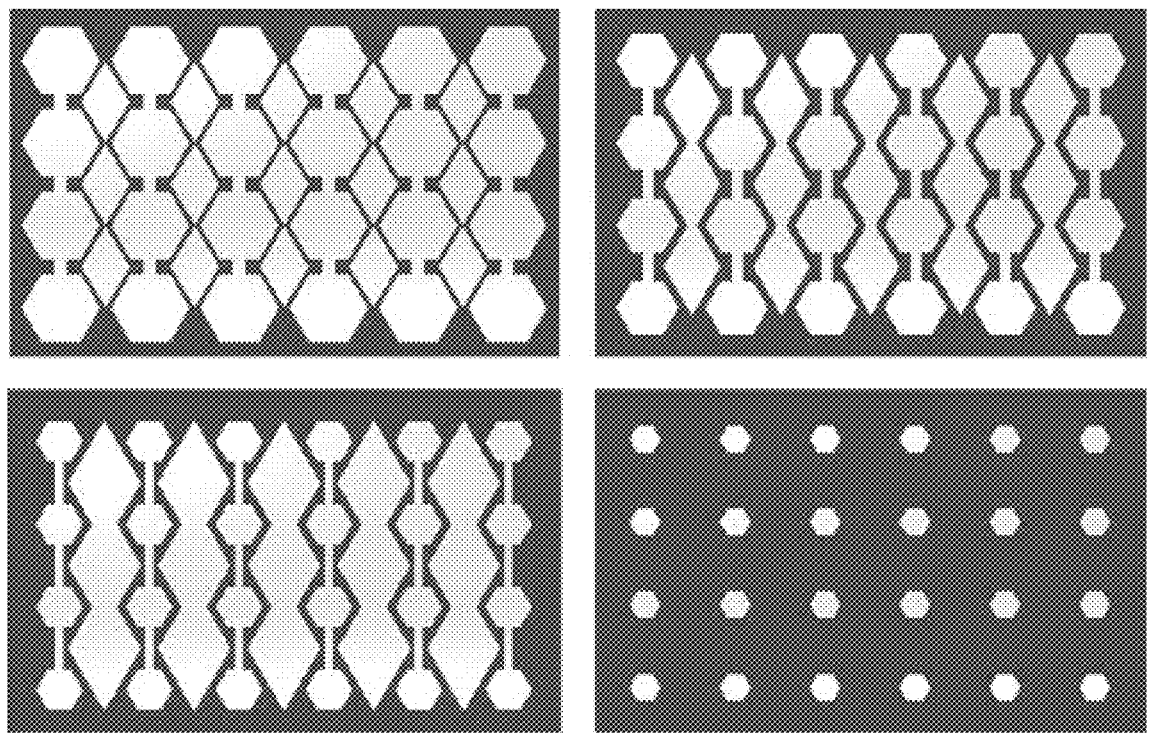
FIGS. 47-49 are schematic views showing how lamination of multiple layers can be used to form a dynamic porous coating.
Figure 48:
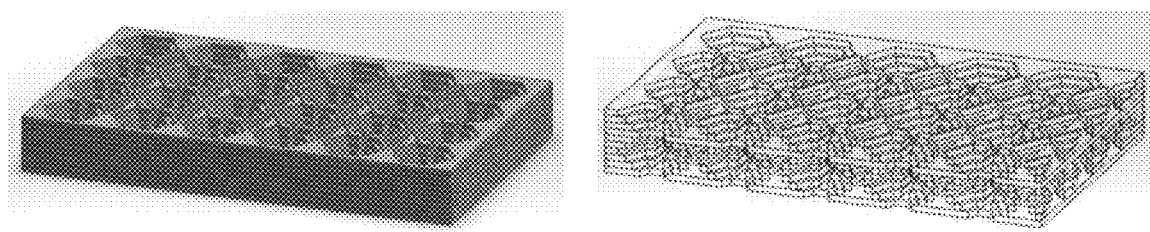

Another method for producing a dynamic porous coating is to laminate multiple thin sheets of shape memory material one on top of another. A pattern can be chemically etched, punched, or cut out of each of the sheets and, by altering the geometry of the pattern on each sheet, it is possible to create a porous dodecahedron or other multi-facet structure which can function as a dynamic porous coating for an implant. More particularly, each sheet can be layered one on top of another and sintered together so as to create a dynamic porous structure. By changing the geometry of the cut-out on each layer, it is possible to create many different dynamic porous structures. The dynamic porous structure can be made in a sheet and wrapped around the implant, or a sleeve can be cut out of the material and the implant stem placed within the sleeve, whereby to form a dynamic porous coating for the implant. By way of example but not limitation, four sheets of Nitinol (see FIG. 47), each with different geometries, can be stacked one on top of another (see FIG. 48) so as to create a dynamic porous coating having a three-dimensional structure.

Figure 49:
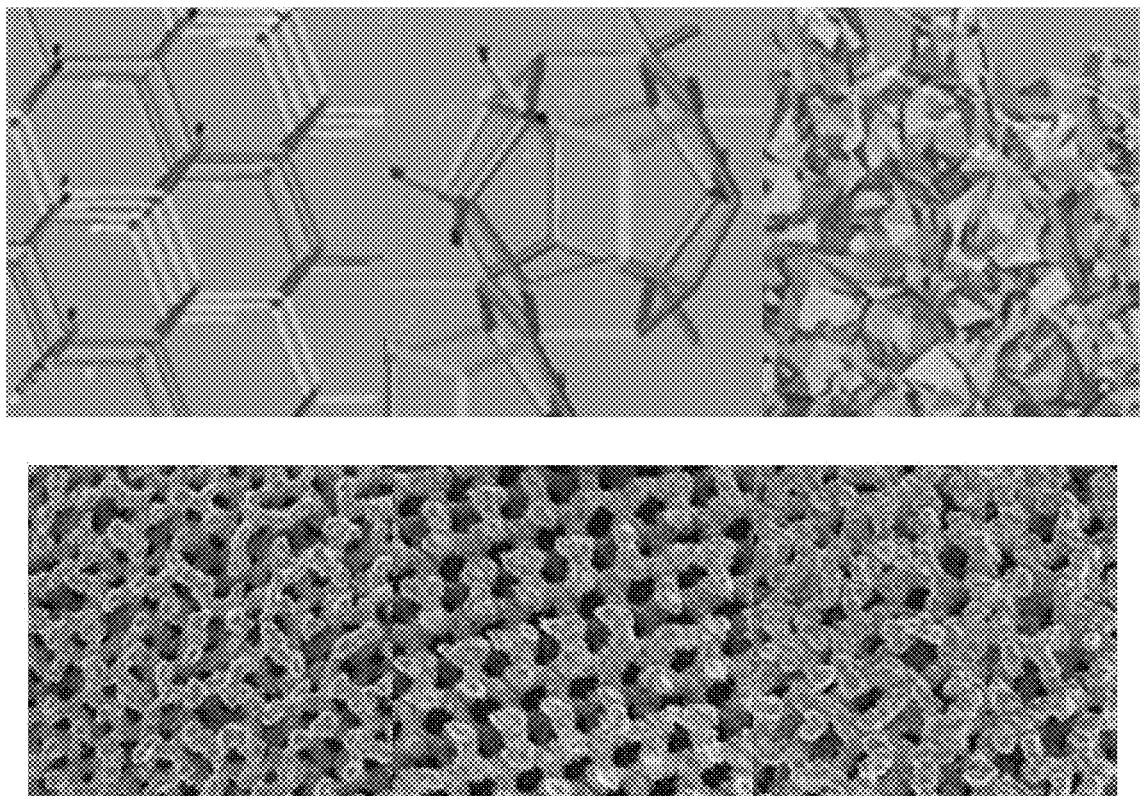

Another method for manufacturing a dynamic porous coating is to use an additive manufacturing technique. One such technique uses metal powder, with a particle size of from about 10 µm to about 200 µm (i.e., Nitinol powder), and an energy source (e.g., a laser or electron beam) to build structures layer by layer, selectively sintering powder together so as to build a three dimensional shape. More particularly, a thin layer of the powder is spread out as a uniform layer, and then an energy source selectively melts regions of the powder, fusing the particles together. Another layer of powder is then spread on top of the first layer, and the energy source again melts regions of the powder. This process continues until the complete three-dimensional dynamic porous coating is built. See FIG. 49. Using this manufacturing technique, it is possible to construct both solid and porous structures, or combinations of the two (e.g., a solid section for attachment to the substrate of an implant and a porous section for engagement with bone). It is possible to manufacture sheets of the dynamic porous coating that can then be wrapped around the implant stem, sleeves of the dynamic porous coating that can be slid over the stem, whereby to create implants with dynamic porous coatings mounted to the stem.

Coatings

Regardless of the manufacturing process used to create the dynamic porous coating, it may be desirable to apply a coating of another material on top of the dynamic porous coating. By way of example but not limitation, a Nitinol porous coating may be covered with a thin coat of titanium or a bone agent such as HA (e.g., by sputtering or plasma spraying). This titanium coating would seal the Nitinol and prevent the Nitinol from being in direct communication with the body. Thus, if a concern exists regarding nickel leaching out of the Nitinol and into the body, this titanium coating would be one approach for protecting against this. The coating can be applied in a number of ways, such as, but not limited to, physical vapor deposition, chemical vapor deposition, powder metallurgy, and electroplating. Additionally, the plating process may be performed so as to increase the opacity of the dynamic porous coating on X-ray or MRI. If desired, a titanium oxide layer can be formed on the NiTi so as to enhance biocompatibility.

Surface Texturing

Figure 50:
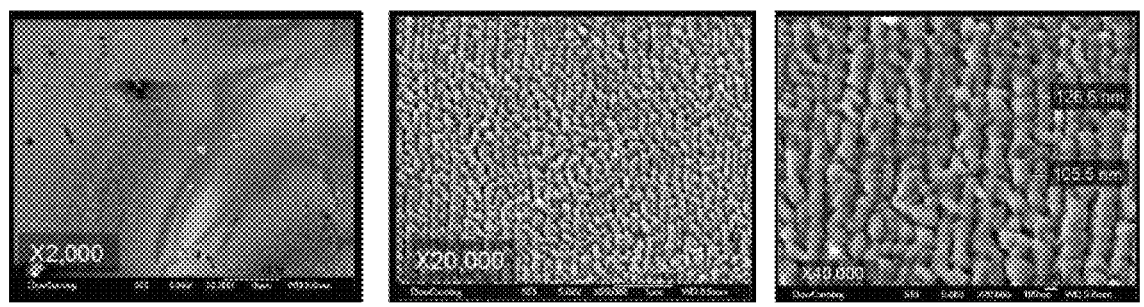
FIG. 50 is a schematic view showing how surface texturing may be applied to the dynamic porous coating.

Additionally, in order to aid in osseointegration, it may be beneficial to modify the surface of the dynamic porous coating so as to provide it with additional nano-texturing. This may be accomplished by sintering non-uniform, non-spherical powder to the surface of the dynamic porous coating. This powder may or may not be a shape memory material. Surface texturing may also be accomplished by using starting materials that have a rough finish. As an example, a knit dynamic porous coating may be made from wire that has been pickled or etched prior to knitting so as to increase its surface roughness. Alternatively, etching or pickling may be performed on the final dynamic porous coating prior to sintering to the implant stem. See FIG. 50.

Implantation

While it is possible to insert an implant with a dynamic porous coating into the medullary canal of a bone by driving it in and forcing the dynamic porous coating to comply with the internal geometry of the medullary canal, it may also be beneficial to use a rapidly dissolving paste to keep the dynamic porous coating in the compressed state during insertion. As an example, calcium hydroxylapatite (HA) [$Ca_{10}(OH)_2(PO_4)_6$], β tricalcium phosphate (TCP) [$Ca_3(PO_4)_6$], fluorapatite, and biphasic calcium phosphate, a HA/β TCP combination, can be made into pastes, slurries, or cements that dissolve over controlled amounts of time.

An additional benefit to using one of these materials is that they are proven bone growth agents. HA is often plasma-sprayed onto a hip stem to increase the rate of osseointegration. By using a rapidly dissolving HA paste to temporarily compress the dynamic porous coating, the implant is delivering localized bone growth agents directly to the site where they are needed.

As an example, a TCP paste can be applied to the dynamic porous coating. The dynamic porous coating can then be compressed and the TCP allowed to dry. Once the TCP is dried, the compressive force can be removed, and the TCP will hold the dynamic porous coating in the compressed state. The implant can then be inserted into the medullary canal. The native physiological solution at the site of implantation will dissolve the TCP coating, and the dynamic porous coating will be allowed to expand, filling any gaps between the implant and bone, and where constrained, apply chronic bone-building strain to the bone.

Alternatively, sterile saline or another biocompatible solution can be irrigated to the site of the implant to aid in dissolving the TCP coating.

Attachment of Dynamic Porous Coating to the Implant

Traditionally, porous coatings have been attached to the implant substrate by using a solid state diffusion or sintering process that approaches the melting temperature of the materials being joined. However, the elevated temperatures required for sintering have deleterious effects on the underlying substrate and include reduced notch toughness and reduced fatigue properties. The elevated pressures recommended for sintering may also cause a decrease in overall porosity as the porous coating may partially collapse under the pressure and elevated temperature. Additionally, sintering will occur wherever two materials are in contact, thus unintentionally increasing the stiffness of the post-sintered material and compromising fatigue strength at the sintered sites.

By way of example but not limitation, if a metal spacer fabric were to be sintered onto a titanium stem substrate, not only would the bottom layer of the metal spacer fabric sinter to the stem of the implant, but also any place a fiber touched another fiber would be sintered together. This would greatly increase the stiffness of the spacer fabric, potentially rendering it non-elastic, i.e., static. For this reason, where the present invention comprises metal spacer fabrics, and/or where the components of the dynamic porous coating will be negatively influenced by sintering, it may be preferred that the dynamic porous coating be secured to the implant using a non-sintering technique.

To this end, instead of sintering the dynamic porous coating to the substrate of the implant, the dynamic porous coating may preferably be brazed to the substrate of the implant. Brazing is a metal-joining process whereby a filler metal is heated above its melting point and distributed between two or more close-fitting parts by capillary action. The filler metal is brought to slightly above its melting (liquidus) temperature while protected by a suitable atmosphere, usually a flux, a vacuum, or an inert atmosphere. It then flows over the base metal, known as wetting, and is then cooled to join the pieces together. The dynamic porous coating which is brazed to the substrate preferably adheres to the following ASTM specifications:

| Test | Spec | Outcome |
| --- | --- | --- |
| Shear Strength | F1044 | Shear strength of the surface/substrate interface >20 MPa |
| Shear Fatigue Strength | F1160 | Shear fatigue strength of surface coating should be test to $10^7$ cycles. |
| Tensile Strength | F1147 | Tensile strength of the surface/substrate interface >22 MPa |
| Abrasion Resistance | F1978 | Average mass if liberated porous coating <65 mg/100 cycles |

For a medical application, the brazing material must be biocompatible. Silver (Ag) is one example of a biocompatible brazing agent. The brazing of Ag with Ti causes a eutectic transformation, creating TiAg (η) which facilitates the joining of Ti with the spacer fabric material without causing any deleterious intermetallic phases to form. Normally, brazing operations avoid eutectic reactions so as to not melt the surface of the material, which can create a deleterious, brittle recast layer. Brazing titanium with silver occurs at approximately 1740° F. (950° C.), a temperature low enough to not cause a deleterious effect to the implant notch strength or fatigue.

Since, during the brazing operation, the silver will wet and flow under capillary action, it is important to use a uniformly thin layer of silver. If too much silver is used, it will melt and fill the pores of the dynamic porous coating. One method for applying a uniform thin layer of silver is to electroplate the silver onto the surface of the implant stem.

Methods of electroplating Ag onto a Ti stem are known in the art, however, they require a nickel or copper strike layer to first be deposited on the implant. Ni and Cu are not biocompatible, and therefore cannot be used for the present application. For this application, where the Ag does not need to have strong adherence to the substrate, it is possible to grit blast the surface of the implant, chemically etch it, and plate a layer of silver onto the titanium stem. While the Ag will not be tightly bound to the substrate, it is bound sufficiently well to allow the dynamic porous coating to be pressed against it during brazing without the Ag flacking off. The thickness of the Ag preferably ranges from 100 nm to 5 μm. Another approach is to ion implant Ag to the titanium substrate. Yet another approach is to create the dynamic porous coating (e.g., SMM spacer fabric) with clad wire which has Ti or NiTi in its core, and Ag on its outer surface, and then braze the clad wire to the implant, without a need to pre-plate the substrate prior to brazing.

The use of a silver brazing agent provides additional significant advantages. More particularly, the rate of infection in primary total hip arthroplasty is approximately 1-3%, and the rate of infection after revision of infected hip prostheses is up to 14%. While silver serves a primary function as a brazing agent, it is also well known for its bactericidal properties and the use of silver on medical devices has previously been approved by worldwide regulatory bodies on a large number of products.

During the brazing process, the silver wets and runs over the entire surface of the dynamic porous coating. This results not only in the dynamic porous coating brazing to the stem, but also provides a thin coating of elemental silver covering the fibers of the SMM spacer fabric. Atomic silver dissolves into silver ions which, at low doses, will eliminate bacterial cells with no toxicological effect on the human patient. The surface modification technology applied during the application of the dynamic porous coating to the implant is of great benefit to effectively preventing deep-seated infection. The silver treatment enables the steady release of silver ions from the implant's surface over several months by dissolution into body fluids, eventually leaving a silver-free implant that has long-term durability and biocompatibility. As patients are at highest risk of infection during the initial healing process following surgery, the delayed release of silver ions is sufficient to provide a high level of protection.

Figure 51:
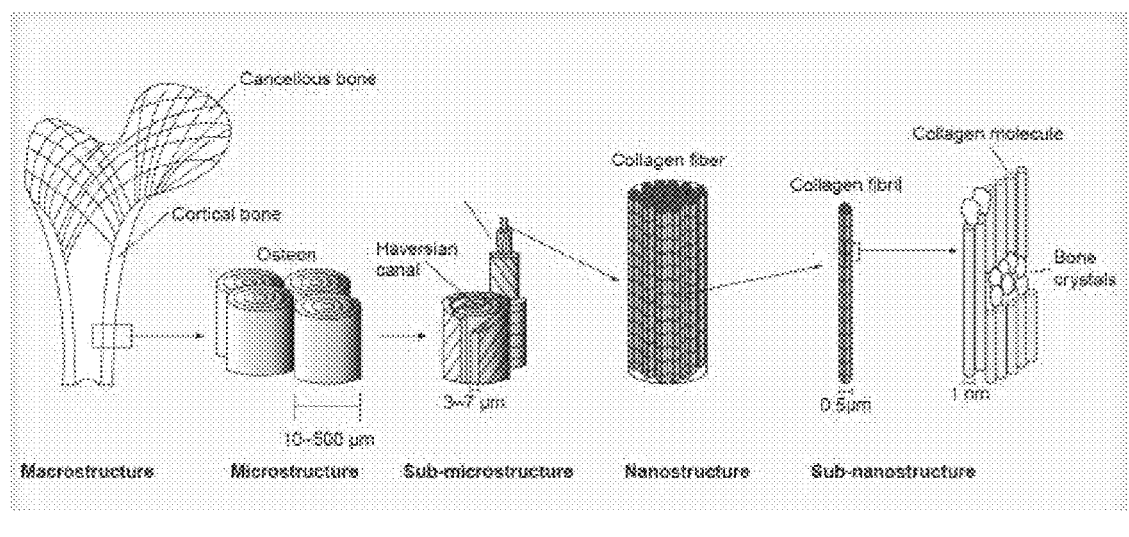
FIG. 51 is a schematic view showing the micro- and nano-structure of bone.

Coordinating the Attributes of the Dynamic Porous Coating with the Attributes of Human Bone Human bone is assembled from nano-sized organic and mineral phases into large architectures. See FIG. 51. Calcium phosphate crystallites, typically 200-800 angstroms long, 2-5 nm thick, and compositionally and structurally similar to hydroxyapatite, are typical nanomaterials for forming bone. In addition, other proteins in the extracellular matrix of bone are nanostructured similar to Type I collagen fibers. The SMM dynamic porous coatings of the present invention can have varying pore and strut sizes, ranging from micro to nano scale, so that the bone cells appropriately interact with the SMM dynamic porous coatings, e.g., for optimal osseointegration. The SMM dynamic porous coatings of the present invention can have engineered nano structures as small as 1 nm in size which can be created to more naturally adhere to the 1 nm bone crystals, and/or can be engineered so as to be larger, whereby to match the larger submicrostructure and microstructure of bone.

Figure 52:
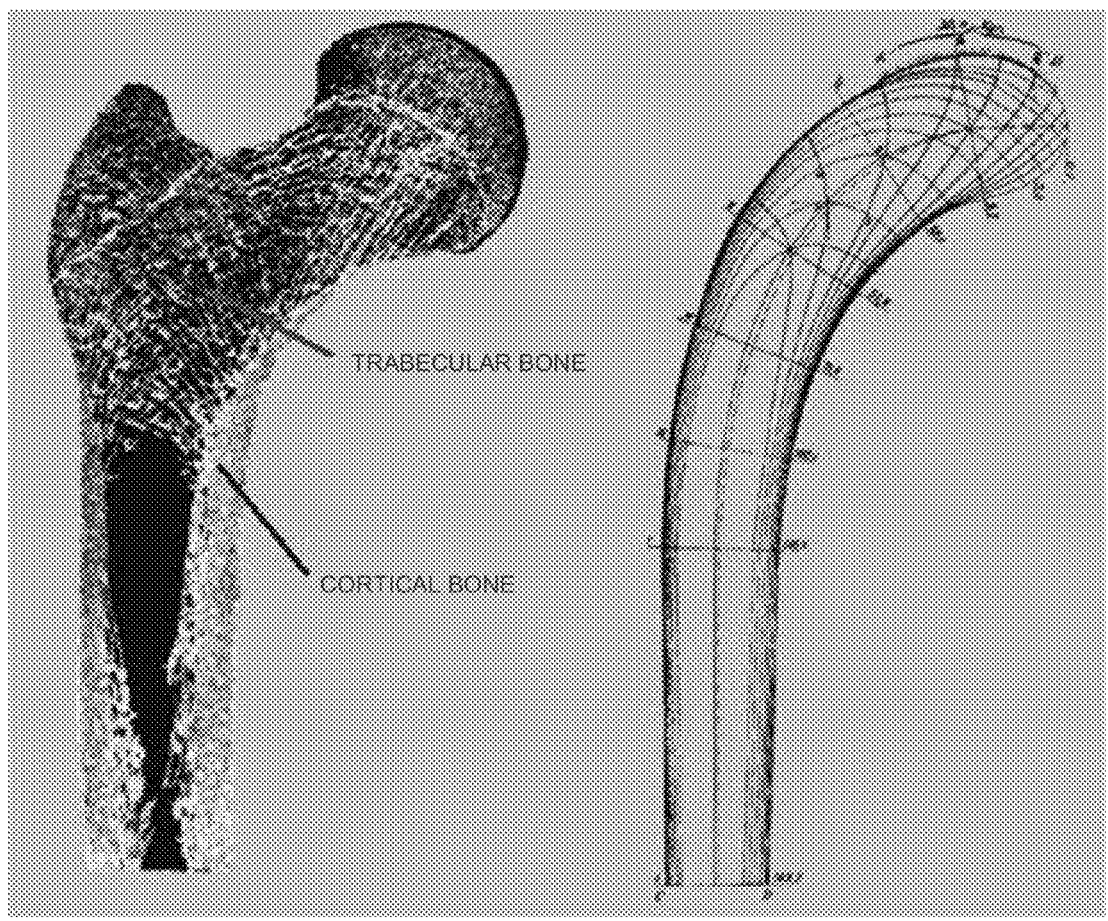
FIG. 52 is a schematic view showing the material properties of cortical and cancellous bone.

Regardless of the manufacturing processes used to create the dynamic porous coating of the present invention, and its pores and struts, their yield strength and elastic modulus are preferably engineered to desirably match the pore size and stiffness of bone by modifying one or more of (i) the pore size; (ii) strut thickness, width and length; and (iii) by modifying the amount and position of the packed "buckyball" structures in relation to one another (where a "buckyball" structure is used to form the dynamic porous coating). The SMM dynamic porous coating can have an modulus of elasticity of about 5-25 GPa so as to match the modulus of elasticity of cortical bone, or a modulus of elasticity of about 1-10 GPa so as to match the modulus of elasticity of cancellous bone. Additionally, the stiffness of the dynamic porous coating can be modulated so that the proximal region of the dynamic porous coating matches the stiffness of the cancellous/trabecular bone and the distal region of the dynamic porous coating matches the stiffness of the cortical bone. See FIG. 52.

Nitinol

Figure 53:
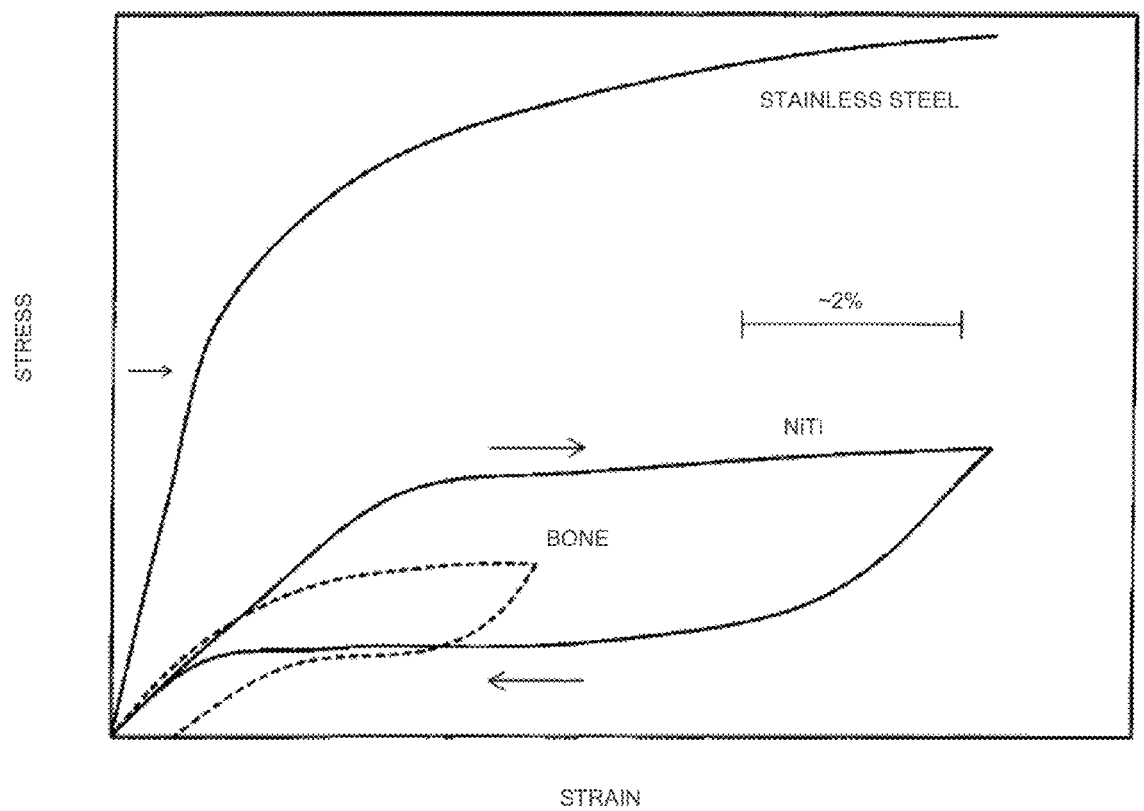
FIG. 53 is stress-strain diagram for bone, Nitinol and stainless steel.

Nitinol is characterized by a specific stress-strain diagram that is different from the deformation behavior of conventional materials, but similar to that of living tissues. FIG. 53 presents typical stress-strain diagrams for stainless steel, NiTi alloy, and living tissues. In the case of stainless steel, the elastically recovered strain (linear portion) is lower than 0.5%. Once the elastic limit is exceeded, stainless steel yields (dislocation slip) and considerable increase in strain is achieved. This increase in strain, where the metal appears to flow like a viscous liquid, is called plastic deformation and allows the materials to acquire a permanent set that cannot be recovered after the stress is released. In shape memory materials such as Nitinol, early deformation is also linearly proportional to the applied stress. Thereafter, deformation continues without a significant increase in the force (upper loading plateau). During unloading, the constraining force is again constant over a wide range of shapes (unloading plateau). Up to 8% of deformation is recoverable in Nitinol. Bone exhibits more than 1% recoverable strain as well as hysteresis in the loading-unloading cycles. The similarity in the deformation behavior between Nitinol and living tissues contributes to the harmonic performance of dynamic implants under loading-unloading conditions in the body.

The close similarity of Nitinol to natural materials leads to more rapid healing times, less trauma to surrounding tissue and expedited osseointegration. When the deforming stress is released, the strain is recovered at lower stresses.

Method of Shape Setting Shape Memory Alloy (SMA)

Nickel-titanium shape memory metal alloy, Nitinol (NiTi), is a functional material whose shape and stiffness can be controlled with temperature. The metal alloy undergoes a complex crystalline-to-solid phase change called martensite-austenite transformation. As the metal in the high-temperature (austenite) phase is cooled, the crystalline structure enters the low-temperature (martensite) phase, where it can be easily bent and shaped. As the metal is reheated above its transition temperature, its original shape and stiffness are restored. SMA materials exhibit various characteristics depending on the composition of the alloy and its thermal-mechanical work history. The SMA material can exhibit 1-way or 2-way shape memory effects. A 1-way shape memory effect results in a substantially irreversible change upon crossing the transition temperature, whereas a 2-way shape memory effect allows the material to repeatedly switch between alternate shapes in response to temperature cycling. SMA can recover large strains in two ways: shape memory effect (SME) and pseudoelasticity, which is also known as superelasticity (SE). The NiTi family of alloys can withstand large stresses and can recover strains near 8% for low cycle use or up to about 2.5% strain for high cycle use. The titanium beta and near-beta alloys can have SME and SE.

Figure 54:
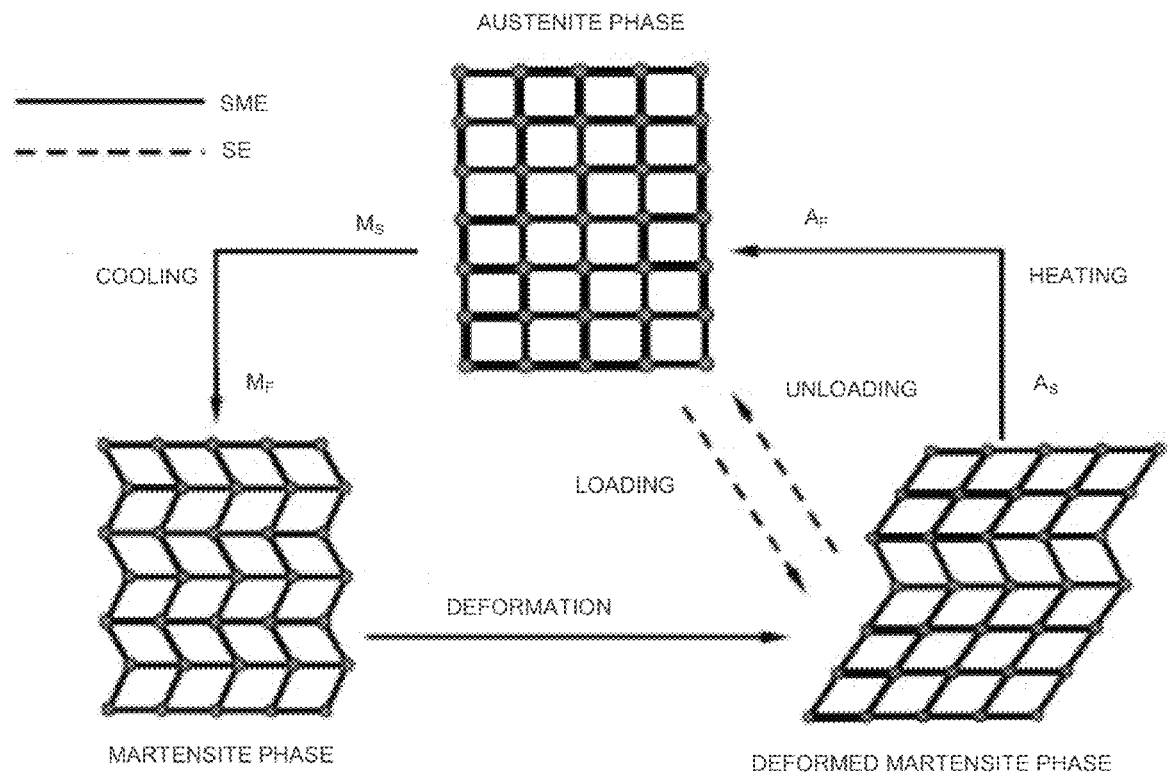
FIG. 54 is a schematic view showing the austenite, martensite and deformed martensite phases for shape memory alloys.

The shape memory alloys, termed as functional materials, show two unique capabilities: shape memory effect (SME) and superelasticity (SE), which are absent in traditional materials. Both SME and SE largely depend on the solid-solid, diffusionless phase transformation process known as martensitic transformation (MT) from a crystallographically more-ordered parent phase (austenite) to a crystallographically less-ordered product phase (martensite). See FIG. 54. The phase transformation (from austenite to martensite, or vice versa) is typically marked by four transition temperatures, commonly referred to as Martensite finish (Mf or $M_f$), Martensite start (Ms or $M_s$), Austenite finish (Af or $A_f$), and Austenite start (As or $A_s$). If the temperatures for Mf<Ms<As<Af, then a change in the temperature within Ms<T<As induces no phase change and both martensite and austenite may coexist within Mf<T<Af. The phase transformations may take place depending on changing temperature (SME) or changing stress (SE).

Aging of Shape Memory Alloy

Figure 55:
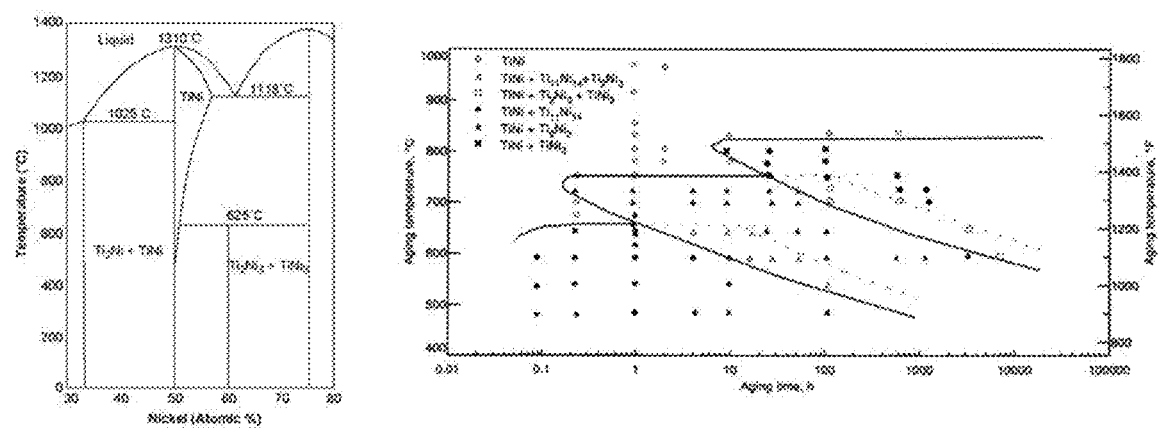
FIG. 55 is a schematic view showing the Nitinol phase diagram.

In many cases it is desirable for the $A_f$ temperature to be close to body temperature (37° C.). In the case of Nitinol, it is possible to commercially purchase the starting material with an $A_f$ around body temperature; however, the transformation temperatures may change as a result of any cold work and heat treatment steps used to manufacture the final product. It is possible to return the Nitinol to its fully annealed state by heating it to 800° C. to 850° C. for 15 to 60 minutes. This will erase all thermomechanical processing. Following this, the $A_f$ temperature can be reset by aging the material. The $A_f$ temperature is effected by the exact matrix composition. As can be seen on the Nitinol phase diagram shown in FIG. 55, as the aging temperature and time increases, nickel rich precipitation reactions occur. This changes how much nickel is in the NiTi lattice. By reducing the amount of nickel in the matrix, aging increases the transformation temperature.

Figure 56:
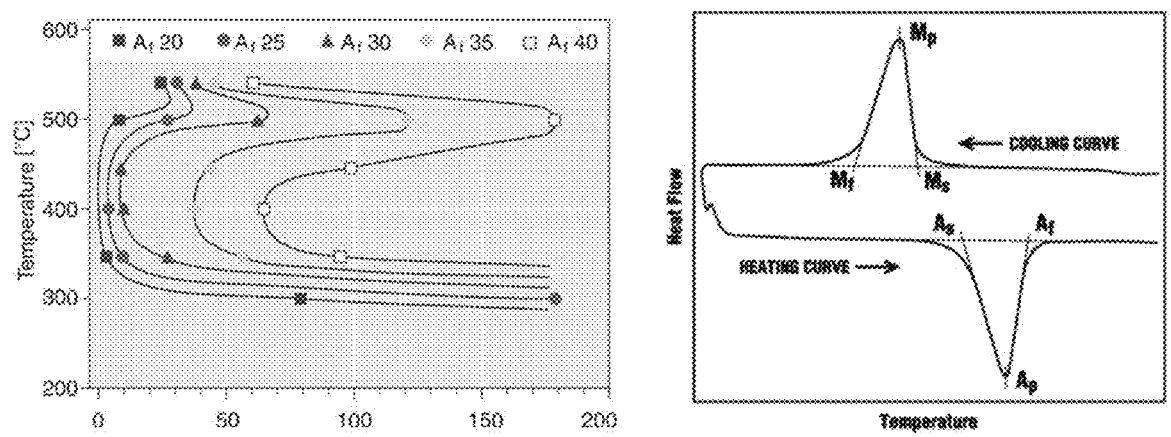
FIG. 56 is a schematic view showing the time-temperature-transformation (TTT) diagram for Nitinol.

It is possible to read a TTT (time-temperature transformation) diagram to determine at what temperature, and for what period of time, to age the Nitinol material so as to achieve an appropriate $A_f$. As seen in the TTT diagram shown in FIG. 56, aging the Nitinol material at 400° C. for approximately 30 minutes results in an $A_f$ close to 37° C. The exact $A_f$ temperature can measured using a differential scanning calorimeter.

Shape Memory Effect (SME)

For T>Af, the SMA is in the parent austenite phase with a particular size and shape. Under stress free condition, if the SMA is cooled to any temperature T<Mf, martensitic transformation (MT) occurs as the material converts to product martensite phase. MT is basically a macroscopic deformation process, though actually no transformation strain is generated due to the so-called self-accommodating twinned martensite. If a mechanical load is applied to this material and the stress reaches a certain critical value, the pairs of martensite twins begin "detwinning" (conversion) to the stress-preferred twins. The "detwinning" or conversion process is marked by the increasing value of strain with insignificant increase in stress. The multiple martensite variants begin to convert to a single variant, the preferred variant determined by alignment of the habit planes with the axis of loading. As the single variant of martensite is thermodynamically stable at T<As, upon unloading there is no reconversion to multiple variants and only a small elastic strain is recovered, leaving the materials with a large residual strain (apparently plastic). Next, if the deformed SMA is heated above Af, SMA transforms to parent phase (which has no variants), the residual strain is fully recovered and the original geometric-configuration is recovered. It happens as if the material recalls from "memory" its original shape before the deformation and fully recovers. Therefore, this phenomenon is termed as shape memory effect (1-way SME). However, if some end constraints are used to prevent this free recovery to the original shape, the material generates large tensile recovery stress, which can be exploited as an actuating force for active or passive control purpose. In accordance with the present invention, SMM dynamic porous coatings can be processed via SME.

Superelasticity (SE)

A second feature of SMA is pseudoelasticity, also known as superelasticity. The superelastic SMA has the unique capability to fully regain the original shape from a deformed state when the mechanical load that causes the deformation is withdrawn. For some superelastic SMA materials, the recoverable strains can be on the order of 10%. This phenomenon, sometimes termed pseudoelasticity or superelasticity (SE), is dependent on the stress-induced martensitic transformation (SIMT), which in turn depends on the states of temperature and stress of the SMA. To explain the SE effect, consider the case where an SMA, which has been entirely in the parent phase (T>Af), is mechanically loaded. Thermodynamic considerations indicate that there is a critical stress at which the crystal phase transformation from austenite to martensite can be induced. Consequently, the martensite is formed because the applied stress substitutes for the thermodynamic driving force usually obtained by cooling for the case of SME. The load, therefore, imparts an overall deformation to the SMA specimen as soon as a critical stress is exceeded. During unloading, because of the instability of the martensite at this temperature in the absence of stress, the reverse phase transformation starts from the SIM to parent phase. When the phase transformation is complete, the SMA returns to its parent austenite phase. Therefore, superelastic SMA shows a typical hysteresis loop (known as pseudoelasticity or superelasticity), and if the strain during loading is fully recoverable, it becomes a closed loop. It should be noted that SIMT (or the reverse SIMT) are marked by a reduction of the material stiffness. Usually the austenite phase has much higher Young's modulus in comparison with the martensite phase.

Nitinol cardiovascular stents, orthodontic wires and other commercially available wire and thin wall tubing products utilize the material's superelastic characteristics. The material's Af temperature is set in relation to body temperature. Stress induced martensite transformation (SIMT) is used to help collapse the diameter of a device to facilitate minimally invasive insertion into the body. The material is expanded in the body once free from its constrained/stressed state, desirably applying a long-term compression of tissues or bones.

SME and SE Behavior of Dynamic Porous Coating

Figure 57:
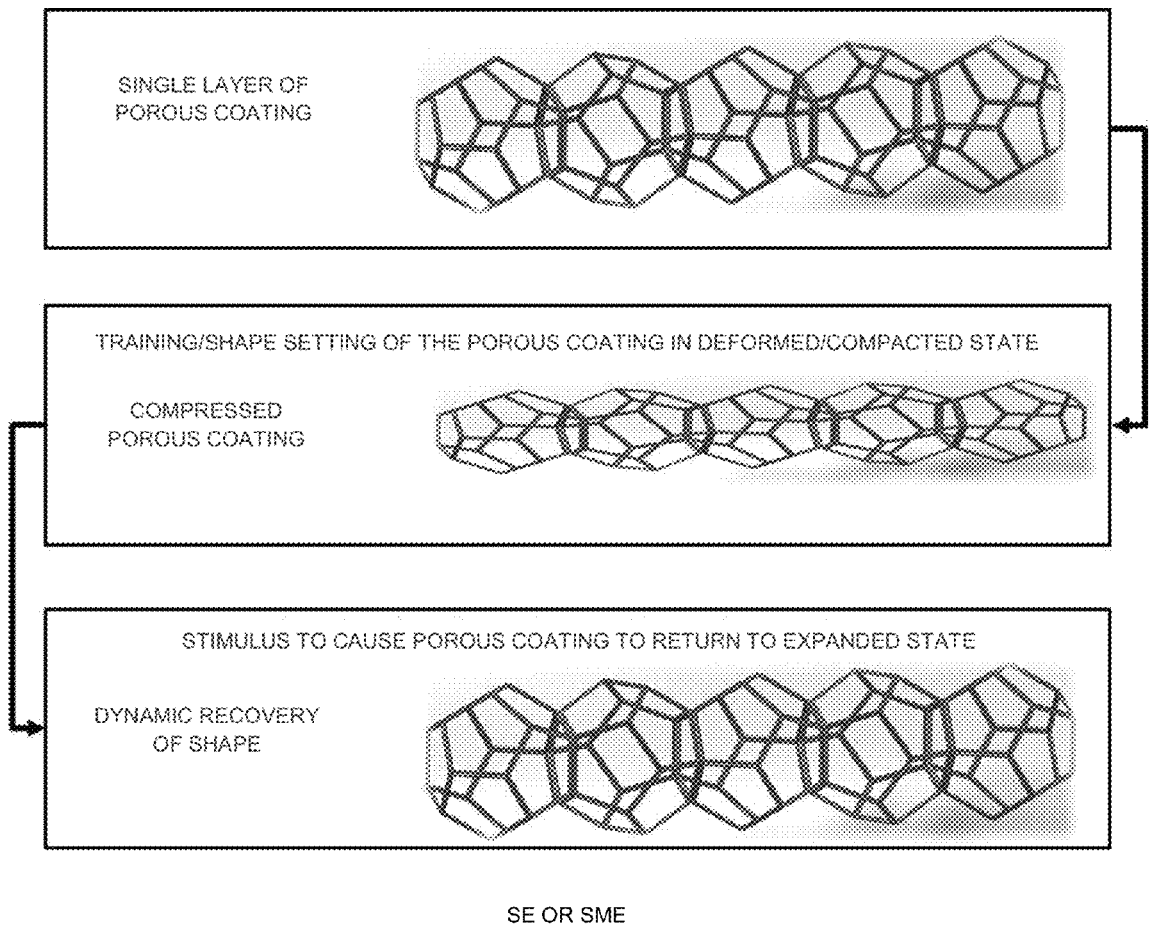
FIG. 57 is a schematic view showing how a shape memory material dynamic porous coating can exhibit superelasticity or shape memory effect.

The SMM dynamic porous coatings of the present invention can exhibit 1-way or 2-way shape memory effects and can exhibit SE or SME. See FIG. 57.

Figure 58:
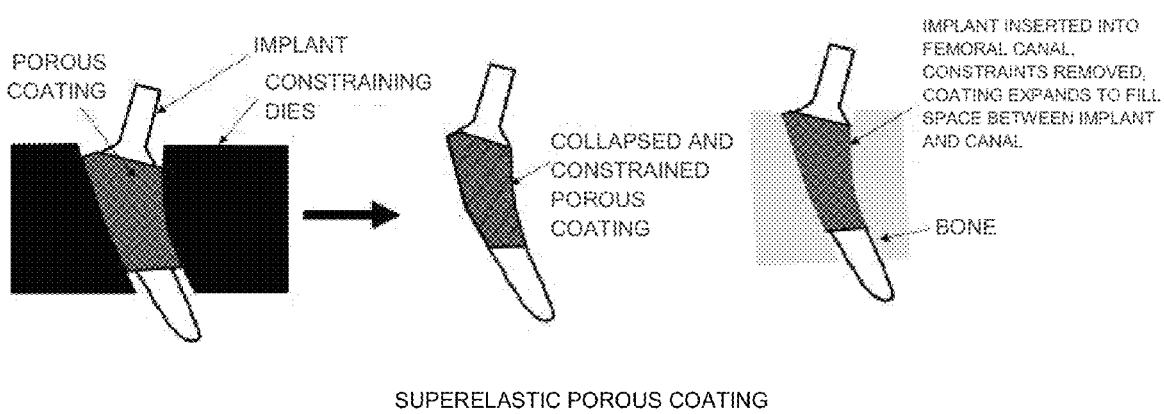
FIG. 58 is a schematic view showing use of a superelastic porous coating in bone.

The dynamic porous coating of the present invention can be designed to exhibit superelastic properties. As an example of a superelastic porous coating, a Nitinol porous structure is first sintered to the implant stem. Shape setting is then accomplished by firmly constraining the material and aging it at approximately 400° C. for 30 minutes, resulting in an $A_f$ of 37° C. The time and temperatures can vary depending on the desired $A_f$. The dynamic porous coating is then compressed and constrained. The implant can then be inserted into the femoral canal and the constraining force removed. With the constraint removed, the dynamic porous coating will attempt to return to its shape-set geometry as it warms to 37° C., filling any gaps between the implant and bone, and applying strain to the bone if the bone keeps the material from fully recovering its shape. See FIG. 58. Alternatively, following shape setting, the implant need not be compressed and constrained. Instead, the implant can be pressed into the femoral canal and deform to fill the space between the implant and the canal. In this case, the pore structure of the dynamic porous coating can be designed so that the coating readily collapses.

Alternatively, the dynamic porous coating disclosed in this invention can exhibit shape memory effects. As an example, a Nitinol porous structure is first sintered to the implant stem. The implant and coating are then aged at approximately 400° C. for 30 minutes, resulting in an $A_f$ of 37° C. The time and temperatures can vary depending on the desired $A_f$. The implant is then kept at below its $A_s$ temperature, and the dynamic porous coating is compressed. When the compressive force is removed, the dynamic porous coating will recover approximately 50% of its strain, leaving the dynamic porous coating with residual strain. The implant can then be inserted to the femoral canal, and as it warms to 37° C., the dynamic porous coating will expand and recover its original shape.

Figure 59:
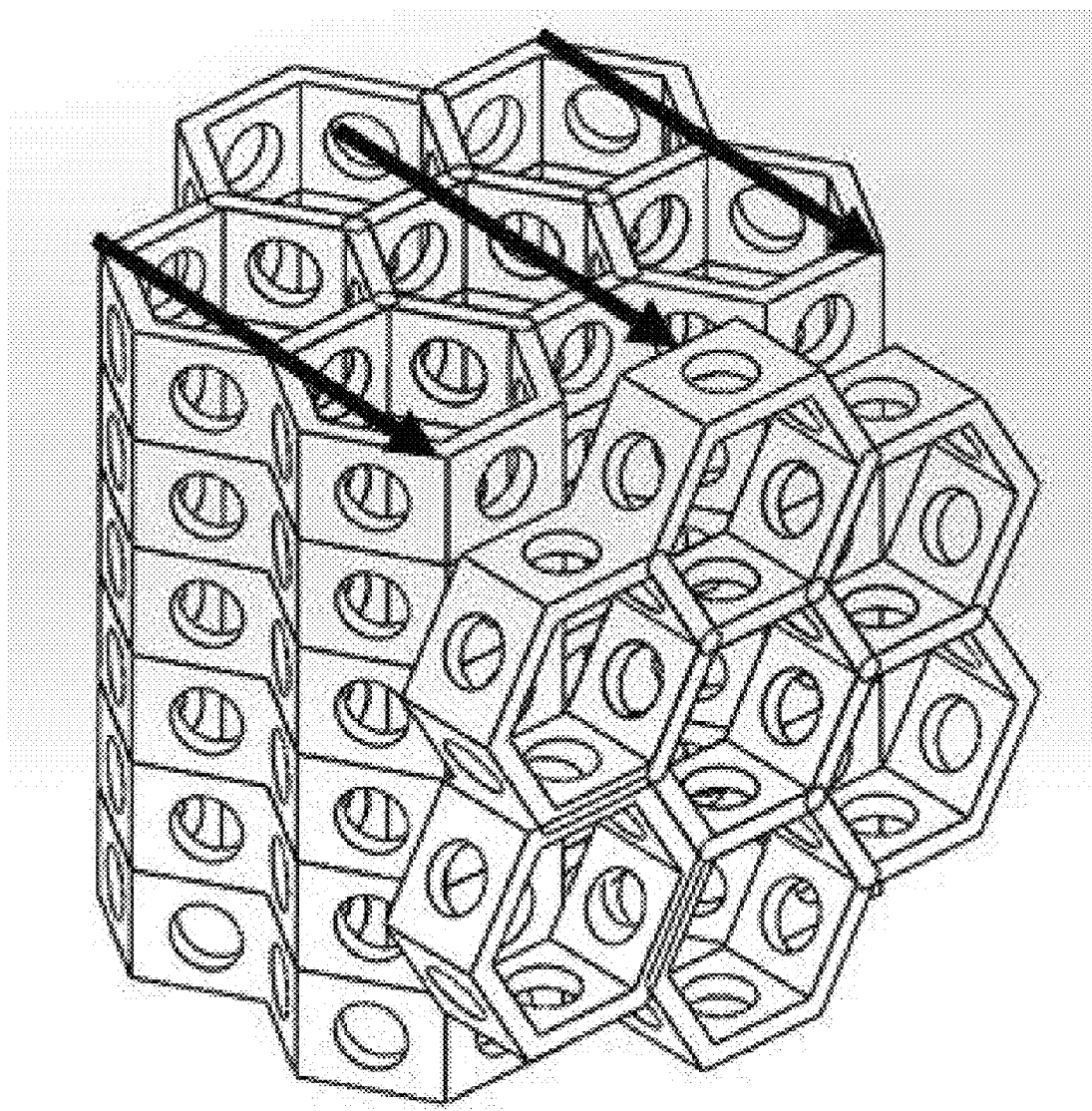
FIG. 59 is a schematic view showing superelasticity with a honeycomb-shape structure.

When these effects are applied to the honeycomb-shaped structures, similar behavior is observed. See FIG. 59. Additionally, the shape recovery of the honeycomb, combined with multiple directions of the honeycomb structure, can be used to force a largely open surface of the dynamic porous coating into direct contact with bone so as to further induce osseointegration and establish early fixation of the implant.

Effect of Dynamic Porous Coating on Osseointegration

Bone adapts and remodels in response to the stress applied to the bone. Wolff's Law states that bones develop a structure which is most suited to resist the forces acting upon them, adapting both the internal architecture and the external conformation to the change in external loading conditions. When a change in loading pattern occurs, stress and strain fields in the bone change accordingly. Bone tissue seems to be able to detect the change in strain on a local basis and then adapt accordingly. The internal architecture is adapted in terms of change in density, and in disposition, of trabecules and osteons, and the external conformation in terms of shape and dimensions. When strain is intensified, new bone is formed. On a microscopic scale, bone density is raised, and on a macroscopic scale, the bone external dimensions are incremented. When strain is lowered, bone resorption takes place. On a microscopic scale, bone density is lowered, and on a macroscopic scale, the bone external dimensions are reduced. Undesirable stress shielding often causes aseptic implant loosening. When the expanding SMM dynamic porous coating applies stress to the bone tissue, apposition will take place and bone density levels will maintain or even increase. Thus, the use of a dynamic porous coating enhances bone growth adjacent the implant, which will assist bone ingrowth into the interconnecting dynamic porous coating.

A dynamic porous coating allows surgeons to coat the coating, or fill the pores of the coating, with hydroxyapatite, tricalcium phosphate and other bone-making agents known in the art, which will remain intact during implant impaction. Current cementless hip and knee implants, for example, are wedged into the femoral or tibial bone by means of hammering the implant with a mallet so as to drive the implant into the prepared bone cavity. A tight interference fit between the implant and femoral bone, however, may undesirably scrape and/or "squeegee" off any substances (e.g., drugs) applied to their surfaces. A dynamic porous coating will allow the implant to be collapsed through SIMT, coated, and then inserted into the femoral canal without the "squeegeeing" effect, and thereafter dynamically expanded either through SE or SME. As a result, the pores of the dynamic porous coating can be treated with biologically active agents so as to prevent periprosthetic infection.

Figure 60:
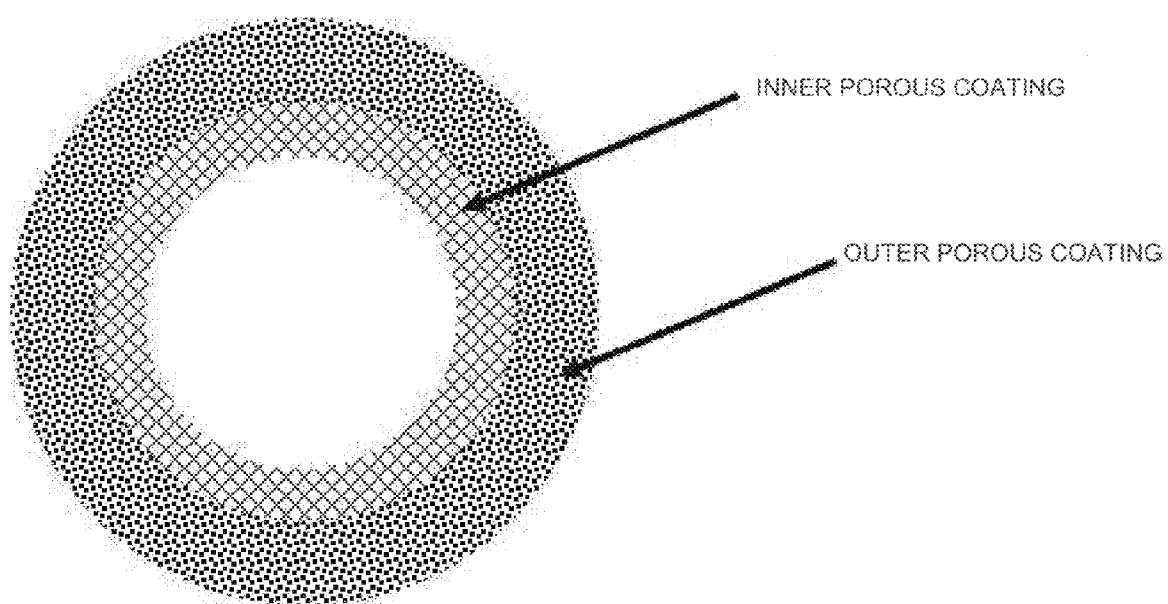
FIG. 60 is a schematic view showing how a dynamic porous coating can comprise an inner porous coating and an outer porous coating, wherein the inner porous coating is different than the outer porous coating.

A dynamic porous coating can be created with two different surface characteristics on the inner and outer surfaces. Using a medullary stent as an example, the outer surface of the stent that comes into contact with the bone can be prepared with a dynamic porous coating suitable for osseointegration. The inner surface of the stent can be prepared with a dynamic porous coating tailored for the generation of new bone marrow. See FIG. 60. The pore size and frequency of the layers of the dynamic porous coating can be varied as required.

Physical Properties of Dynamic Porous Coating

Figure 61:
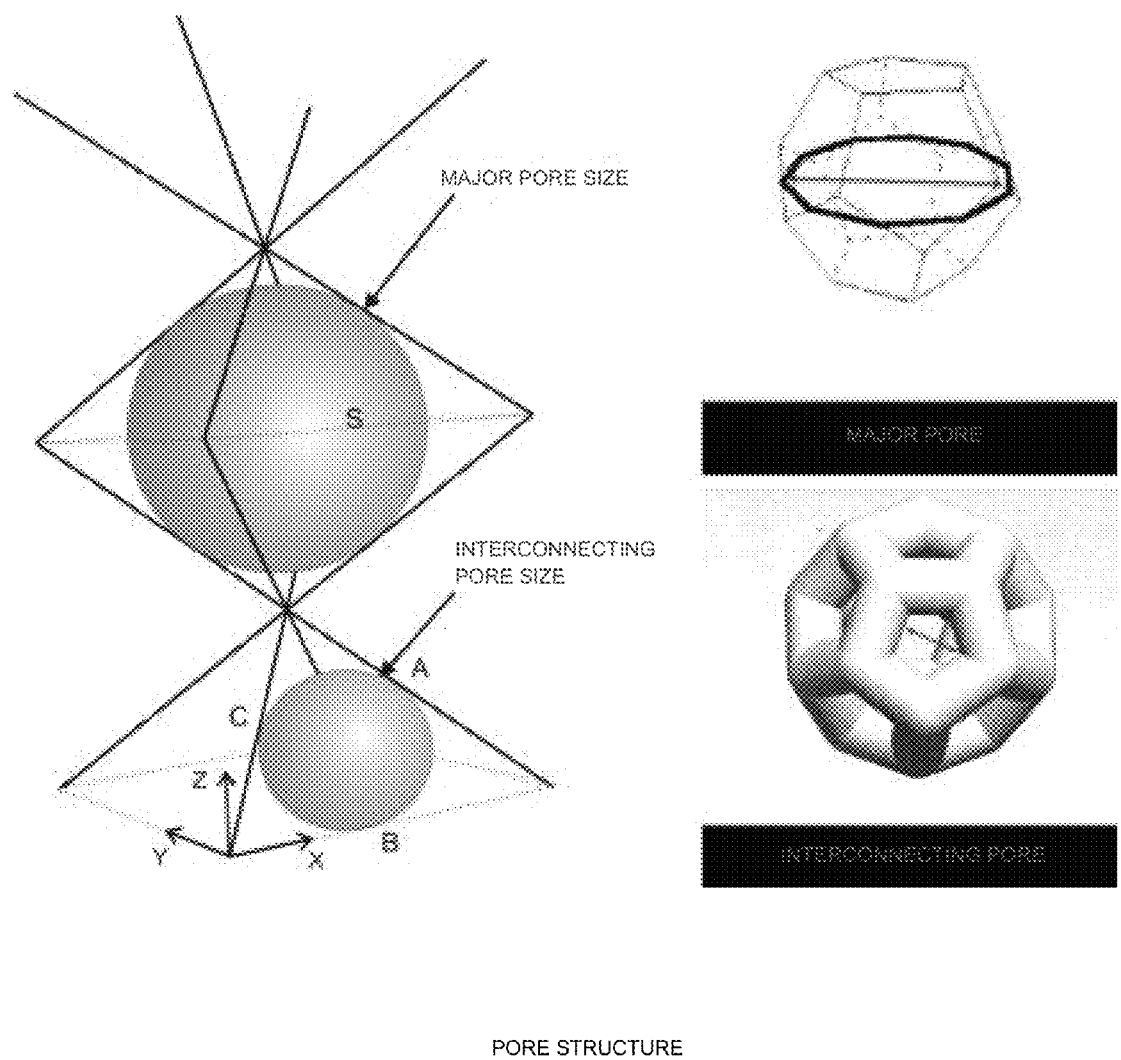
FIG. 61 is a schematic view showing the pore structure of a dynamic porous coating.

The dynamic porous coating is defined by an open pore structure comprising of a web of struts that form a basic dodecahedron structure with major and interconnecting pores. See FIG. 61.

Figure 62:
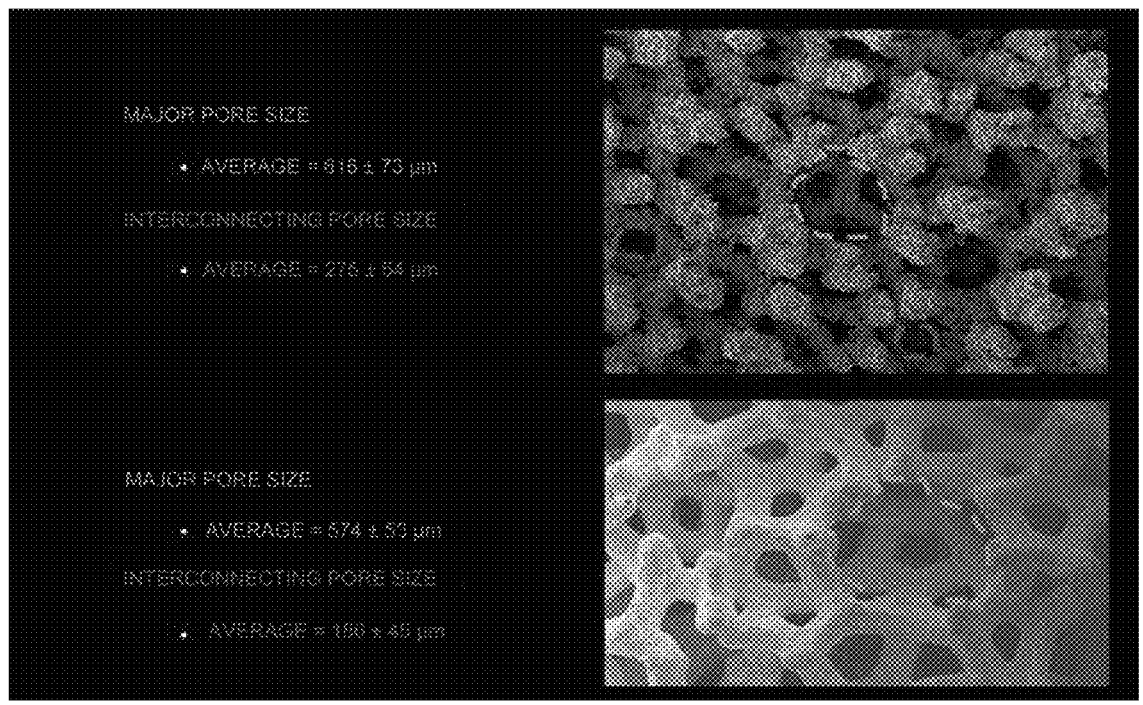
FIGS. 62-65 are schematic views providing further details of porous coatings formed in accordance with the present invention.
Figure 63:
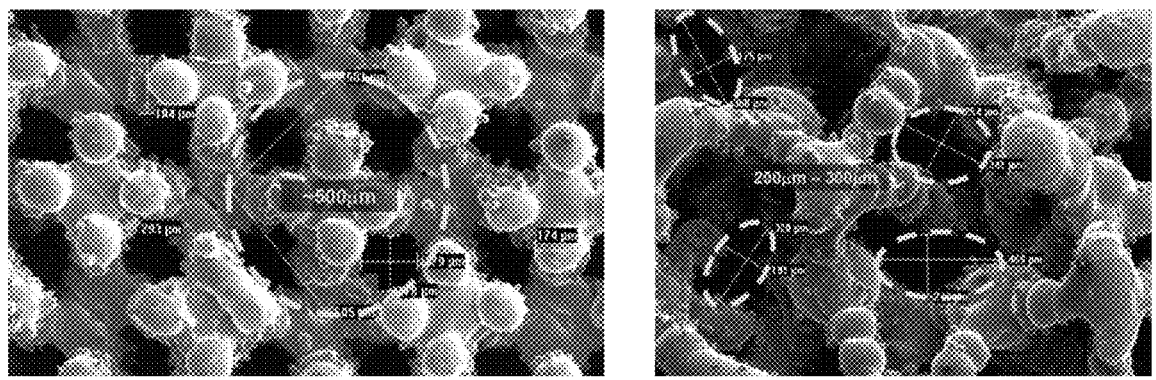
Figure 64:
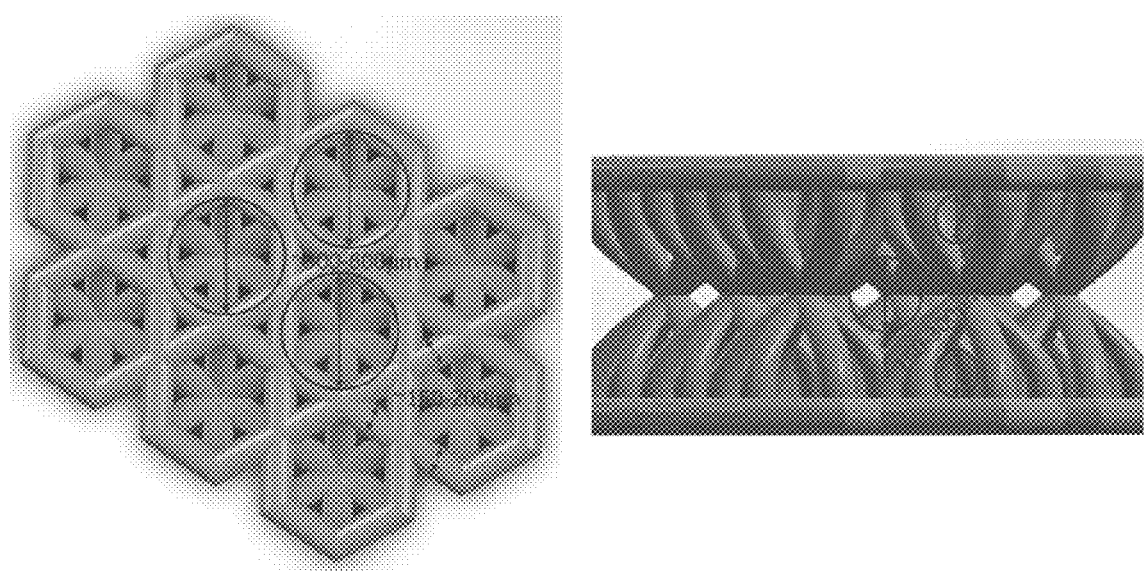

In one preferred form of the invention, the dynamic porous coating has major pore size between approximately 500 µm and 600 µm, and interconnecting pores between 150 µm and 300 µm. It may be beneficial to initial fixation and osseointegration for the surface which is in direct contact with the bone to have pores with a small diameter (in the range of 200 µm to 500 µm). The average porosity of the dynamic porous coating is preferably between 65% and 90%. See FIGS. 62-64.

Figure 65:
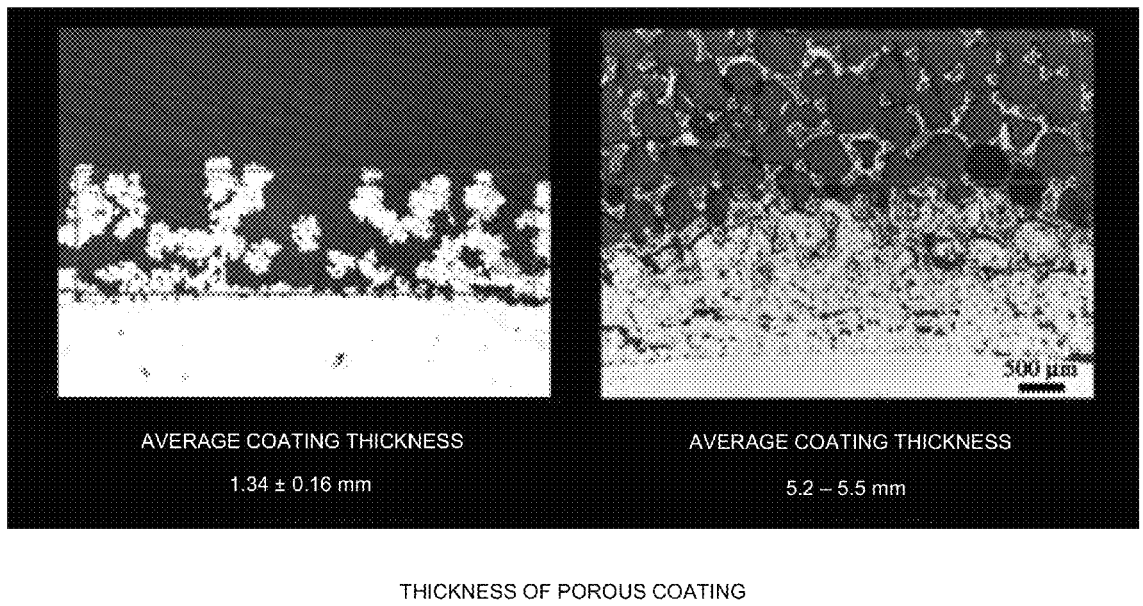

The dynamic porous coating is preferably between approximately 1 mm and 5.5 mm in thickness. It may be built out of a single layer, or several layers stacked on top of each other. See FIG. 65.

Shape Memory Material (SMM) Construct is a Scaffold for Titanium or Tantalum Porous Coating The shape memory material construct described above, which can be made from Nitinol wire by weaving, braiding or knitting, honeycomb, or truss-based structures, sintered beads, and lamination of multiple layers, can be a dynamic or superelastic scaffold for an additional, more traditional coating to be applied on top of it, e.g., a porous trabecular analog structure. By way of example but not limitation, the shape memory material construct can be diffusion bonded, sintered, or brazed to a titanium alloy or cobalt chrome alloy implants to create a dynamic or superelastic scaffold. An additional porous coating can be bonded on top of the SMM scaffold construct. This second porous coating being applied on top of the shape memory construct can be a titanium alloy or tantalum alloy and can be in various porous forms which have already been commercialized such as Regenerex, Biofoam, Tritanium, Gription, Stiktite, Trabecular Metal, Fiber Metal, etc. On one side, these secondary porous coatings will adhere to the SMM scaffold construct through vapor deposition, chemical vapor deposition, plasma spray, foam metal, sputtering, sintering powders and beads, and additive manufacturing processes, and on the other side will be in contact with the bone tissue. This concept creates a three tier implant:

Substrate: implant material (titanium or cobalt chrome alloys)
Middle Scaffold: Shape Memory Material (Nitinol, exhibiting superelasticity or shape memory effect)
Top Layer: Porous Coating (titanium alloy or tantalum alloy) this layer contacts the bone.

The SMM scaffold construct can be superelastic (SE) which is capable of restoring its shape once it is unconstrained and made to spring back, and/or it can have shape memory effect (SME), which allows it to be dynamic under the influence of temperature change, e.g., body temperature. The trabecular coating applied on top of the SMM substrate can be static or dynamic. However, it is the bottom SMM scaffold construct that will give the top layer elasticity, flexibility and superelasticity.

Dynamic Porous Coating

Thus it will be seen that the present invention comprises the provision and use of a novel dynamic porous coating, preferably made of shape memory material, that is applied and bonded to the surface of an orthopedic implant and which is capable of expanding once inserted into the bone via superelasticity or shape memory effect (temperature change) so as to create an interference fit between the implant and bone tissue. The expansion may be initiated by either removal of a containment sleeve (superelasticity effect), or by the warming of the material from a temperature below body temperature to body temperature (shape memory effect). The strain from the expanding implant can cause bone remodeling, enhance osseointegration and will facilitate immediate fixation and long term apposition. The structure of the dynamic porous coating can be 3D with interconnection pores similar to trabecular bone or a 3D honeycomb structure to facilitate bone ingrowth into the coating. The strength and stiffness of the dynamic porous coating can be accurately matched to bone.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for providing therapy to a patient, the method comprising:
providing an orthopedic implant comprising a substrate and a dynamic porous coating secured to the substrate, wherein the dynamic porous coating comprises a porous spacer fabric formed of shape memory material, wherein the porous spacer fabric comprises three distinct layers, a top layer which provides for bone integration, a bottom layer which provides for securing to the substrate, the top layer and the bottom layer extending parallel to one another, and an intermediate layer formed by fibers which extend between the top layer and the bottom layer so as to provide spring between the top layer and the bottom layer, wherein the dynamic porous coating is adapted to apply an expansive force against adjacent bone so as to create an interference fit between the orthopedic implant and the adjacent bone; and
inserting the orthopedic implant into a bone cavity in the patient so that the dynamic porous coating applies an expansive force against adjacent bone so as to create an interference fit between the orthopedic implant and the adjacent bone.

2. A method according to claim 1 wherein the expansive force is created by the superelasticity of the shape memory material.

3. A method according to claim 1 wherein the expansive force is created by the shape memory effect of the shape memory material.

4. A method according to claim 1 wherein the fibers of the intermediate layer extend at an angle of 30° to 150° from the top and bottom layers.

5. A method according to claim 4 wherein the expansive force is created by the superelasticity of the fibers.

6. A method according to claim 4 wherein the expansive force is created by the shape memory effect of the fibers.

7. A method according to claim 1 wherein the expansive force applied by the dynamic porous coating causes bone remodeling.

8. A method according to claim 1 wherein the dynamic porous coating comprises wire which is knit, woven or braided.

9. A method according to claim 1 wherein the orthopedic implant is inserted into the patient during revision surgery.

* * * * *